(12) United States Patent
Dominique et al.

(10) Patent No.: US 8,088,936 B2
(45) Date of Patent: Jan. 3, 2012

(54) LEUKOTRIENE B4 INHIBITORS

(75) Inventors: Romyr Dominique, Wayne, NJ (US); Robert Alan Goodnow, Jr., Gillette, NJ (US); Agnieszka Kowalczyk, Mine Hill, NJ (US); Qi Qiao, Bloomfield, NJ (US); Achyutharao Sidduri, Livingston, NJ (US); Jefferson Wright Tilley, North Caldwell, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 133 days.

(21) Appl. No.: 12/720,822

(22) Filed: Mar. 10, 2010

(65) Prior Publication Data

US 2010/0240678 A1     Sep. 23, 2010

Related U.S. Application Data

(60) Provisional application No. 61/162,352, filed on Mar. 23, 2009.

(51) Int. Cl.
C07D 317/44    (2006.01)
A61K 31/405   (2006.01)

(52) U.S. Cl. .................................. 549/447; 514/415

(58) Field of Classification Search .................. 549/447; 514/415
See application file for complete search history.

(56) References Cited

FOREIGN PATENT DOCUMENTS
WO    2009/024492    2/2009

OTHER PUBLICATIONS

Bioorganic & Medicinal Chemistry Letters (1994), 4(24), 2883-8.
Modern Arene Chemistry 2002, 53-106.
J.Org.Chem.1997, 62,8215-8217.
Knochel, Chem. Rev. 1993, 93, 2117.
Klement, I., Tetrahedron 1996, 52, 7201.
Knochel, Tetrahedron 1998, 54, 8275.
Siegfried, J. Med. Chem. 2000, 43, 1670.
J. Org. Chem. 1970, 35, 244.
J. Org.Chem. 2003, 68, 8750.
Org. Lett. 2004, 6, 4587.
J. Am. Chem. Soc. 2006, 128, 2180.
J.Org.Chem. 1962, 27, 93.
Tetrahedron 2006, 62, 2357.

*Primary Examiner* — Rita Desai
*Assistant Examiner* — John Mabry
(74) *Attorney, Agent, or Firm* — George W. Johnston; Dennis P. Tamaloni; Samuel H. Megerditchian

(57) ABSTRACT

Provided herein are compounds of the formula (I):

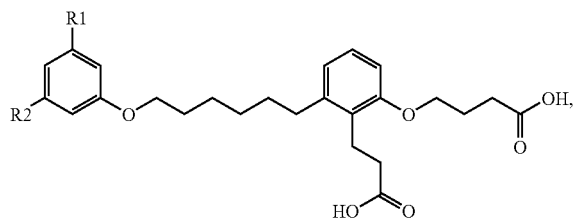

(I)

as well as pharmaceutically acceptable salts thereof, wherein the substituents are as those disclosed in the specification. These compounds, and the pharmaceutical compositions containing them, are useful for the treatment of diseases such as, for example, COPD.

11 Claims, No Drawings

LEUKOTRIENE B4 INHIBITORS

PRIORITY TO RELATED APPLICATION(S)

This application claims the benefit of U.S. Provisional Application No. 61/162,352 filed, Mar. 23, 2009, which is hereby incorporated by reference in its entirety.

RELATED APPLICATIONS

This application is related to U.S. application Ser. No. 12/180,738, filed Jul. 28, 2008; U.S. application Ser. No. 12/326,349, filed Dec. 2, 2008; and U.S. Provisional Application No. 61/034,307, filed Mar. 6, 2008, all pending and all incorporated by reference herein in their entirety.

FIELD OF THE INVENTION

The invention is directed to compounds of formula (I):

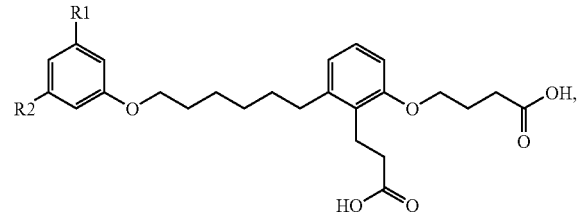

(I)

or pharmaceutically acceptable salts thereof. These compounds inhibit the interaction of leukotriene $B_4$ ($LTB_4$) pro-inflammatory lipid mediator binding to BLT-1 and BLT-2 receptors resulting in amelioration of disease states resulting from excessive inflammatory response, such as, for example, severe asthma and chronic obstructive pulmonary disease (COPD).

All documents cited or relied upon below are expressly incorporated herein by reference.

BACKGROUND OF THE INVENTION $LTB_4$ is a potent pro-inflammatory lipid mediator derived from arachidonic acid through the 5-lipoxygenase signaling pathway. $LTB_4$ is produced by multiple cell types such as neutrophils, monocytes, macrophages, keratinocytes, lymphocytes and mast cells. It functions as a chemoattractant and as an activator of neutrophil cells. It has been shown that $LTB_4$ effects its action through the agonism of G-protein coupled receptors BLT-1 and BLT-2. (Prostaglandins, Leukotrienes and Essential Fatty Acids 69, 2003, 123-134.)

$LTB_4$ is considered to be an important mediator of acute and chronic inflammatory diseases. Increased levels of $LTB_4$ have been detected in the lungs of patients with severe asthma and COPD. Thus, it is anticipated that an effective inhibitor of the action of $LTB_4$ and BLT-1 and -2 would provide effective therapy for the treatment of inflammatory conditions such as asthma and COPD.

A need exists in the art for $LTB_4$ inhibitors that have efficacy for the treatment of diseases such as COPD.

SUMMARY OF THE INVENTION

The present invention pertains to inhibitors of $LTB_4$. In a preferred embodiment, the invention provides for pharmaceutical compounds of the formula (I):

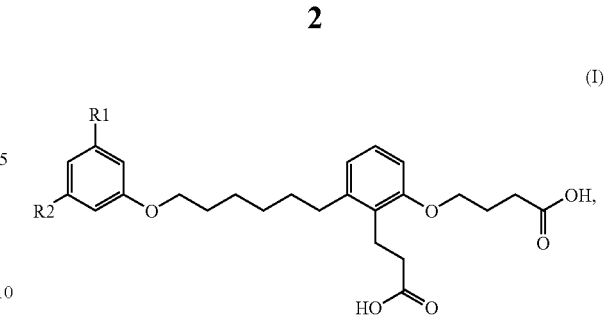

(I)

as well as pharmaceutically acceptable salts thereof, that are useful as inhibitors of $LTB_4$.

DETAILED DESCRIPTION

In an embodiment of the present invention, provided is a compound of formula (I):

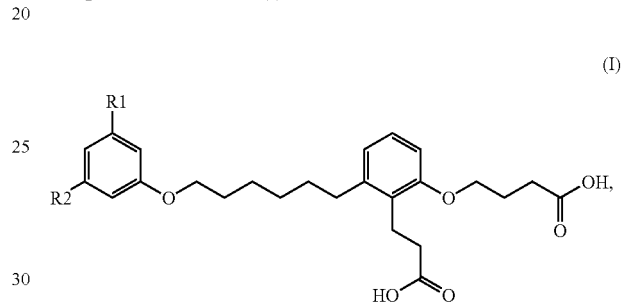

(I)

wherein:
R1 is lower alkyl, alkoxy, alkoyl, dimethylaminomethyl, cyanomethyl, benzyloxy, cyclopentylmethoxy, cyclopropanecarbonyl or cyclopentanecarbonyl; and
R2 is benzo[1,3]dioxol, benzo[1,4]dioxin, benzothiazole, difluoro-benzo[1,3]dioxole, cycloalkyl, aryl, unsubstituted or mono-, di- or tri-substituted with halogen, hydroxy, alkoxy, lower alkyl, —$CF_3$, —$OCF_3$ or methanesulfonyl, heteroaryl, unsubstituted or mono-, di- or tri-substituted with lower alkyl, halogen or hydroxy, N-aryl or indole, unsubstituted or substituted with lower alkyl,
or a pharmaceutically acceptable salt thereof.

In another embodiment of the present invention, provided is a pharmaceutical composition, comprising a therapeutically effective amount of a compound according to claim 1 or a pharmaceutically acceptable salt thereof and a pharmaceutically acceptable carrier.

In a further preferred embodiment, R1 is lower alkyl, alkoxy or alkoyl and R2 is benzo[1,3]dioxol, benzo[1,4]dioxin, benzothiazole, difluoro-benzo[1,3]dioxole, cycloalkyl, aryl, unsubstituted or mono-, di- or tri-substituted with halogen, hydroxy, alkoxy, lower alkyl, —$CF_3$, —$OCF_3$ or methanesulfonyl, heteroaryl, unsubstituted or mono-, di- or tri-substituted with lower alkyl, halogen or hydroxy, N-aryl or indole, unsubstituted or substituted with lower alkyl.

In a still another preferred embodiment, R1 is dimethylaminomethyl, cyanomethyl, benzyloxy, cyclopentylmethoxy, cyclopropanecarbonyl or cyclopentanecarbonyl and R2 is benzo[1,3]dioxol, benzo[1,4]dioxin, benzothiazole, difluoro-benzo[1,3]dioxole, cycloalkyl, aryl, unsubstituted or mono-, di- or tri-substituted with halogen, hydroxy, alkoxy, lower alkyl, —$CF_3$, —$OCF_3$ or methanesulfonyl, heteroaryl, unsubstituted or mono-, di- or tri-substituted with lower alkyl, halogen or hydroxy, N-aryl or indole, unsubstituted or substituted with lower alkyl.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent carbocyclic radical of three to seven, preferably three to six carbon atoms. This term is further exemplified by radicals such as cyclopropyl, cyclobutyl, cyclopentyl and cyclohexyl. In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic monovalent mono- or polycarbocyclic radical, such as phenyl or naphthyl, preferably phenyl.

The term "heteroaryl," alone or in combination with other groups, means a monocyclic or bicyclic radical of 5 to 12 ring atoms having at least one aromatic ring containing one, two, or three ring heteroatoms selected from N, O, and S, the remaining ring atoms being C. Preferred heterocycle groups include, but are not limited to, thiophene, pyrimidine and pyridine. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted. Where substituted, there will generally be, for example, 1 to 3 substitutents present, preferably 1 substituent. The substituents include those that are noted for the alkyl group, supra, such as, for example, hydroxyl.

As used herein, the term "alkoxy" means alkyl-O—; and "alkoyl" means alkyl-CO—. Alkoxy or alkoyl groups may be substituted by, for example, one or more alkyl groups.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

The compounds of the present invention can be prepared by any conventional means. Suitable processes for synthesizing these compounds are provided in the Examples. Generally, compounds of formula I can be prepared according to the Schemes described below. The sources of the starting materials for these reactions are also described.

Scheme 1

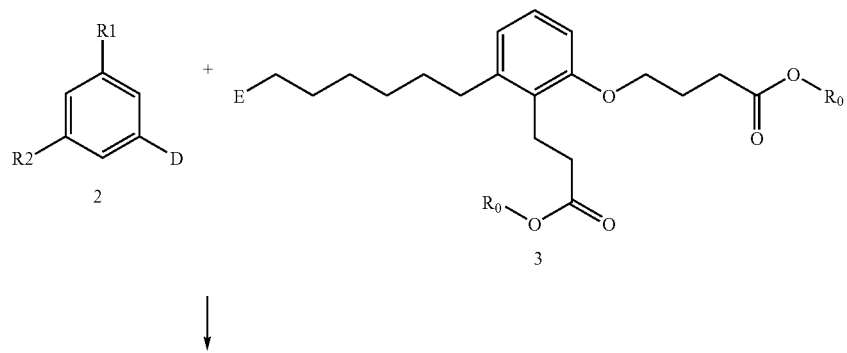

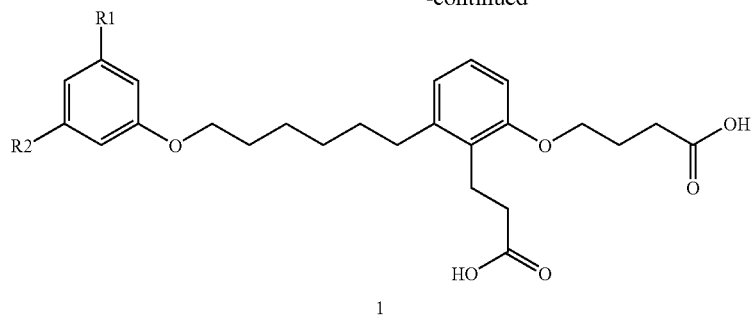

1

The compounds contained within this invention can be synthesized according to the following general synthetic strategies as shown below in Scheme 1. The synthesis of 1 may be effected by condensation of 3, 4-[2-(2-carboxy-ethyl)-3-(6-E-hexyl)-phenoxy]-butyric acid, protected as a di-ester for R0=lower alkyl, preferably as a di-ethyl ester (R0=ethyl), and E is a leaving group, such as a halogen or mesylate with the fragment 2 wherein D is a nucleophile such as a hydroxyl group under standard conditions employed for the alkylation of phenols with primary halides or mesylates. Functional groups represented by symbol R1 being halogen, nitro, and amino group and can be transformed to an aryl, aryl ether, or amine moiety before or after coupling to 3 according to chemistry described in this invention. Functional groups represented by symbol R2 being hydroxy methyl, alkylated hydroxy methyl, cyano methyl, dimethyl amino methyl, ethers or ketones.

A synthesis of 3 for E=Br and $R_0$=Et has been described in *Bioorganic & Medicinal Chemistry Letters* (1994), 4(24), 2883-8. A synthesis of 3 for E=Br and $R_0$=Et is also shown below in Schemes 2 and 3.

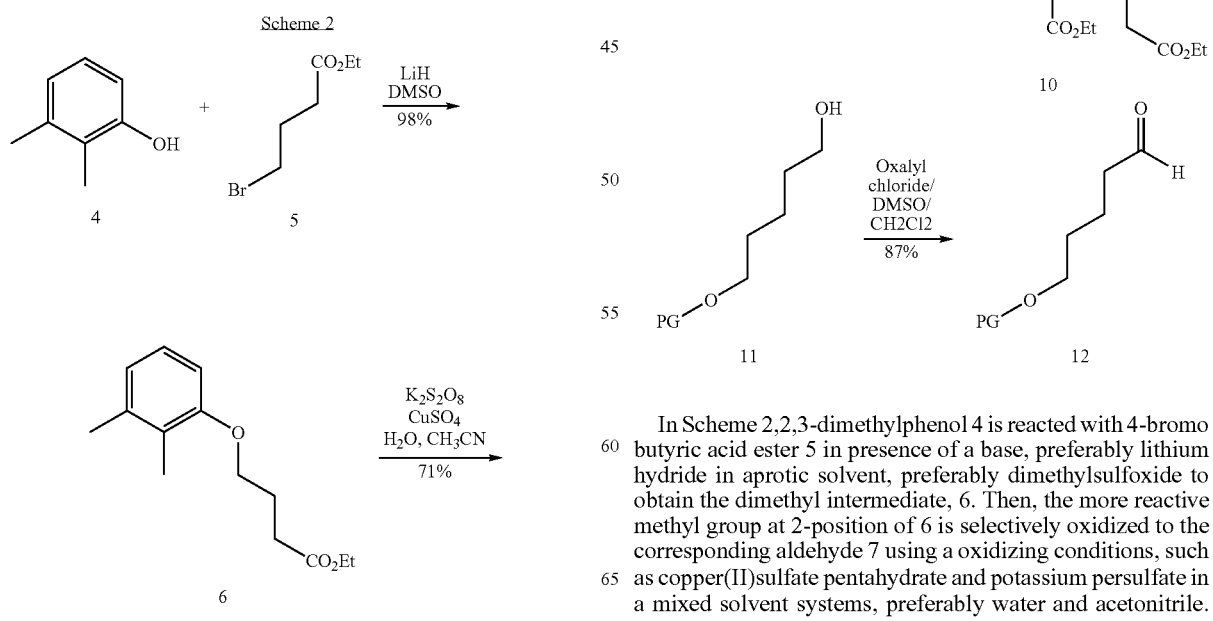

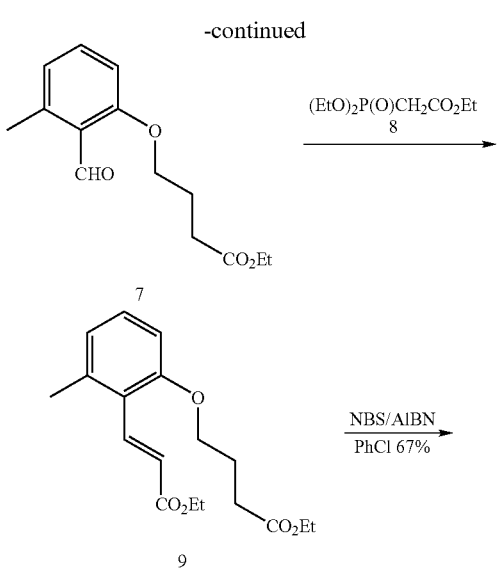

In Scheme 2, 2,3-dimethylphenol 4 is reacted with 4-bromo butyric acid ester 5 in presence of a base, preferably lithium hydride in aprotic solvent, preferably dimethylsulfoxide to obtain the dimethyl intermediate, 6. Then, the more reactive methyl group at 2-position of 6 is selectively oxidized to the corresponding aldehyde 7 using a oxidizing conditions, such as copper(II)sulfate pentahydrate and potassium persulfate in a mixed solvent systems, preferably water and acetonitrile. The two carbon chain ester moiety can be selectively introduced by a modified Horner-Emmons condensation conditions from aldehyde 7 and triethylphosphonoacetate 8 in the presence of a base such as sodium ethoxide in a protic solvents, preferably ethanol. Then, the benzylic bromination of 9 is effected with N-bromosuccinimide in the presence of 2,2'-azobisisobutyronitrile (AIBN) in an aprotic solvents such as carbon tetrachloride or chlorobenzene or benzene. The hydroxy protected 5-carbon chain aldehyde 12 can be obtained by oxidation of a mono protected pentane-1,5-diol with any suitable oxidation conditions such as Swern oxidation or TEMPO oxidation, reactions well known to those skilled in the art. The protecting group on 11 and 12 can be any suitable protecting group for primary alcohols, for example t-butyldimethylsilyl group. Use and removal of protecting groups is well presented in the literature. For a leading reference, see P. G. M. Wuts and T. W. Greene in Green's Protective Groups in Organic Synthesis, Wiley and Sons, 2007.

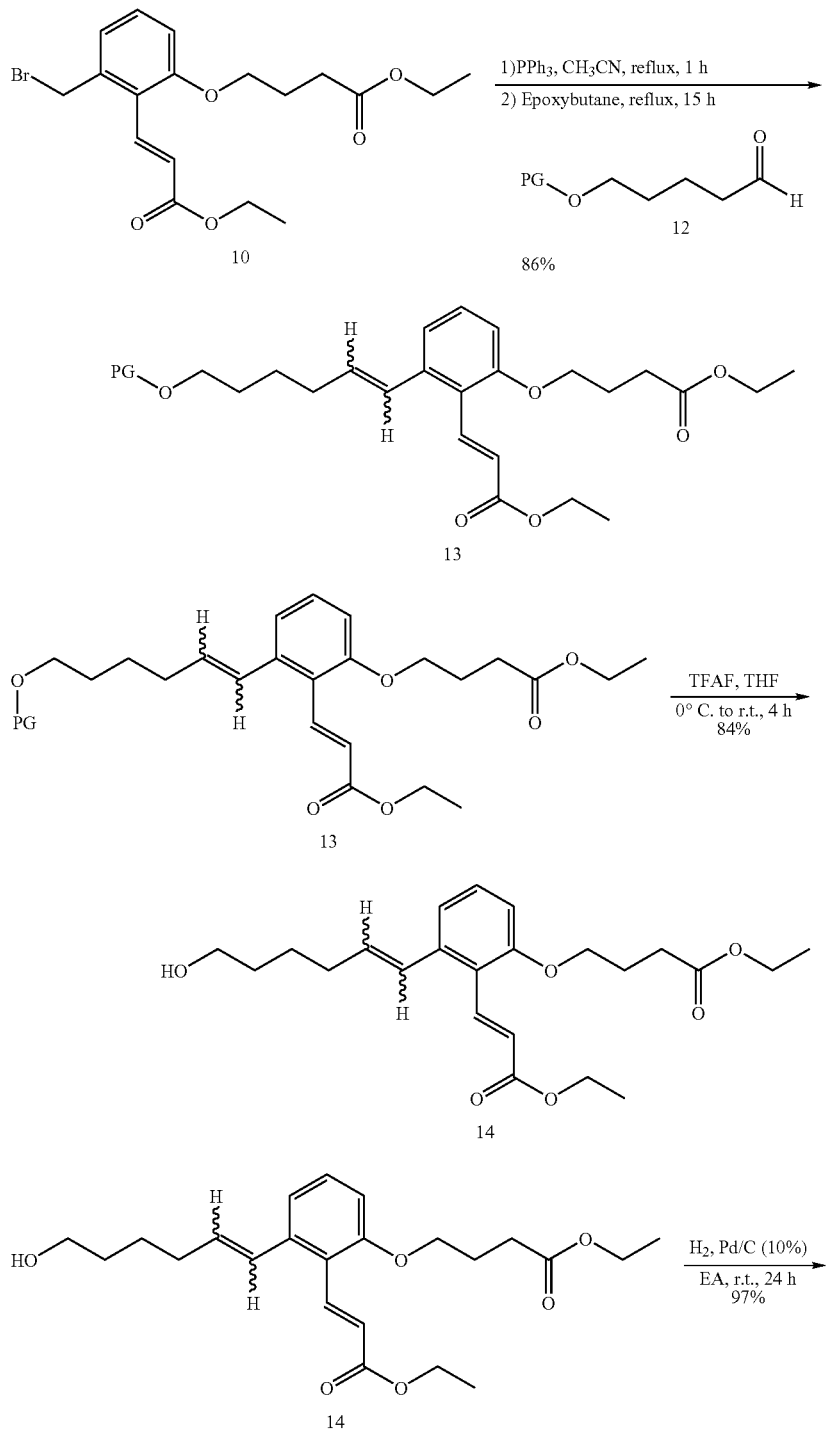

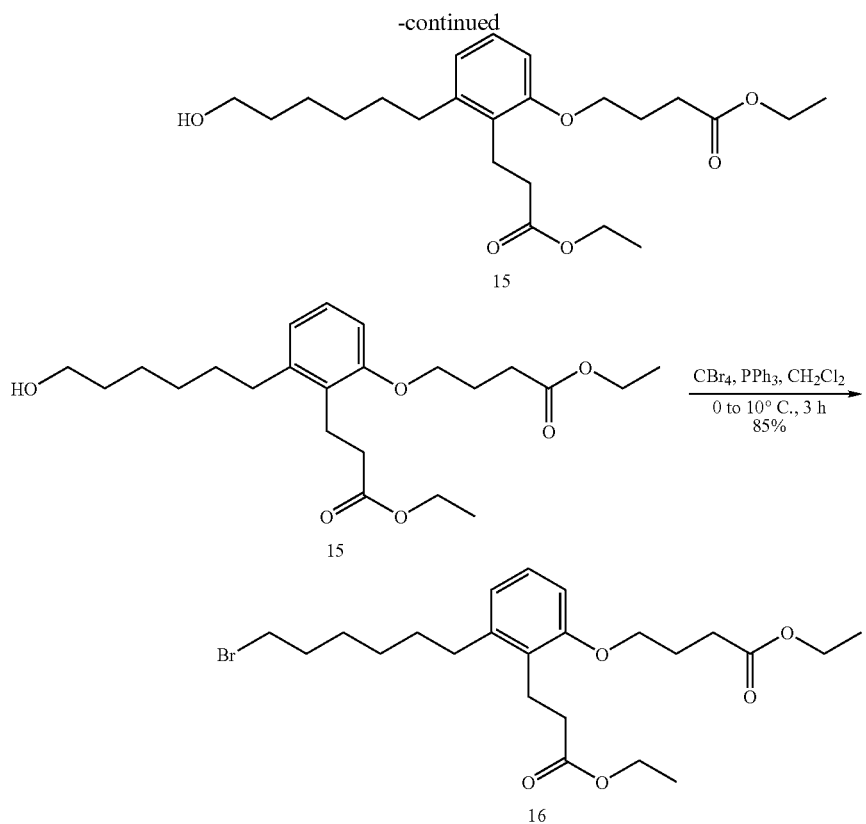

As shown in Scheme 3, a one-pot Wittig condensation reaction is conducted first by making in situ Wittig salt from the benzylic bromide 10 and triphenylphosphine in acetonitrile and then the reaction of the resulting Wittig salt with the protected aldehyde 12 in 1,2-epoxybutane to obtain the olefinic intermediate 13 in a cis to trans ratio of ~1:3. The mixture of cis and trans compounds can be converted to the corresponding alkyl bromide intermediate 16 by removal of the protecting group, using for example tetrabutyl ammonium fluoride for the case wherein the protecting group is a t-butyldimethylsilyl group, hydrogenation of the double bonds, and conversion of the hydroxyl group to the bromide. These transformation are routine and well known to those skilled in the art.

Scheme 4: Method A

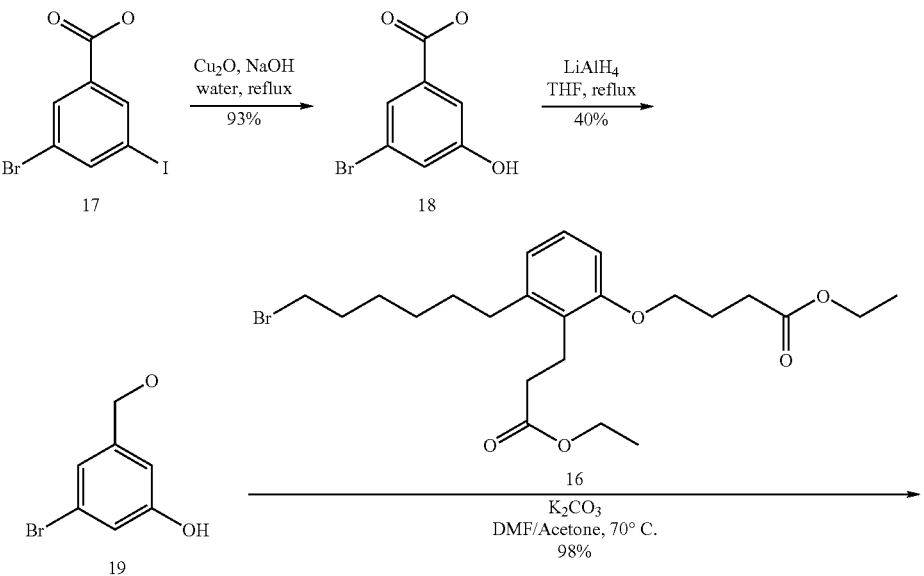

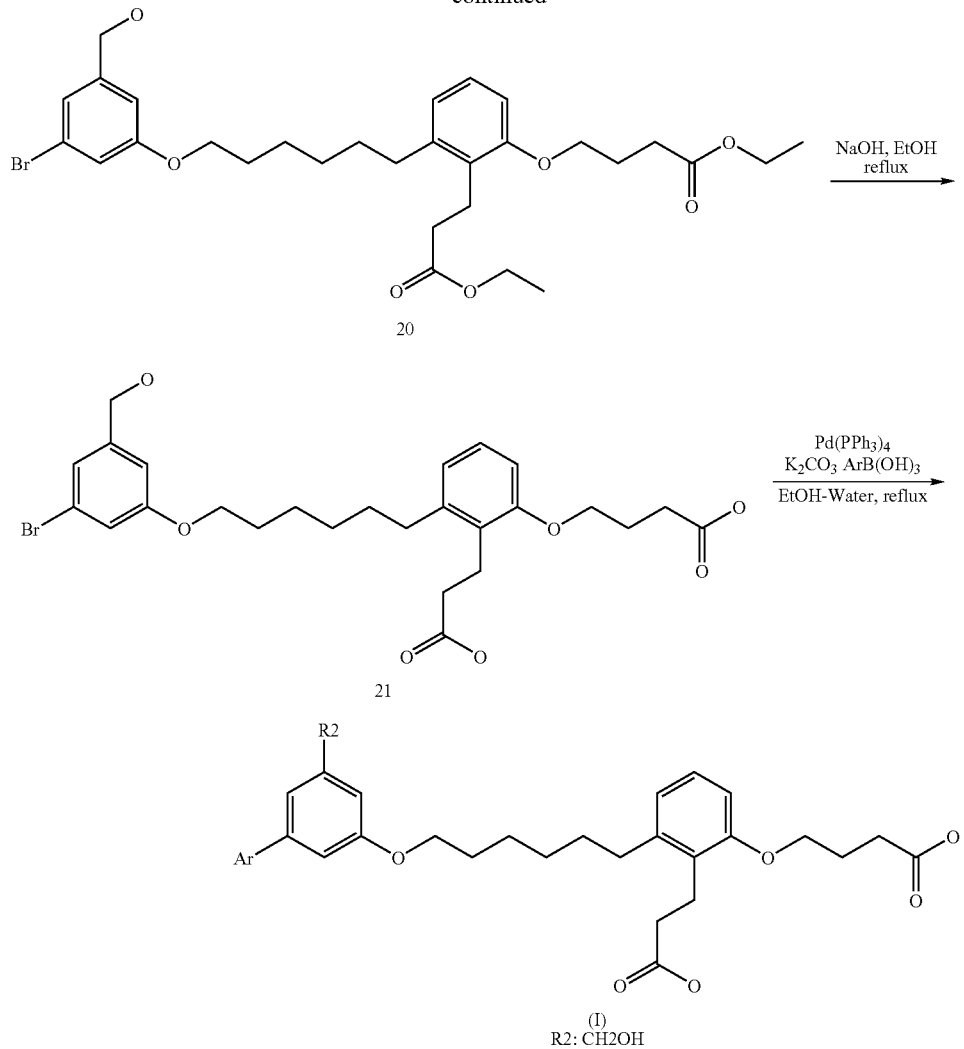

Target molecule (I) where R2 is CH$_2$OH can be synthesized using the Method A described in Scheme 4 starting from commercially available 3-bromo-5-iodo-benzoic acid. The first step consists in the selective displacement of the iodo group by the hydroxide ion using aqueous sodium hydroxide in the presence of catalytic amount of cuprous oxide at a temperature about 100° C. (as described in *Organic Process Research & Development* 2002, 6, 591-596). Reduction of the carboxylic group to benzylic alcohol 19 could be accomplished using a common reducing agent such as lithium aluminium hydride. The coupling reaction between 19 and 16 is regioselective and only the most nucleophilic alcohol functionality reacts to form the desired intermediate 20. The coupling is achieved in a mixture of acetone and N,N-dimethylformamide at a temperature about 75° C. in the presence of a base such as potassium carbonate or cesium carbonate. The ester hydrolysis can be conveniently effected by treating the compound 20 with several equivalents of an alkali metal hydroxide, such as sodium hydroxide, potassium hydroxide or lithium hydroxide, in a suitable solvent such as a mixture of alcohol and water or tetrahydrofuran and water. The reaction can be carried out at a temperature ranging from 0° C. to 70° C. The Suzuki coupling reaction is carried out between aryl bromide 21 and various boronic acids to produce the derivatives of target molecule (I) where R2=CH$_2$OH. The conditions of this method are disclosed in many publications which have been reviewed by A. Suzuki in an article entitled "The Suzuki reaction with arylboron compounds in arene chemistry" in *Modern Arene Chemistry* 2002, 53-106 and in a recent review: *Tetrahedron* 2002, 58, 9633-9695. Generally Suzuki coupling reactions are carried out in the presence of a transition metal catalyst such as a palladium catalyst utilizing and a weak inorganic base. Among the preferred organic solvents are dimethoxyethane, ethanol and toluene. The weak inorganic base can be a carbonate or bicarbonate, such as potassium carbonate or cesium carbonate or phosphate such as potassium phosphate. The reaction can also be done in anhydrous conditions or an aqueous solution of the base can be used. The source of palladium can be palladium(0) complex (e.g. tetrakis(triphenylphosphine)palladium(0)) or a compound which can be reduced in situ to give palladium(0) (for example palladium acetate(II) or bis(triphenylphosphine) palladium(II) chloride or [1,1'bis(diphenylphosphino)ferrocene]dichloropalladium(II)).

Scheme 5: Method B
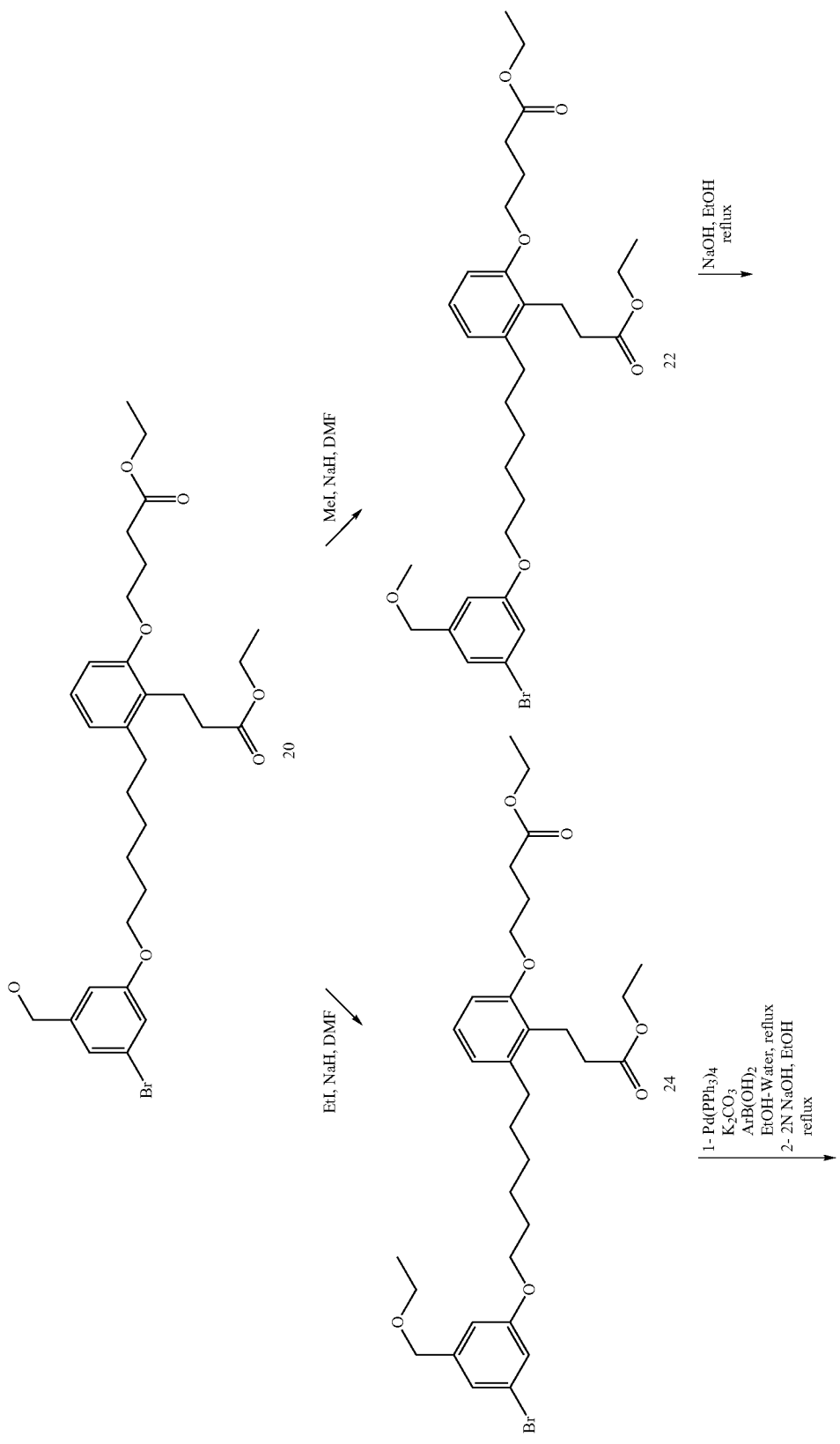

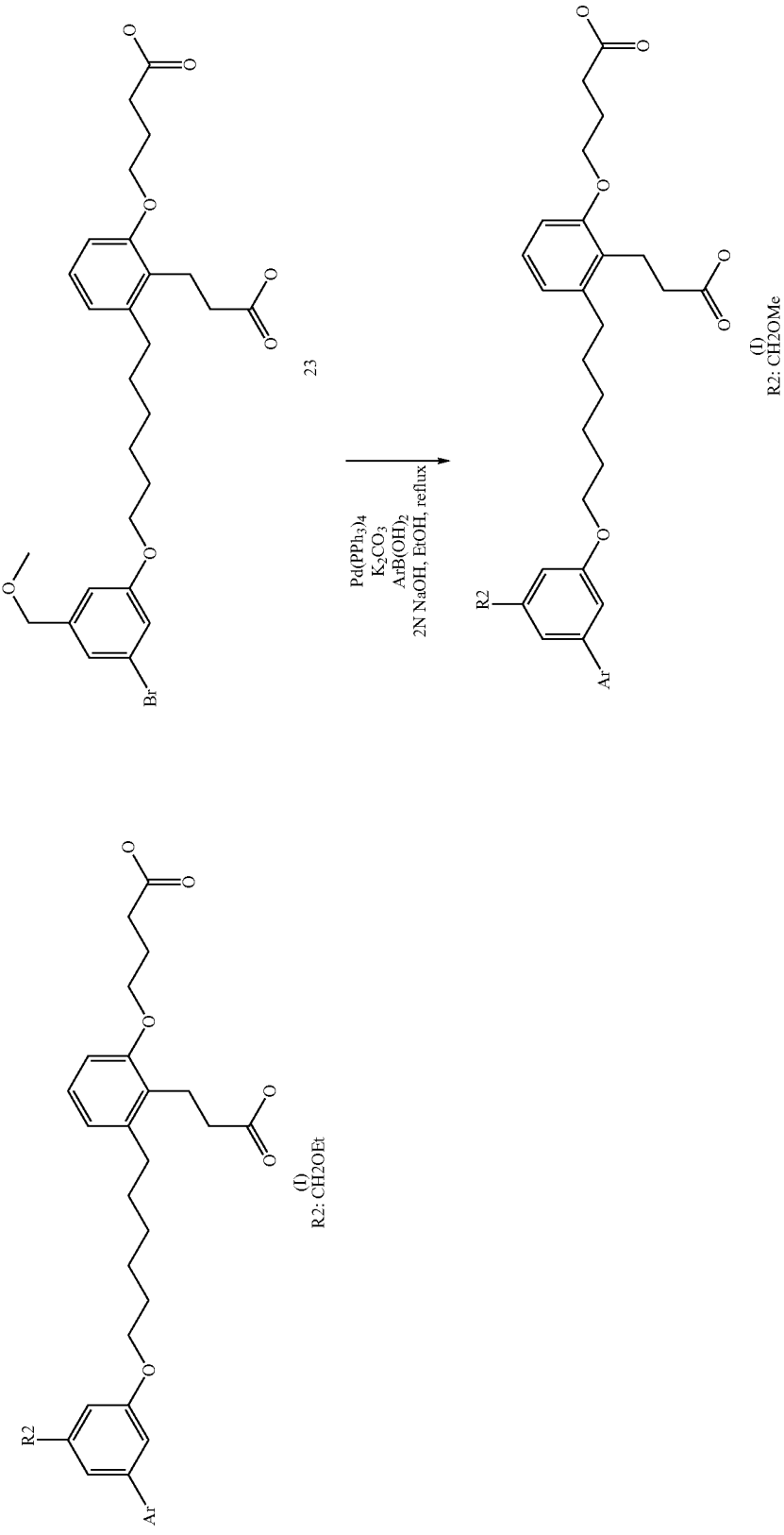

Target molecule (I) where R2 equals $CH_2OMe$ and $CH_2OEt$ can be prepared as described in Scheme 5 starting from intermediate 20. Using a strong base such as sodium hydride, alkylation of the benzylic alcohol could be accomplished in DMF using alkyl halides such as methyl iodide and ethyl iodide. This reaction also known as the Williamson reaction is a very general method allowing the preparation of various unsymmetrical ethers. All the remaining steps leading to preparation of compounds of formula (I) have been described in Methods A.

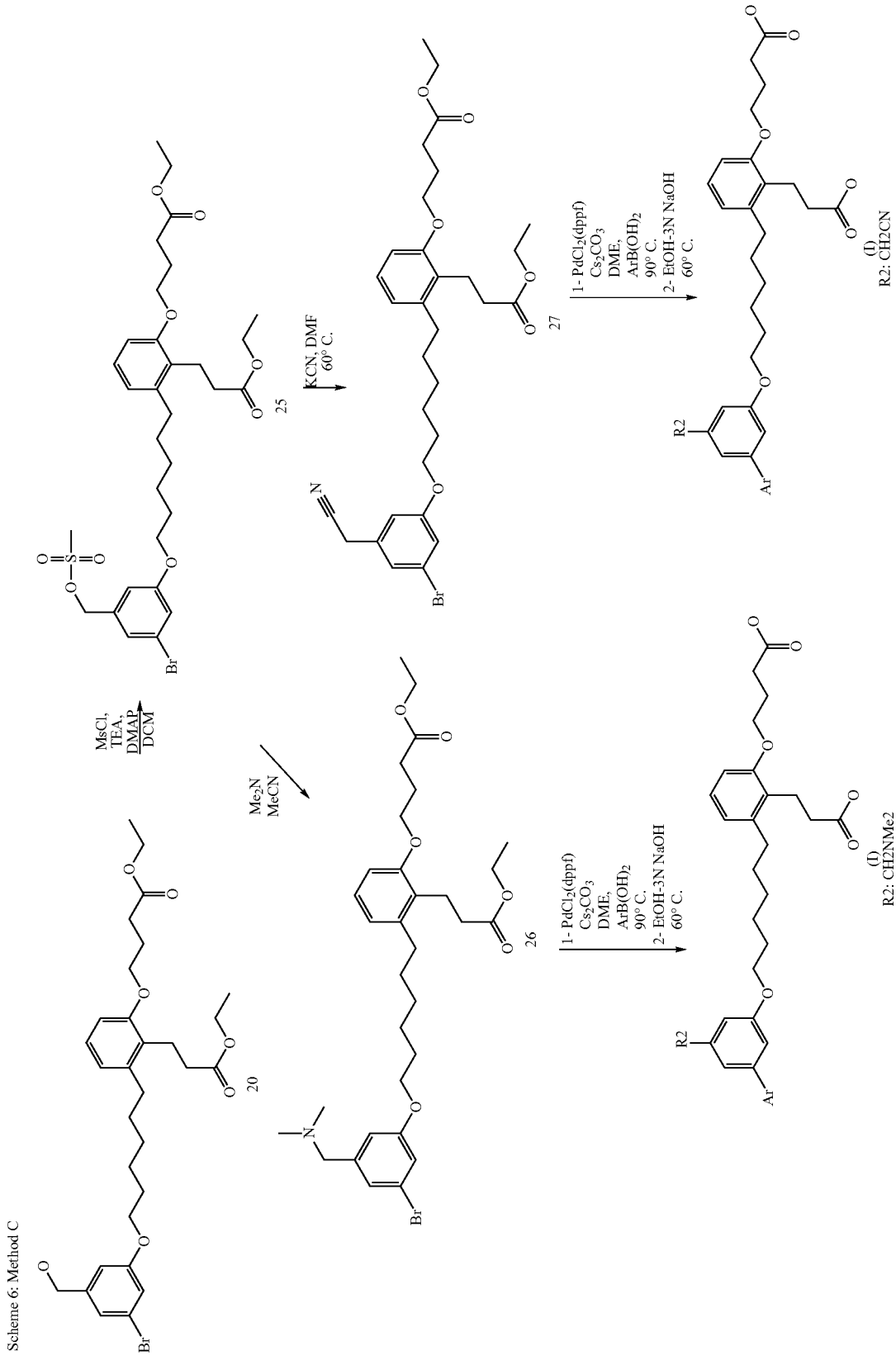

As shown in Scheme 6,3-N,N-dimethylaminomethyl-5-aryl analogues and 3-cyanomethyl-5-aryl analogues having a structure such as (I) can be prepared using Method C. The desired methanesulfonate 25 can be obtained from 3-hydroxymethyl analogue 20 by treatment with methanesulfonyl chloride, triethyl amine in dichloromethane and using a catalytic amount of N,N-dimethylaminopyridine. Then, the 3-N,N-dimethylaminomethyl-5-bromo analogue 26 was accomplished via a nucleophilic substitution reaction by treatment of 25 with N,N-dimethylamine in acetonitrile at room temperature. Alternatively, treatment of 25 with KCN in DMF at 60° C. afforded the desired 3-cyanomethyl-5-bromo analogue 27. The remaining two steps, Suzuki coupling with arylboronic acids and hydrolysis of the ethyl ester, were followed as described in Scheme 4 to obtain the final compounds such as (I).

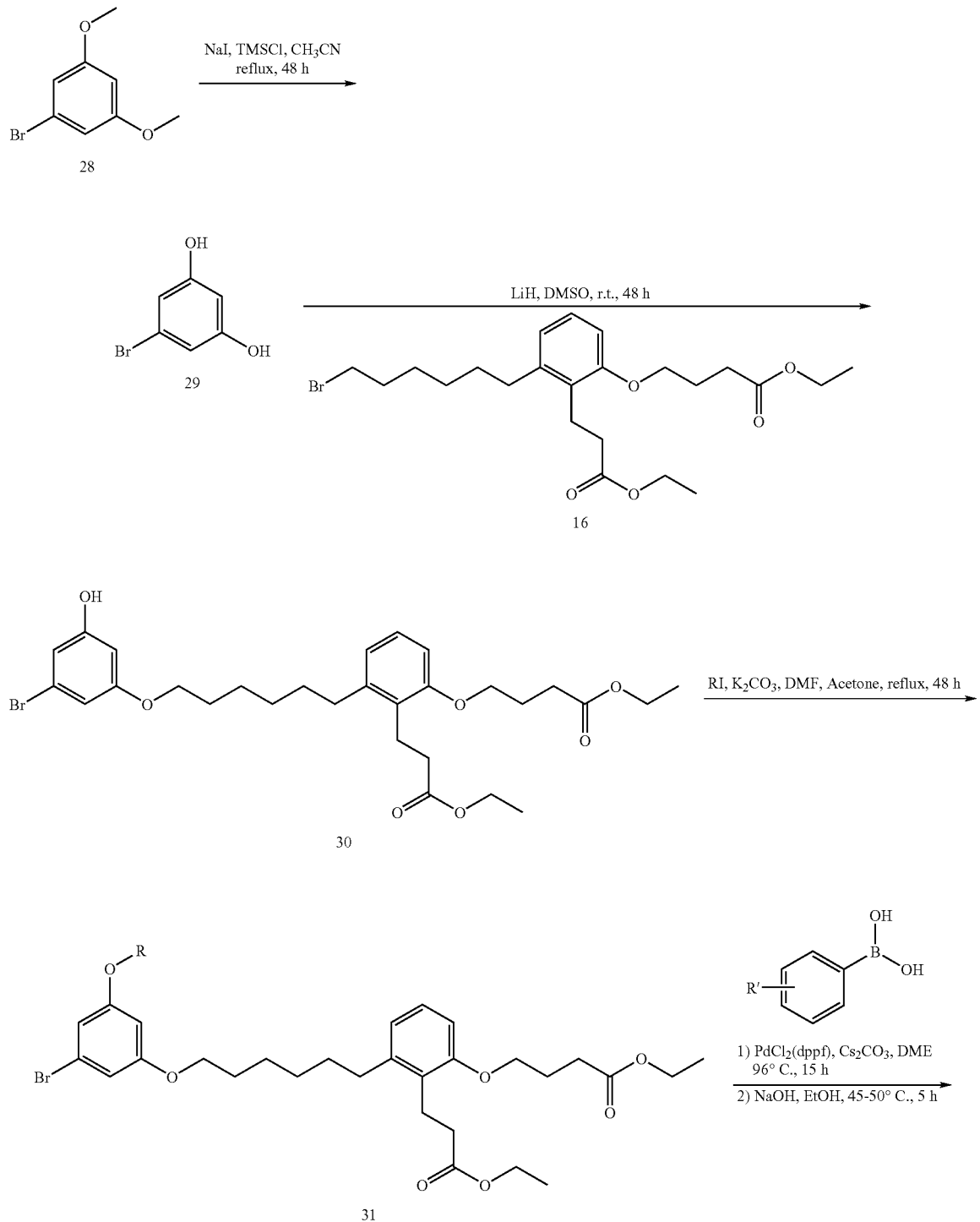

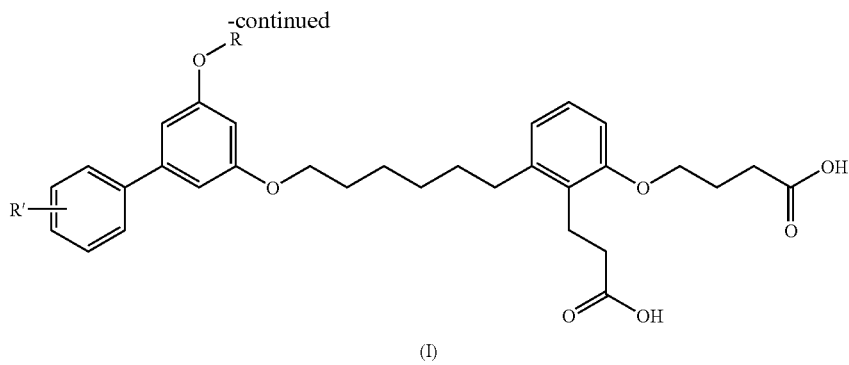

(I)

As shown in Scheme 7, 3-alkoxy-5-aryl analogues having a structure such as (I) can be prepared using Method D. The desired diol 29 can be obtained from commercially available 3,5-dimethoxy bromobenzene 28 by treatment with any dealkylating agent, such as trimethylchlorosilane and sodium iodide or tribromoborane in a solvent like acetonitrile or dichloromethane at reflux or room temperature. Then, the monoalkylation of one hydroxy of the diol 29 was accomplished by using lithium hydride and one equivalent of 16 in DMSO to give the desired compound 30. The second alkylation was accomplished by treatment of 30 with a lower alkyl iodide in the presence of a base such as potassium carbonate or cesium carbonate in a mixture of acetone and N,N-dimethylformamide at a temperature of about 75° C. The remaining two steps, Suzuki coupling with arylboronic acids and hydrolysis of the ethyl ester, were followed as described in the previous schemes to obtain the final compounds such as (I).

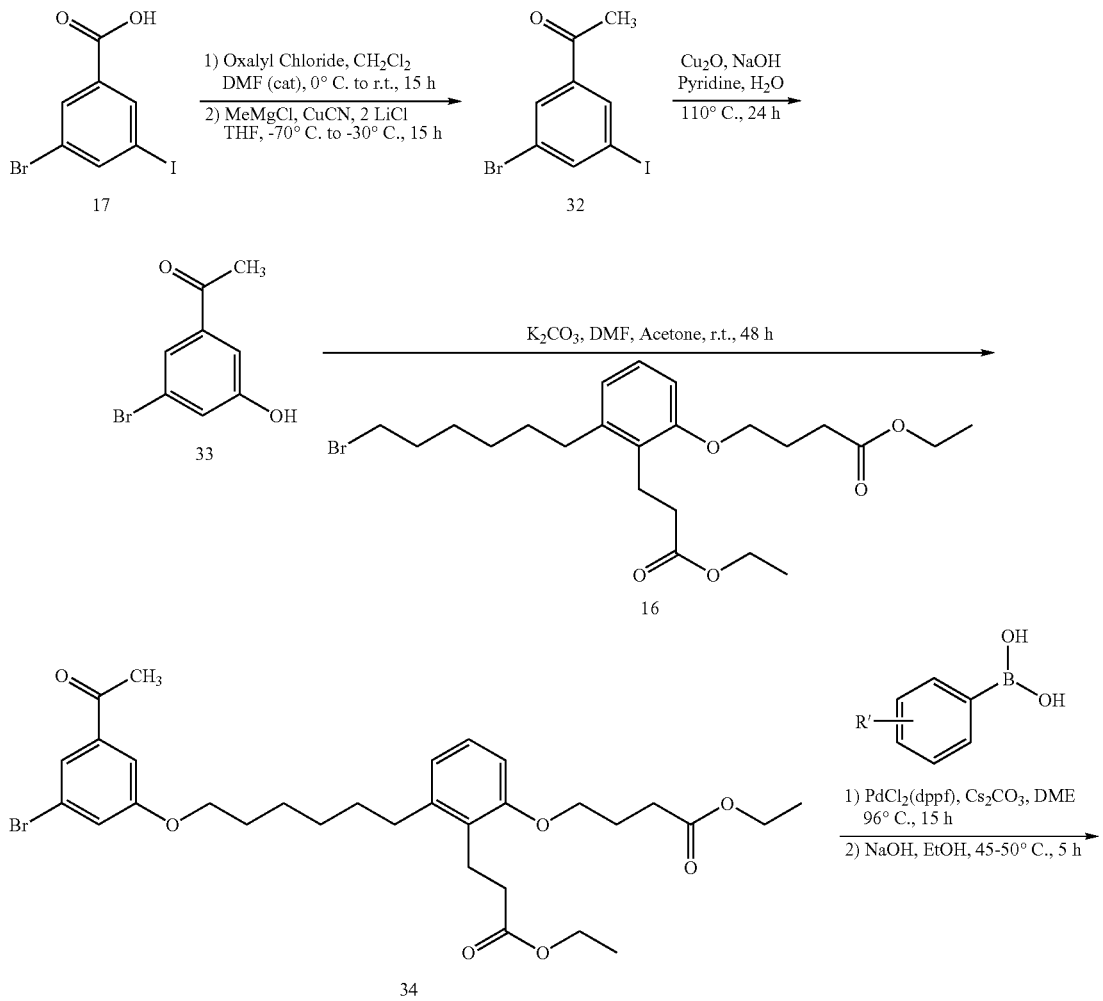

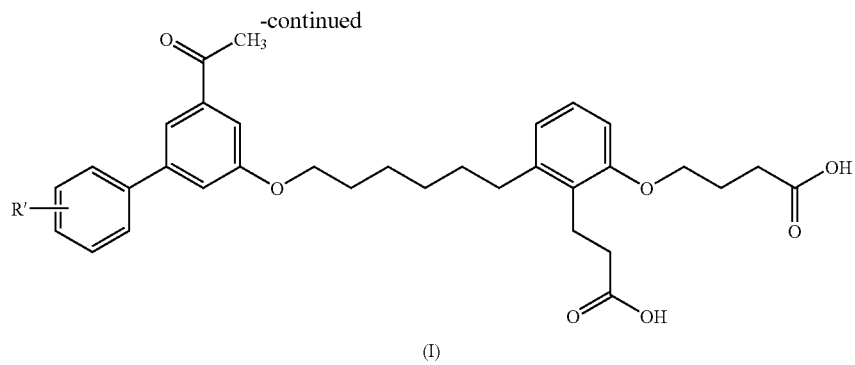
(I)

The target 3-acyl-5-aryl analogues (I) can be synthesized according to the Scheme 8, Method E. The desired 3-acyl-5-bromophenol 33 can be prepared from commercially available 3-bromo-5-iodobenzoic acid 17 in three steps. First, the 3-bromo-5-iodobenzoic acid 17 was converted to the corresponding acid chloride by treatment with oxalyl chloride in dichloromethane in the presence of a catalytic amount of N,N-dimethylformamide at 0° C. to room temperature. Then, the resulting acid chloride of 17 was treated with an in situ generated methylcopper reagent from methylmagnesium chloride and a soluble copper cyanide and lithium chloride mixture in tetrahydrofuran at −70 to −30° C. for 15 h to obtain 32 (Paul Knochel and Robert D. Singer, Chem. Rev. 1993, 93, 2117-2188. Finally, the iodide of 32 was converted to the corresponding phenol by treatment of 32 with sodium hydroxide in the presence of a catalytic amount of copper(I) oxide in water and pyridine at 110° C. to afford the desired 33. The remaining three steps, alkylation of phenol with 16, Suzuki coupling with arylboronic acids and hydrolysis of ethyl ester, were followed as described in the previous schemes to obtain the final 3-acyl-5-aryl analogues (I).

Scheme 9: Method F

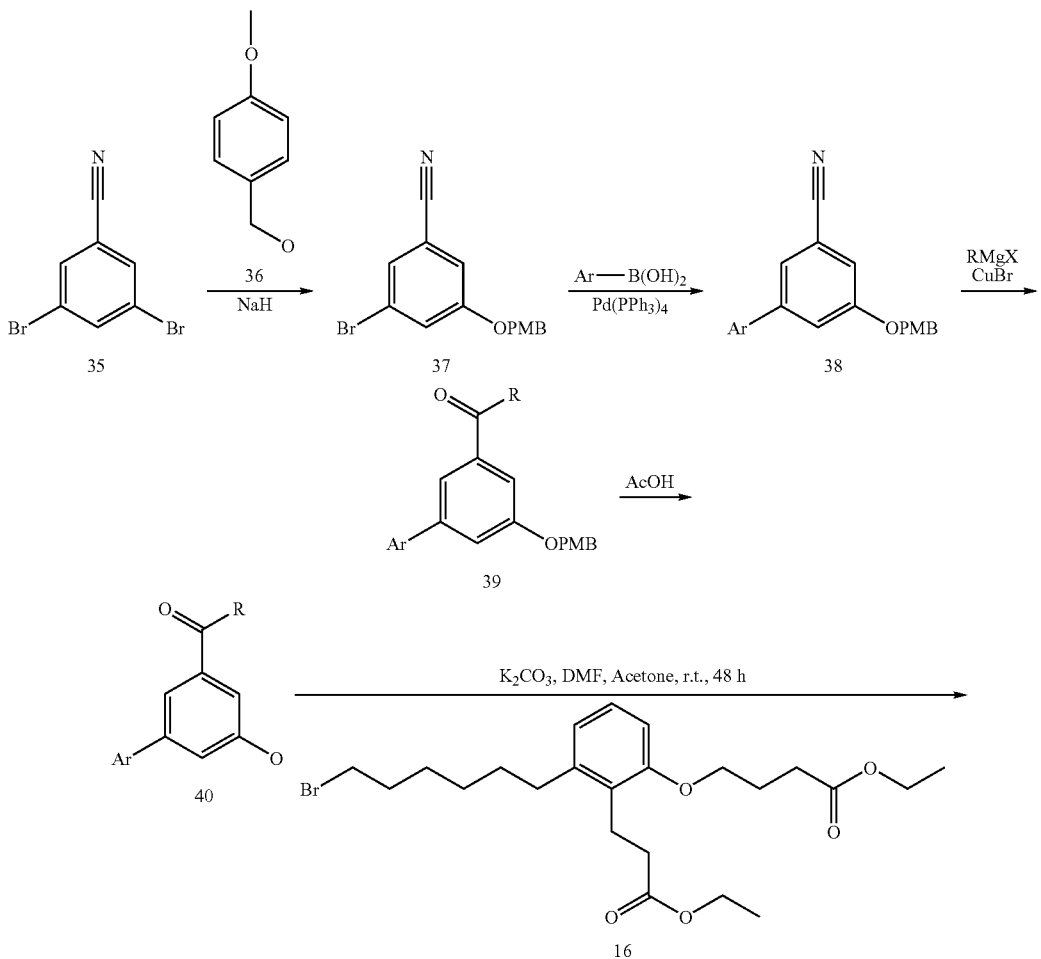

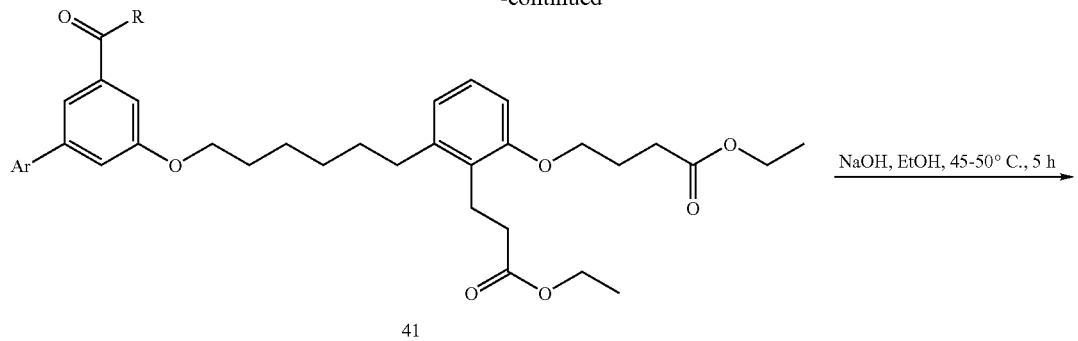

41

NaOH, EtOH, 45-50° C., 5 h →

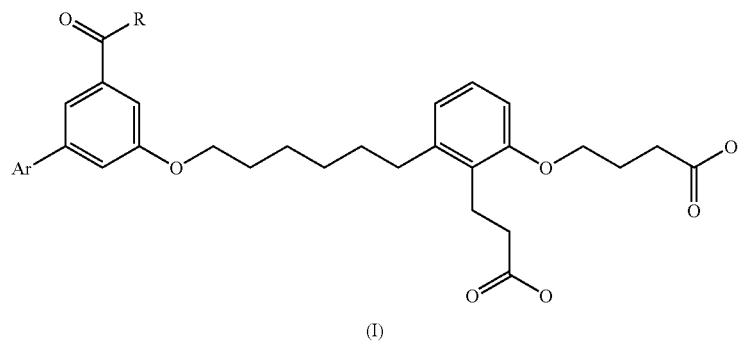

(I)

Compounds of Formula 40 can be conveniently prepared starting from 3,5-dibromobenzonitrile 35. The hydroxyl group can be introduced via a nucleophilic displacement of a bromine by an alkoxide, preferably para-methoxybenzyloxide, followed by ether cleavage to give a phenol. For example, para-methoxybenzyl group can be removed by refluxing in glacial acetic acid. Aryl group can be incorporated in a Suzuki coupling reaction between an appropriately substituted haloarene, preferably bromo- or iodoarene, and a boronic acid or a boronic acid equivalent (ester or anhydride) using a palladium catalyst. Nitrile group can be easily converted to ketone using a Grignard reagent and catalytic amount of cuprous bromide as described by Weiberth in *J. Org. Chem.* 1987, 52, 3901-3904.

Scheme 10: Method G

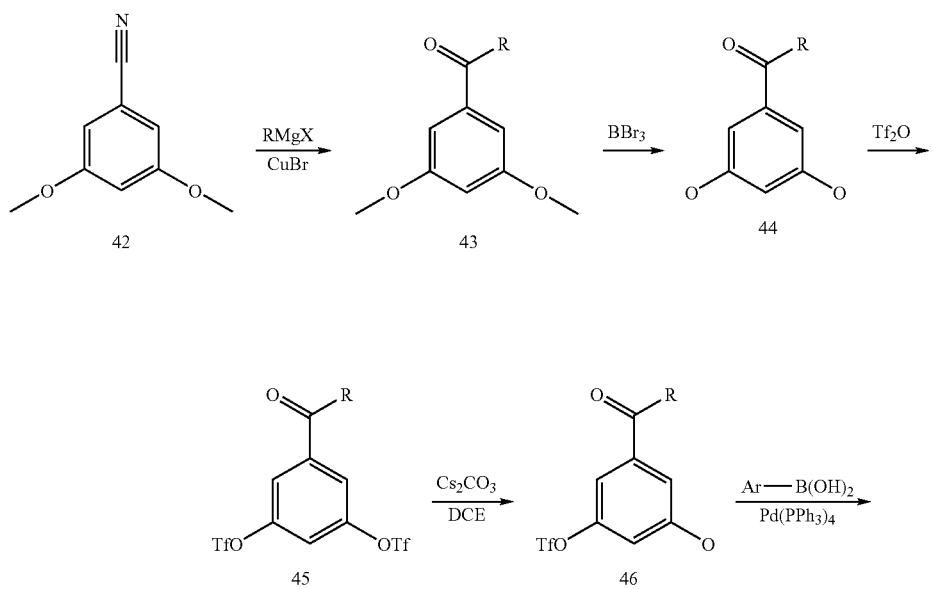

-continued

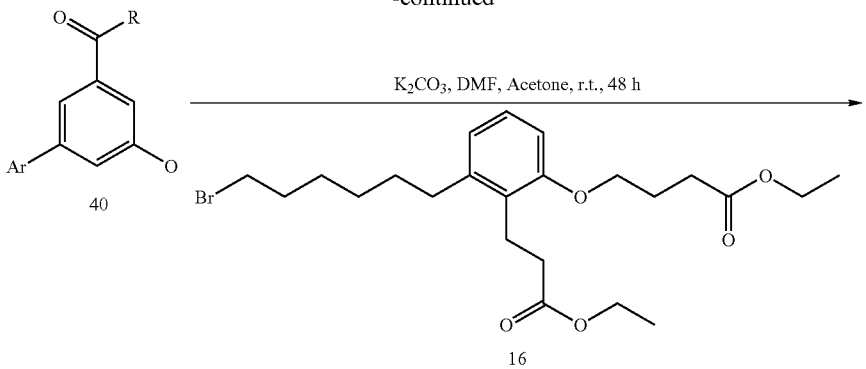

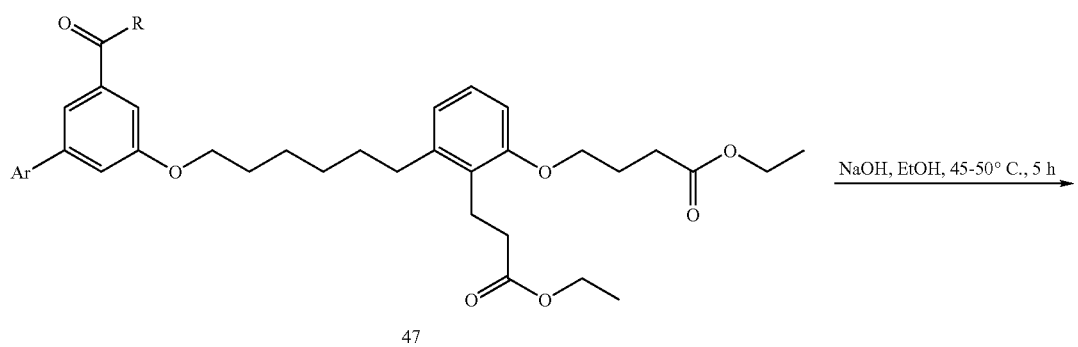

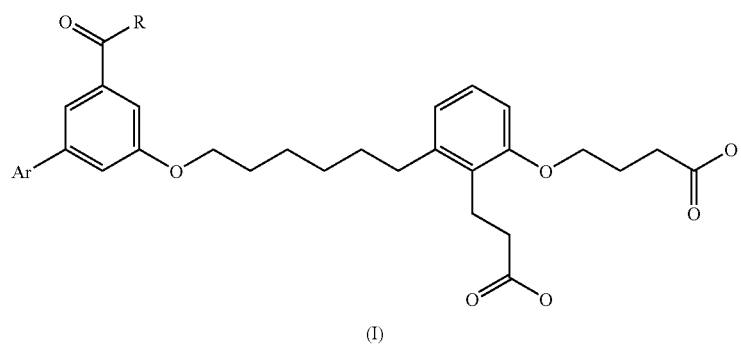

Compounds of Formula 47 can be prepared starting from 3,5-dimethoxybenzonitrile 42. Nitrile group can be easily converted to ketone using a Grignard reagent and catalytic amount of cuprous bromide as described by Weiberth in *J. Org. Chem.* 1987, 52, 3901-3904. The methoxy ether can be cleaved by methods known to those skilled in the art, preferably using boron tribromide yielding intermediate 44. Dihydroxy derivative 44 can be converted to monotriflate 46 in a two-step procedure: (i) conversion to the corresponding ditriflate 45 (Tf$_2$O, DIEA, CH$_2$Cl$_2$) and (ii) cleavage of one of the two sulfonyl groups by treatment with cesium carbonate in 1,2-dimethoxyethane as described by Hamura in *Helvetica Chimica Acta* 2002, 85, 3589-3605. Aryl group can be incorporated in a Suzuki coupling reaction between an appropriately substituted aromatic triflate and a boronic acid or a boronic acid equivalent using a palladium catalyst.

Scheme 11

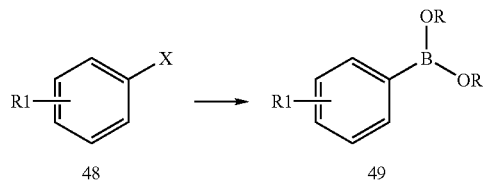

Substituted phenyl boronic acids (49, R═H) and boronic esters such as 4,4,5,5-tetramethyl-[1,3,2]dioxaborolane (49, R═—(C(CH$_3$)$_2$)$_2$—) useful in the preparation of compounds of this invention may be commercially available or they can be made by reactions that are well known in the field of organic synthesis. Aryl boronic acids and aryl boronic esters are formed by treatment of aryl halides 48 with an organometallic reagent such as n-butyl lithium followed by treatment with boron triisopropoxide or 4,4,4',4',5,5,5',5'-octamethyl-2,2'-bi-1,3,2-dioxaborolane followed by acidic workup as is well known to those skilled in the art (For example in the literature, see *Org. Process Res. Dev.* 2004, 8, 201).

Commercially available boronic acids used in this procedure are listed below. The Available Chemicals Database (ACD) indicates the availability of greater than seven hundred commercially available aryl boronic acids. Some boronic acids useful for the preparation of compounds of the invention are listed below.

TABLE 1

Commercially available boronic acids
Boronic acid

3-CHLORO-PHENYLBORONIC ACID
PHENYLBORONIC ACID
2-CHLOROPHENYLBORONIC ACID
3-CHLORO-4-FLUOROPHENYLBORONIC ACID
3-METHYLPHENYLBORONIC ACID
1,4-BENZODIOXANEBORONIC ACID
3,4-DIFLUOROPHENYLBORONIC ACID
4-CHLOROPHENYLBORONIC ACID
4-CHLORO-3-FLUOROPHENYLBORONIC ACID
THIOPHENE-2-BORONIC ACID
2-FLUOROPHENYLBORONIC ACID
4-FLUORO-3-METHYLPHENYLBORONIC ACID
3-FLUOROPHENYLBORONIC ACID
THIOPHENE-3-BORONIC ACID
4-METHYL-3-THIOPHENEBORONIC ACID
4-METHOXYPHENYLBORONIC ACID
4-ETHOXYPHENYLBORONIC ACID
3-FLUORO-4-METHYLPHENYLBORONIC ACID
4-ETHYLPHENYLBORONIC ACID
2,3-DIHYDROBENZOFURAN-5-BORONIC ACID
3-METHOXYPHENYLBORONIC ACID
2-TRIFLUOROMETHOXYPHENYLBORONIC ACID
4-TRIFLUOROMETHOXYPHENYLBORONIC ACID
4-FLUOROPHENYLBORONIC ACID
3-FLUORO-4-METHOXYPHENYLBORONIC ACID
3,5-DIFLUOROPHENYLBORONIC ACID
1-CYCLOHEXEN-1-YL-BORONIC ACID
5-BENZO[1,3]DIOXOLEBORONIC ACID
1H-PYRAZOLE-4-BORONIC ACID
1H-INDOLE-5-BORONIC ACID
4-PYRIDYL-BORONIC ACID
3-PYRIDYL-BORONIC ACID
4-METHANESULFONYLPHENYLBORONIC ACID
1-H-PYRAZOL-3-YLBORONIC ACID
4-FLUORO-3-HYDROXYPHENYLBORONIC ACID

TABLE 2

These boronic acids are also available from other suppliers that may not necessarily be listed in the ACD.

| | | |
|---|---|---|
| 3-Fluoro-6-(4,4,5,5-tetramethyl-[1,3,2]dioxaborolan-2-yl)pyridine | ATLANTIC SCIENTIFIC CO., INC., JERSEY CITY, NJ, | 791819-04-0 |
| Quinoline-2-boronic acid | LANCASTER | 745784-12-7 |
| 3-Chloro-6-(4,4,5,5-tetramethyl-[1,3,2]dioxaborolan-2-yl)pyridine | ATLANTIC SCIENTIFIC CO., INC., JERSEY CITY, NJ, | 652148-93-1 |
| 6-Chloropyridine-2-boronic acid pinacol ester | INTERCHIM, MONTLUCON, FRANCE | 652148-92-0 |
| Boronic acid, (2-methyl-4-pyrimidinyl)- | CHEMSTEP, TALENCE, FRANCE | 647853-31-4 |
| Boronic acid, (3-methoxy-2-pyridinyl)- | CHEMSTEP, TALENCE, FRANCE | 500707-34-6 |
| Boronic acid, (6-methoxy-2-pyridinyl)- | CHEMSTEP, TALENCE, FRANCE | 372963-51-4 |

TABLE 2-continued

These boronic acids are also available from other suppliers that may not necessarily be listed in the ACD.

| | | |
|---|---|---|
| Boronic acid, (6-methyl-2-pyridinyl)- | CHEMSTEP, TALENCE, FRANCE | 372963-50-3 |
| Boronic acid, (5-methyl-2-pyridinyl)- | CHEMSTEP, TALENCE, FRANCE | 372963-49-0 |
| Boronic acid, (4-methyl-2-pyridinyl)- | CHEMSTEP, TALENCE, FRANCE | 372963-48-9 |
| Boronic acid, 2-pyridinyl- | CHEMSTEP, TALENCE, FRANCE | 197958-29-5 |

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad lithium. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 1 to about 1000 mg per day.

The invention will now be further described in the Examples below, which are intended as an illustration only and do not limit the scope of the invention.

EXAMPLES

Reagents were purchased from Aldrich, Sigma, Maybridge, Advanced ChemTech, and Lancaster or other suppliers as indicated below and used without further purification. Reactions using microwave irradiation for heating were conducted using either a Personal Chemistry Emrys Optimizer System or a CEM Discovery System. The purification of multi-milligram to multi-gram scale was conducted by methods known know to those skilled in the art such as elution of silica gel flash column; preparative flash column purifications were also effected in some cases by use of disposal prepacked multigram silica gel columns (RediSep) eluted with a CombiFlash system. Biotage™ and ISCO™ are also flash column instruments that may have been used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3 u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Many compounds of Formula 1 were also purified by reversed phased HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap autoinjector. Compounds were collected from the elution stream using LC/MS detection in the positive ion detection: The elution of compounds from C-18 columns (2.0×10 cm eluting at 20 ml/min) was effected using appropriate linear gradation mode over 10 minutes of Solvent (A) 0.05% TFA/H2O and Solvent (B) 0.035% TFA/acetonitrile. For injection on to HPLC systems, the crude samples were dissolved in mixtures of methanol, acetonitrile and DMSO H-Cube™ (produced by Thales Nanotechnology) is a continuous-flow hydrogenation reactor equipped with in situ hydrogen generation and a disposable catalyst cartridge Cat-Cart™ The reaction mixture can be heated and pressurized up to 100° C. and 100 bar (1450 psi) respectively. Reaction scale can be varied from 10 mg to 100 g.

Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7T FT-Mass Spectrometer.

| | |
|---|---|
| AIBN | 2,2'-azobisisobutyronitrile, |
| Bu | butyl, |
| DCE | 1,2-dichloroethane, |
| DCM | dichloromethane, |
| DIPEA | diisopropylethylamine, |
| DMF | N,N-dimethylformamide, |
| DMSO | dimethylsulfoxide, |
| EtOAc | ethyl acetate, |
| EtOH | ethyl alcohol, |
| FCC | flash column chromatography, |
| h | hour, |
| HPLC | high pressure liquid chromatography, |
| HRMS | high resolution mass spectra, |
| LRMS | low resolutiom mass spectra, |
| LC | liquid chromatography, |
| L-Pro | L-proline, |
| MCPBA | meta-chloroperoxybenzoic acid, |
| MeOH | methyl alcohol, |
| MW | microwave, |
| NIS | N-iodosuccinimide, |
| NBS | N-bromosuccinimide, |
| NMP | 1-methyl-2-pyrrolidinone, |
| $PdCl_2$(dppf) | [1,1'-Bis(diphenylphosphino)ferrocene] dichloropalladium (II), |
| PG | protecting group, |
| PyBroP | bromo-tris-pyrrolidino-phosphonium hexafluorophosphate, |
| rt | room temperature, |
| TBAF | tetrabutylammonium fluoride, |
| TBDMS | tert-butyl-dimethylsilyl, |
| TBTU | 2-(1H-benzotriazole-1-y1)-1,1,3,3-tetramethyluronium tetrafluoroborate, |
| TMS | trimethylsilyl, |
| TMSSMe | (methylthio)trimethylsilane, |
| TEA | triethylamine, |
| TEMPO | 2,2,6,6-tetramethylpiperidine-1-oxyl, |
| TFA | trifluoroacetic acid, |
| THF | tetrahydrofuran. |

I. Preparation of Preferred Intermediates

Preparation of 4-[3-(6-bromo-hexyl)-2-(2-ethoxycarbonyl-ethyl)-phenoxy]-butyric acid ethyl ester 1) Preparation of 4-(2,3-dimethyl-phenoxy)-butyric acid ethyl ester

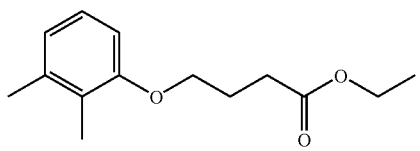

To a solution of 2,3-dimethylphenol (25 g, 204 mmol) in DMSO (205 mL) was added 4-bromo-butyric acid ethyl ester (40.96 g, 210 mmol) and lithium hydride (2.0 g, 250 mmol) at room temperature. The resulting light brown solution was stirred for 2 days. Then, the reaction mixture was cooled to 0° C. and water (200 mL) was added slowly. The organic compound was extracted into hexanes (2×200 mL). The combined organic extracts were washed with brine solution (150 mL)

and the organic solution was dried over anhydrous magnesium sulfate. Filtration of the drying agent and the removal of the solvent gave light brown oil. The crude mixture was purified by using a Biotage™ (40 L) column chromatography eluting with 5% ethyl acetate in hexanes to isolate 4-(2,3-dimethyl-phenoxy)-butyric acid ethyl ester (45.32 g, 94%) as a colorless oil: ES(+)-HRMS m/e calculated for $C_{14}H_{20}O_3$ (M+)$^+$ 236.1412. found 236.1419.

2) Preparation of 4-(2-formyl-3-methyl-phenoxy)-butyric acid ethyl ester

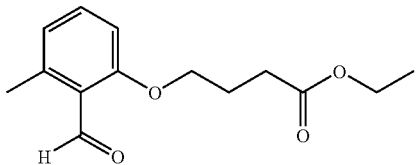

A mixture of copper(II) sulfate pentahydrate (21.98 g, 88.06 mmol) and potassium persulfate (71.42 g, 264 mmol) in water (396 mL) was heated to 63-65° C. to obtain a blue colored solution. Then, a solution of 4-(2,3-dimethyl-phenoxy)-butyric acid ethyl ester (20.81 g, 88.06 mmol) in acetonitrile (220 mL) was added at the above temperature. The resulting light green solution was refluxed for 40 minutes. Then, the reaction mixture was cooled to ~5° C. in order to precipitate most of the inorganic solids. The resulting solids were collected by filtration and the solid cake was washed with dichloromethane (1.0 L). The two layers of filtrate were separated and the aqueous layer was extracted with dichloromethane (200 mL). The combined organic extracts were washed with brine solution (150 mL) and the organic solution was dried over anhydrous magnesium sulfate. Filtration of the drying agent and the removal of the solvent gave a brown oil. The crude mixture was purified by using a Biotage™ (40 L) column chromatography eluting with 5-10% ethyl acetate in hexanes to obtain 4-(2-formyl-3-methyl-phenoxy)-butyric acid ethyl ester (45.32 g, 94%) as a colorless oil: EI(+)-HRMS m/e calculated for $C_{14}H_{18}O_4$ (M+)$^+$ 250.1205. found 250.1202.

3) Preparation of 4-[2((E)-2-ethoxycarbonyl-vinyl)-3-methyl-phenoxy]-butyric acid ethyl ester

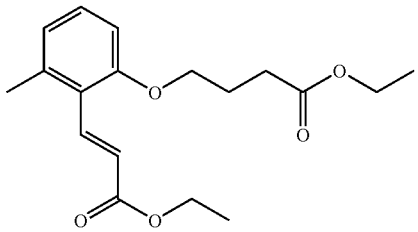

Sodium metal spheres (1.6 g, 69.6 mmol) were added to ethanol (100 mL) with stirring at room temperature under nitrogen atmosphere over 15 min. An exothermic reaction occurred and the mixture was stirred for another 15 min to form sodium ethoxide. After cooling to room temperature, triethylphosphonoacetate (14.7 mL, 73.4 mmol) and 4-(2-formyl-3-methyl-phenoxy)-butyric acid ethyl ester (13.25 g, 52.9 mmol) were added sequentially. During the addition of 4-(2-formyl-3-methyl-phenoxy)-butyric acid ethyl ester, the color of the solution turned brown and the temperature increased to ~55° C. The resulting brown solution was stirred for 2 days at room temperature. Then, the reaction mixture was diluted with water (150 mL) and stirred for 1 h. Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a light yellow oil. The crude oil was dissolved in hexanes (~50 mL) and treated with charcoal and heated gently with a heat gun. After cooling to room temperature, the charcoal was filtered-off and the filtrate was removed under vacuum to give 4-[2-((E)-2-ethoxycarbonyl-vinyl)-3-methyl-phenoxy]-butyric acid ethyl ester (13.25 g, 78%) as colorless oil: EI(+)-HRMS m/e calculated for $C_{18}H_{24}O_5$ (M+)$^+$ 320.1624. found 320.1626.

4) Preparation of 4-[3-bromomethyl-2-(E)-2-ethoxy-carbonyl-vinyl)-phenoxy]-butyric acid ethyl ester

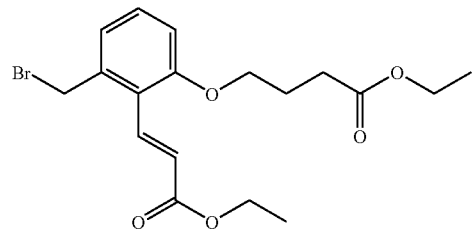

To a solution of 4-[2-((E)-2-ethoxycarbonyl-vinyl)-3-methyl-phenoxy]-butyric acid ethyl ester (8.0 g, 25.0 mmol) in chlorobenzene (190 mL) were added N-bromosuccinimide (6.67 g, 37.5 mmol) and 2,2'-azobisisobutyronitrile (AIBN) (591 mg, 3.6 mmol) at room temperature. Then, the solution was heated to 85° C. and stirred for 1 h. Then, the reaction mixture was cooled to room temperature and diluted with water (100 mL). Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a crude oil. The crude oil was purified by using a Biotage (40 L) column eluting with 15-25% ethyl acetate in hexanes to isolate 4-[3-bromomethyl-2-((E)-2-ethoxycarbonyl-vinyl)-phenoxy]-butyric acid ethyl ester (7.11 g, 71%) as a low melting solid: ES(+)-HRMS m/e calculated for $C_{18}H_{23}BrO_5$ (M+Na)$^+$ 421.0621, found 421.0621.

5) Preparation of 5-(tent-butyl-dimethyl-silanyloxy)-pentanal

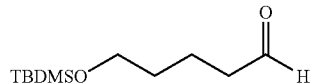

To a solution of 5-(tert-butyl-dimethyl-silanyloxy)-pentanol (16.8 mmol, 3.66 g) in dichloromethane (30 mL) were added water (5.6 mL), potassium bromide (1.7 mmol, 202 mg), n-tetrabutylammonium hydrogensulfate (0.84 mmol, 290 mg), and TEMPO (30 mg) at room temperature. The resulting light brown solution was cooled to ~5° C. and a solution of sodium hypochlorite (19.3 mmol, 30 mL, 5%) was added dropwise at this temperature. After addition of half of the sodium hypochlorite solution, solid potassium carbonate (300 mg) was added to maintain the reaction mixture basic. Then, the remaining sodium hypochlorite solution was added at 5-10° C. By this point, a precipitate had formed and the reaction mixture was stirred for another 1 h at ~10-15° C. Then, water (100 mL) was added and the resulting solution was extracted into diethyl ether (2×100 mL). The combined organic extracts were washed with brine solution (150 mL) and the organic layer was dried over anhydrous magnesium sulfate. Filtration of the drying agent and the removal of the solvent gave 5-(tert-butyl-dimethyl-silanyloxy)-pentanal (3.32 g, 91%) as a light brown oil: ES(+)-HRMS m/e calculated for $C_{11}H_{24}O_2Si$ (M+H)$^+$ 217.1619. found 217.1619.

6) Preparation of 4-[3-[6-(tert-butyl-dimethyl-silanyloxy)-hex-1-enyl]-2-((E)-2-ethoxycarbonyl-vinyl)-phenoxy]-butyric acid ethyl ester

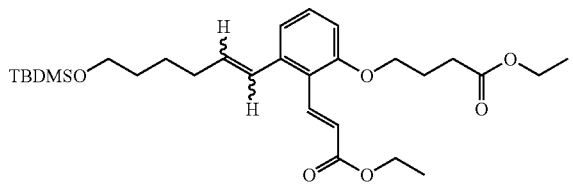

A solution of 4-[3-bromomethyl-2-((E)-2-ethoxycarbonyl-vinyl)-phenoxy]-butyric acid ethyl ester (2.0 mmol, 798 mg) and triphenylphosphine (2.2 mmol, 577 mg) in acetonitrile (12 mL) was heated to reflux for 1 h under nitrogen atmosphere. Then, it was cooled to room temperature and a solution of 5-(tert-butyl-dimethyl-silanyloxy)-pentanal (2.8 mmol, 606 mg) in 1,2-epoxybutane (22 mL) was added at room temperature and the mixture was again heated to reflux for 15 h. During this period, the mixture first turned to a brick red color and at the end of the reaction it had become a pale yellow solution. Then, the reaction mixture was cooled to room temperature and the solvent was removed under vacuum. The residue was dissolved in a solution of ethyl acetate and hexanes (1:3, 150 mL) and the resulting cloudy solution was washed with a mixture of methanol and water (2:1, 225 mL). The aqueous layer was extracted one more time with ethyl acetate and hexanes (1:3, 50 mL). The combined organic extracts were washed with brine solution (150 mL) and the organic solution was dried over anhydrous magnesium sulfate. Filtration of the drying agent and the removal of the solvent gave light brown oil. The crude mixture was purified by using a Biotage™ (40 L) column chromatograph eluting with 5 and 15% ethyl acetate in hexanes to obtain the desired 4-[3-[6-(tert-butyl-dimethyl-silanyloxy)-hex-1-enyl]-2-((E)-2-ethoxycarbonyl-vinyl)-phenoxy]-butyric acid ethyl ester (760 mg, 74%) as a colorless oil: ES(+)-HRMS m/e calculated for $C_{29}H_{46}O_6Si$ (M+Na)$^+$ 541.2956. found 541.2953.

7) Preparation of 4-[3-[6-(tert-butyl-dimethyl-silanyloxy)-hexyl]-2-(2-ethoxycarbonyl-ethyl)-phenoxy]-butyric acid ethyl ester

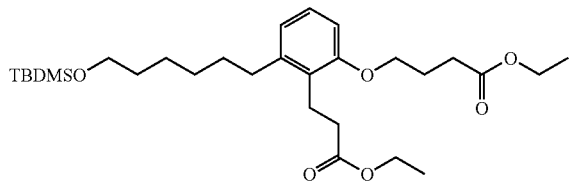

To a solution of 4-[3-[6-(tert-butyl-dimethyl-silanyloxy)-hex-1-enyl]-2-((E)-2-ethoxycarbonyl-vinyl)-phenoxy]-butyric acid ethyl ester (0.977 mmol, 507 mg) in ethyl acetate (10 mL) was added 10% palladium on carbon (350 mg) at room temperature. The resulting black mixture was stirred in the presence of atmospheric hydrogen gas in a balloon for 36 h at room temperature. Then, the catalyst was removed by filtration using a filter paper and the residue was washed with hot ethyl acetate (~60 mL). The filtrate was concentrated in vacuo and the resulting residue was dried under high vacuum to obtain 4-[3-[6-(tert-butyl-dimethyl-silanyloxy)-hexyl]-2-(2-ethoxycarbonyl-ethyl)-phenoxy]-butyric acid ethyl ester (438 mg, 86%) as a colorless oil: ES(+)-HRMS m/e calculated for $C_{29}H_{50}O_6Si$ (M+Na)$^+$ 545.3269. found 545.3267.

8) Preparation of 4-[2-(2-ethoxycarbonyl-ethyl)-3-(6-hydroxy-hexyl)-phenoxy]-butyric acid ethyl ester

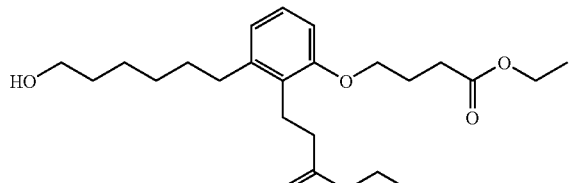

To a solution of 4-[3-[6-(tert-butyl-dimethyl-silanyloxy)-hexyl]-2-(2-ethoxycarbonyl-ethyl)-phenoxy]-butyric acid ethyl ester (0.837 mmol, 438 mg) in THF (12 mL) was added a solution of n-tetrabutyl ammonium fluoride (1.25 mmol, 1.25 mL, 1.0M) in THF at 0° C. Then, the resulting colorless solution was allowed to warm to room temperature in 2 h and the mixture was stirred for another 2 h at room temperature before being diluted with water (~50 mL). The organic compound was extracted into ethyl acetate (2×50 mL) and the combined extracts were washed with brine solution (100 mL). The organic solution was dried over anhydrous magnesium sulfate and the filtrate was removed under vacuum after filtration of the drying agent. The crude residue was dried further under high vacuum and the desired 4-[2-(2-ethoxycarbonyl-ethyl)-3-(6-hydroxy-hexyl)-phenoxy]-butyric acid ethyl ester (342 mg, 99%) was isolated as a colorless oil: ES(+)-HRMS m/e calculated for $C_{23}H_{36}O_6$ (M+Na)$^+$ 431.2404. found 431.2404.

9) Preparation of 4-[3-(6-bromo-hexyl)-2-(2-ethoxy-carbonyl-ethyl)-phenoxy]-butyric acid ethyl ester

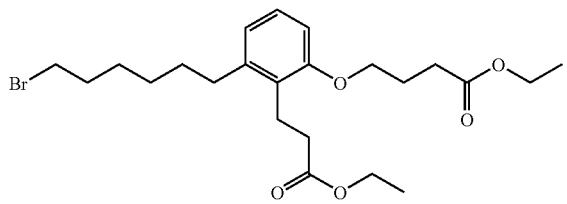

To a solution of 4-[2-(2-ethoxycarbonyl-ethyl)-3-(6-hydroxy-hexyl)-phenoxy]-butyric acid ethyl ester (0.85 mmol, 349 mg) and carbon tetrabromide (1.26 mmol, 423 mg) in dichloromethane (10 mL) was added triphenylphosphine (1.07 mmol, 281 mg) at ~0° C. The resulting colorless solution was stirred for 3 h at 5-10° C. Then, the solvent was removed under vacuum and the crude was tried to dissolve in a mixture of ethyl acetate and hexanes (1:3, 50 mL). As a result, a cloudy solution containing some precipitate was formed and the cloudy solution was transferred into a reparatory funnel and was washed with a mixture of methanol and water (2:1, 150 mL). The aqueous layer was extracted one more time with ethyl acetate and hexanes (1:3, 50 mL). The combined organic extracts were washed with brine solution (100 mL) and the organic solution was dried over anhydrous magnesium sulfate. Filtration of the drying agent and the removal of the solvent gave a colorless oil which was purified by using a Biotage™ (40M) column chromatography eluting with 10% ethyl acetate in hexanes to obtain the desired 4-[3-(6-bromo-hexyl)-2-(2-ethoxycarbonyl-ethyl)-phenoxy]-butyric acid ethyl ester (350 mg, 87.5%) as a colorless oil: ES(+)-HRMS m/e calculated for $C_{23}H_{35}BrO_5$ $(M+Na)^+$ 493.1560. found 493.1560.

II. Preparation of Preferred Compounds

Method A

Step 1: 3-Bromo-5-hydroxy-benzoic acid

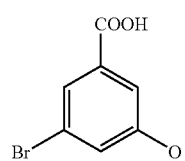

To a solution of NaOH (12.2 g; 305.8 mmol) in 300 mL of water was added 3-bromo-5-iodo-benzoic acid (20 g, 61.2 mmol) and $Cu_2O$ (866 mg, 6.1 mmol). The reaction mixture was heated at 100° C. for 24 h. After complete consumption of the starting material, the reaction mixture was cooled to room temperature and filtered through Celite™. The filtrate was then acidified with 10% aq. HCl and extracted into ethyl acetate. The organic extract was dried over anhydrous sodium sulfate and concentrated under reduced pressure to afford the title compound as a tan solid (12.3 g, 93% yield). HR-ES (−) calcd for $C_7H_5O_3Br$ $[M-H]^-$ 214.9349, observed 214.9350

Step 2: 3-Bromo-5-hydroxymethyl-phenol

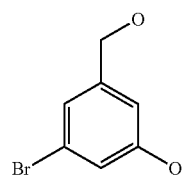

To a solution of 3-bromo-5-hydroxy-benzoic acid (5.0 g, 23.4 mmol) in 40 mL of THF was added a solution of 1M $LiAlH_4$ (30 mL), and the resulting solution was heated to reflux for 2 h. After cooling to room temperature, the reaction mixture was poured on ice and acidified with 10% aq. HCl. The solution was then filtered under vacuum and the filtrate was extracted with EtOAc. The organic extract was dried over anhydrous sodium sulfate and concentrated under reduced pressure. The crude material was purified by column chromatography (Isco™ 120 g) using 50% ethyl acetate/hexanes as eluting solvents to afford the title compound as a white solid (1.7 g, 36% yield). HR-ES(−) calcd for $C_7H_7O_2Br$ $[M-H]^-$ 200.9556, observed 200.9557.

Step 3: 4-[3-[6-(3-Bromo-5-hydroxymethyl-phenoxy)-hexyl]-2-(2-ethoxycarbonyl-ethyl)-phenoxy]-butyric acid ethyl ester

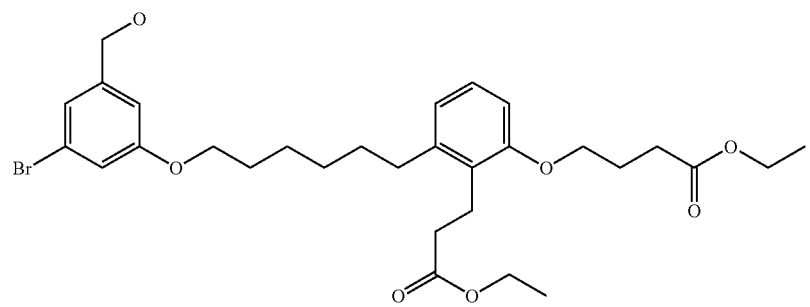

To a solution of 4-[3-(6-bromo-hexyl)-2-(2-ethoxycarbonyl-ethyl)-phenoxy]-butyric acid ethyl ester (4.2 g, 8.9 mmol), 3-Bromo-5-hydroxymethyl-phenol (1.5 g, 7.4 mmol) in N,N-dimethylformamide (40 mL) and acetone (80 mL) was added potassium carbonate (10.2 g, 74.2 mmol) at room temperature. The resulting suspension was heated to 70° C. for 24 h. Then, the reaction mixture was cooled to room temperature and diluted with water and 10% aq. HCl. The organic compound was extracted into ethyl acetate and the combined organic extracts were washed with water and brine solution. The organic layers were dried over anhydrous sodium sulfate and the solvent was removed under reduced pressure. The crude material was purified by column chromatography (Isco™ 120 g) with 0-50% ethyl acetate/hexanes as eluting solvents to afford the title compound (4.3 g, 99%) as a colorless oil. HR-ES(+) calcd for $C_{30}H_{41}O_7Br$ [M+Na]$^+$ 615.1928, observed 615.1926.

Step 4: 4-[3-[6-(3-Bromo-5-hydroxymethyl-phenoxy)-hexyl]-2-(2-carboxy-ethyl)-phenoxy]-butyric acid

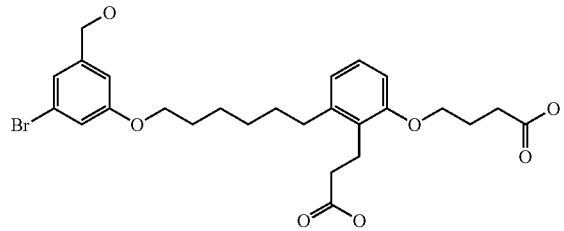

To a solution of 4-[3-[6-(3-Bromo-5-hydroxymethyl-phenoxy)-hexyl]-2-(2-ethoxycarbonyl-ethyl)-phenoxy]-butyric acid ethyl ester (1.0 g, 1.68 mmol) in hot ethanol (40 mL) was added aqueous 2.0 N sodium hydroxide (10 mL). The resulting solution was heated to 60° C. and stirred for 4 h. Then, the reaction mixture was cooled down and diluted with EtOAc, washed with 10% aq. HCl and brine. The combined ethyl acetate extracts were dried over anhydrous sodium sulfate and the solvent was removed under reduced pressure to afford 805 mg (89%) of title compound as a light yellow oil. HR-ES (+) calcd for $C_{26}H_{33}O_7Br$ [M+Na]$^+$ 559.1302, observed 559.1299.

Step 5: General Procedure for Suzuki Coupling

To a solution of 4-[3-[6-(3-bromo-5-hydroxymethyl-phenoxy)-hexyl]-2-(2-carboxy-ethyl)-phenoxy]-butyric acid (100 mg, 0.19 mmol), potassium carbonate (105 mg, 0.76 mmol), boronic acid (0.38 mmol) in EtOH (4 mL)/H$_2$O (1 mL) was added Pd(PPh$_3$)$_4$ (11 mg, 5 mol %). The reaction mixture was heated at 78° C. for 12 h, cooled down to room temperature then diluted with EtOAc. The resulting solution was washed with 10% aq. HCl and brine. The organic layer was then dried over anhydrous sodium sulfate and concentrated under vacuo to afford the crude material. The desired products were isolated by preparative HPLC.

Example 1

4-[3-[6-(3-Benzo[1,3]dioxol-5-yl-5-hydroxymethyl-phenoxy)-hexyl]-2-(2-carboxy-ethyl)-phenoxy]-butyric acid

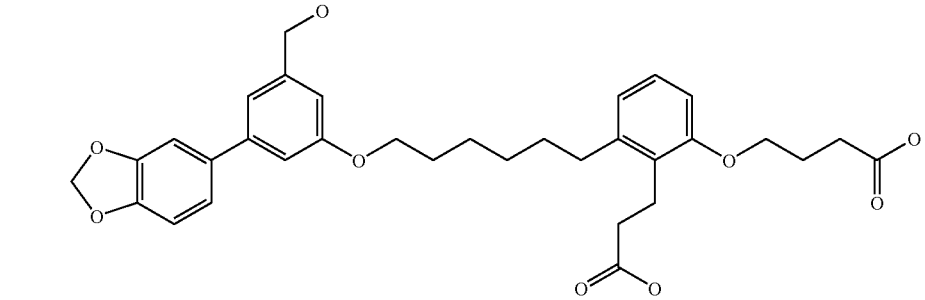

The title compound was prepared by following the general procedure for Suzuki coupling described above in Step 5 with 3,4-methylenedioxyphenyl boronic acid. HR-ES(+) calcd for $C_{33}H_{38}O_9$ (M+Na)$^+$ 601.2408. found 601.2407.

Example 2

4-{2-(2-Carboxy-ethyl)-3-[6-(5-hydroxymethyl-biphenyl-3-yloxy)-hexyl]-phenoxy}-butyric acid

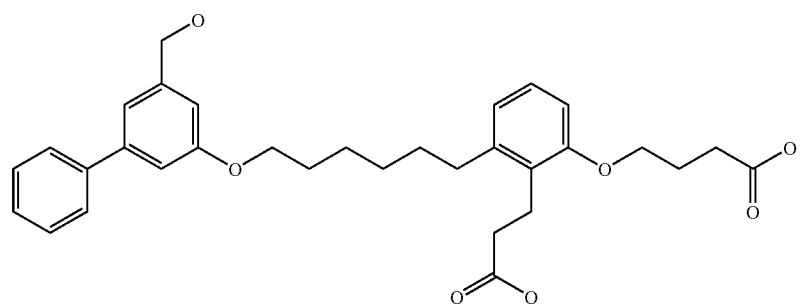

The title compound was prepared by following the general procedure for Suzuki coupling described above in Step 5 with phenylboronic acid. HR-ES(+) calcd for $C_{32}H_{38}O_7$ (M+H)$^+$ 535.2689. found 535.2689.

Example 3

4-{2-(2-Carboxy-ethyl)-3-[6-(3-hydroxymethyl-5-thiophen-3-yl-phenoxy)-hexyl]-phenoxy}-butyric acid

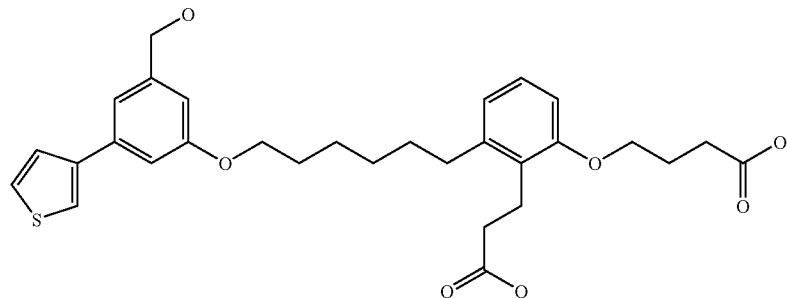

The title compound was prepared by following the general procedure for Suzuki coupling described above in Step 5 with 3-thiopheneboronic acid. HR-ES(+) calcd for $C_{30}H_{36}O_7S$ (M+Na)$^+$ 563.2074. found 563.2076.

Example 4

4-{2-(2-Carboxy-ethyl)-3-[6-(4'-fluoro-5-hydroxymethyl-biphenyl-3-yloxy)-hexyl]-phenoxy}-butyric acid

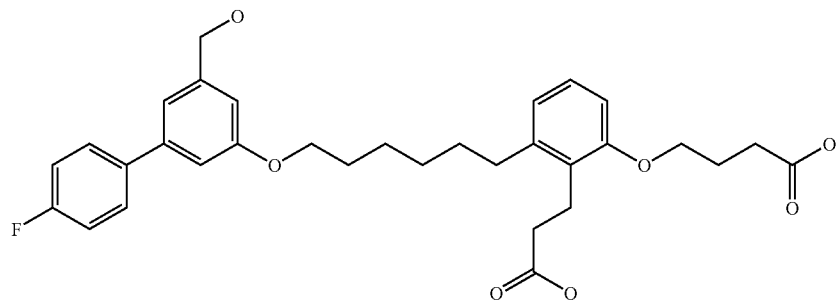

The title compound was prepared by following the general procedure for Suzuki coupling described above in Step 5 with 4-fluorophenylboronic acid. HR-ES(+) calcd for $C_{32}H_{37}O_7F$ (M+Na)$^+$ 575.2415. found 575.2413.

Example 5

4-{2-(2-Carboxy-ethyl)-3-[6-(4'-chloro-5-hydroxymethyl-biphenyl-3-yloxy)-hexyl]-phenoxy}-butyric acid

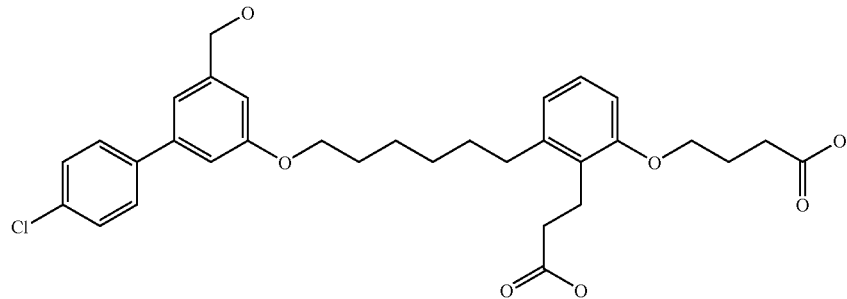

The title compound was prepared by following the general procedure for Suzuki coupling described above in Step 5 with 4-chlororophenylboronic acid. HR-ES(+) calcd for $C_{32}H_{37}O_7Cl$ (M+Na)$^+$ 591.2120. found 591.2121.

Example 6

4-(2-(2-Carboxy-ethyl)-3-{6-[3-(2,3-dihydro-benzo [1,4]dioxin-6-yl)-5-hydroxymethyl phenoxy]-hexyl}-phenoxy)-butyric acid

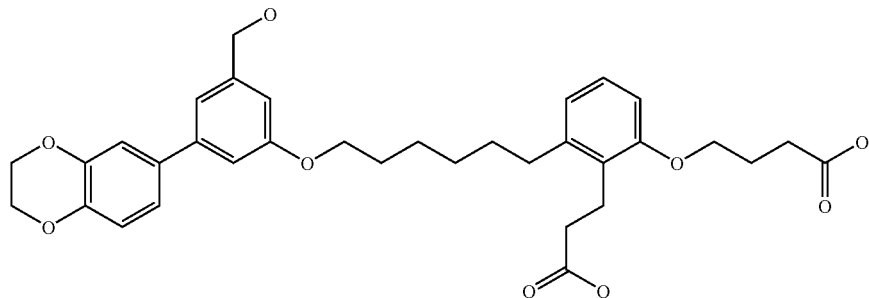

The title compound was prepared by following the general procedure for Suzuki coupling described above in Step 5 with 1,4-benzodioxane-6-boronic acid. HR-ES(+) calcd for $C_{34}H_{40}O_9Cl$ (M+Na)$^+$ 615.2564. found 615.2563.

Example 7

4-[2-(2-Carboxy-ethyl)-3-[6-(5-hydroxymethyl-4'-methanesulfonyl-biphenyl-3-yloxy)-hexyl]-phenoxy]-butyric acid

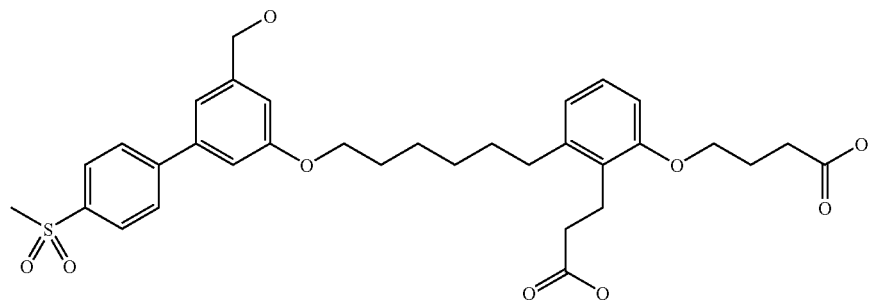

Step 1: 4-{2-(2-Ethoxycarbonyl-ethyl)-3-[6-(5-hydroxymethyl-4'-methanesulfonyl-biphenyl-3-yloxy)-hexyl]-phenoxy}-butyric acid ethyl ester

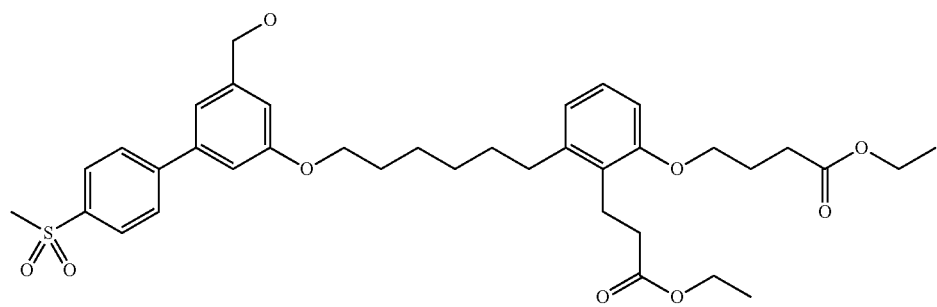

To a mixture of 4-[3-[6-(3-bromo-5-hydroxymethyl-phenoxy)-hexyl]-2-(2-ethyoxycarbonyl-ethyl)-phenoxy]-butyric acid ethyl ester (2.0 g, 3.34 mmol), 4-methanesulfonylphenylboronic acid (1.35 g, 6.74 mmol), [1,1'-bis(diphenylphosphino)ferrocene]dichloropalladium(II) (369.8 mg, 0.51 mmol), and cesium carbonate (2.22 g, 6.74 mmol) was added dimethoxyethane (100 mL) at room temperature under nitrogen atmosphere. The resulting brown reaction mixture was heated to 96° C. and stirred for 15 h at which time the TLC analysis of the reaction mixture indicated the absence of starting material. Then, the reaction mixture was cooled to room temperature and diluted with water and ethyl acetate. The two layers were separated and the aqueous layer was extracted with ethyl acetate and the combined organic extracts were washed with water and brine solution. The organic layer was dried over anhydrous magnesium sulfate and filtration of the drying agent and removal of the solvent under vacuum gave the colored residue which was purified by using an ISCO 120 g column to obtain 4-{2-(2-ethoxycarbonyl-ethyl)-3-[6-(5-hydroxymethyl-4'-methanesulfonyl-biphenyl-3-yloxy)-hexyl]-phenoxy}-butyric acid ethyl ester (1.23 g, 55%) as a light brown oil: ES(+)-HRMS m/e calcd for $C_{37}H_{48}O_9S$ (M+Na)$^+$ 691.2911. found 691.2913.

Step 2: 4-[2-(2-Carboxy-ethyl)-3-[6-(5-hydroxymethyl-4'-methanesulfonyl-biphenyl-3-yloxy)-hexyl]phenoxy]-butyric acid

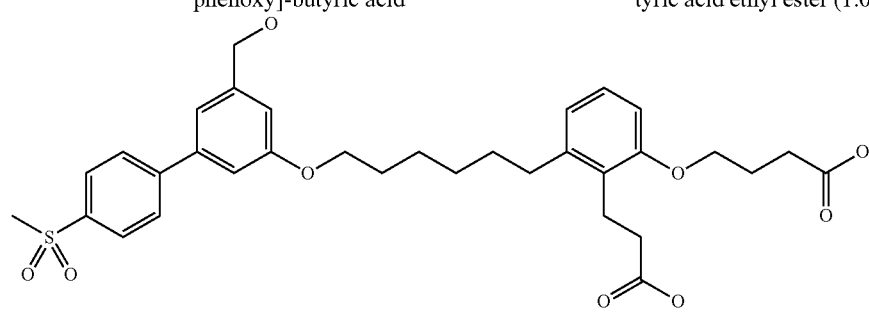

To a solution of the 4-{2-(2-ethoxycarbonyl-ethyl)-3-[6-(5-hydroxymethyl-4'-methanesulfonyl-biphenyl-3-yloxy)-hexyl]-phenoxy}-butyric acid ethyl ester (250 mg, 0.37 mmol) in THF (5 mL) and ethanol (5 mL) was added aqueous 1.0 N sodium hydroxide (4 mL) at room temperature. The resulting suspension was stirred for 5 h at room temperature at which time TLC analysis of the mixture indicated the absence of starting material. Then, the reaction mixture was concentrated and the residue was diluted with water (20 mL) and extracted with diethyl ether (30 mL) to remove any neutral impurities. The aqueous layer was acidified with 1.0 N hydrochloric acid and the precipitated white organic compound was extracted into ethyl acetate (2×30 mL). The combined ethyl acetate extracts were washed with brine solution (50 mL) and the organic layers were dried over anhydrous magnesium sulfate. Filtration of the drying agent and removal of the solvent afforded 4-[2-(2-carboxy-ethyl)-3-[6-(5-hydroxymethyl-4'-methanesulfonyl-biphenyl-3-yloxy)-hexyl]-phenoxy]-butyric acid (65 mg, 37%) as a white solid: ES(+)-HRMS m/e calcd for $C_{33}H_{40}O_9S$ (M+Na)$^+$ 635.2285. found 635.2284.

Method B

Step 1: 4-[3-[6-(3-Bromo-5-methoxymethyl-phenoxy)-hexyl]-2-(2-ethoxycarbonyl-ethyl)-phenoxy]-butyric acid ethyl ester

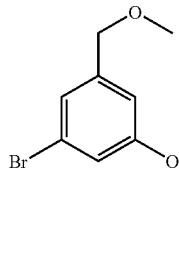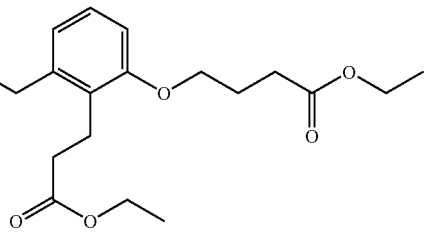

To a solution of 4-[3-[6-(3-bromo-5-hydroxymethyl-phenoxy)-hexyl]-2-(2-ethoxycarbonyl-ethyl)-phenoxy]-butyric acid ethyl ester (1.25 g, 2.1 mmol) in DMF (25 mL) were added sodium hydride (211 mg, 5.26 mmol) and iodomethane (747 mg, 5.26 mmol) at room temperature. The resulting suspension was stirred for 15 h and then the excess sodium hydride was quenched by slow addition of water (5 mL). The mixture was diluted with 1.0N hydrochloric acid (50 mL) and the organic compound was extracted into ethyl acetate (2×50 mL). The combined extracts were washed with brine solution (100 mL) and dried over anhydrous magnesium sulfate. Filtration of the drying agent and removal of the solvent under vacuum afforded the crude residue which was purified by using an ISCO 40 g column, eluting with 0-30% ethyl acetate in hexanes to obtain 4-[3-[6-(3-bromo-5-methoxymethyl-phenoxy)-hexyl]-2-(2-ethoxycarbonyl-ethyl)-phenoxy]-butyric acid ethyl ester (1.03 g, 81%) as a colorless viscous oil: EI(+)-HRMS m/e calcd for $C_{31}H_{43}BrO_7$ (M+Na)$^+$ 629.2084. found 629.2085.

Step 2: 4-[3-[6-(3-Bromo-5-methoxymethyl-phenoxy)-hexyl]-2-(2-carboxy-ethyl)-phenoxy]-butyric acid

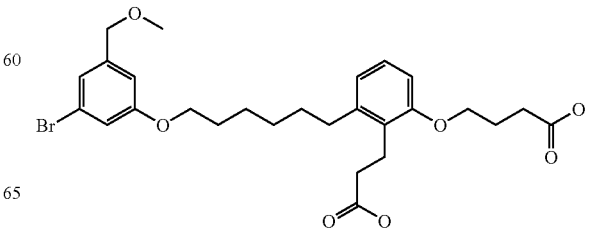

To a solution of 4-[3-[6-(3-Bromo-5-methoxymethyl-phenoxy)-hexyl]-2-(2-ethoxycarbonyl-ethyl)-phenoxy]-butyric acid ethyl ester (500 mg, 0.82 mmol) in hot ethanol (20 mL) was added aqueous 2.0 N sodium hydroxide (5 mL). The resulting solution was heated to 60° C. and stirred for 4 h. Then, the reaction mixture was cooled down and diluted with EtOAc, washed with 10% aq. HCl and brine. The combined ethyl acetate extracts were dried over anhydrous sodium sulfate and the solvent was removed under reduced pressure to afford 400 mg (89%) of title compound as a light yellow oil. HR-ES(+) calcd for $C_{27}H_{35}O_7Br$ $[M+Na]^+$ 573.1458, observed 573.1459.

Step 3: General Procedure for Suzuki Coupling

Method A:

To a solution of 4-[3-[6-(3-Bromo-5-methoxymethyl-phenoxy)-hexyl]-2-(2-carboxy-ethyl)-phenoxy]-butyric acid (100 mg, 0.19 mmol), potassium carbonate (105 mg, 0.76 mmol), boronic acid (0.38 mmol) in EtOH (4 mL)/$H_2O$ (1 mL) was added $Pd(PPh_3)_4$ (11 mg, 5 mol %). The reaction mixture was heated at 78° C. for 12 h, cooled down to room temperature then diluted with EtOAc. The resulting solution was washed with 10% aq. HCl and brine. The organic layer was then dried over anhydrous sodium sulfate and concentrated under vacuo to afford the crude material. The desired products were isolated by preparative HPLC.

Method B:

To a mixture of 4-[3-[6-(3-bromo-5-ethoxy-phenoxy)-hexyl]-2-(2-ethoxycarbonyl-ethyl)-phenoxy]-butyric acid ethyl ester, boronic acid [1,1'-bis(diphenylphosphino)ferrocene]dichloropalladium(II), and cesium carbonate was added dimethoxyethane (10 mL) at room temperature under nitrogen atmosphere. The resulting brown reaction mixture was heated to 96° C. and stirred for 15 h at which time the TLC analysis of the reaction mixture indicated the absence of starting material. Then, the reaction mixture was cooled to room temperature and diluted with water (50 mL) and ethyl acetate (50 mL). The two layers were separated and the aqueous layer was extracted with ethyl acetate (50 mL) and the combined organic extracts were washed with water (50 mL) and brine solution (50 mL). The organic layer was dried over anhydrous magnesium sulfate and filtration of the drying agent and removal of the solvent under vacuum gave the colored residue which was purified by using an ISCO 40 column. eluting with 0-25% ethyl acetate in hexanes to obtain the desired product.

Example 8

4-[3-[6-(3-Benzo[1,3]dioxol-5-yl-5-methoxymethyl-phenoxy)-hexyl]-2-(2-carboxy-ethyl)-phenoxy]-butyric acid

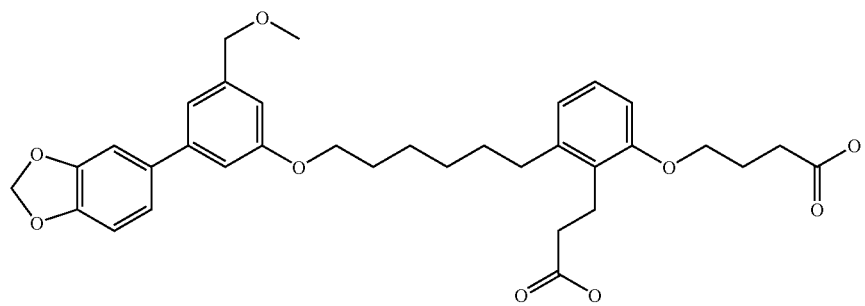

The title compound was prepared by following the general procedure for Suzuki coupling described above in step 3 using method A with 3,4-methylenedioxyphenyl boronic acid. HR-ES(+) calcd for $C_{34}H_{40}O_9$ $(M+Na)^+$ 615.2564. found 615.2564.

Example 9

4-{2-(2-Carboxy-ethyl)-3-[6-(5-methoxymethyl-biphenyl-3-yloxy)-hexyl]-phenoxy}-butyric acid

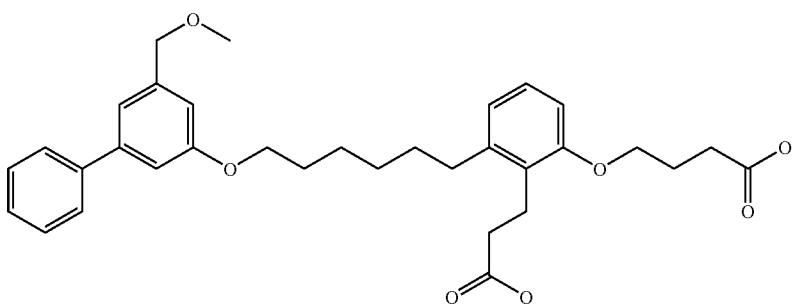

The title compound was prepared by following the general procedure for Suzuki coupling described above in step 3 using method A with phenylboronic acid. HR-ES(+) calcd for $C_{33}H_{40}O_7$ $(M+Na)^+$ 571.2666. found 571.2665.

Example 10

4-{2-(2-Carboxy-ethyl)-3-[6-(4'-fluoro-5-methoxymethyl-biphenyl-3-yloxy)-hexyl]-phenoxy}-butyric acid

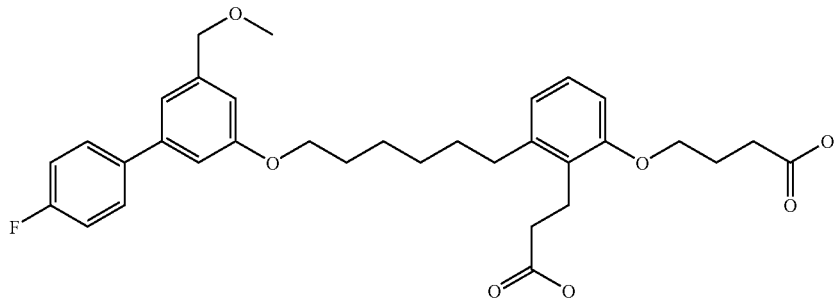

The title compound was prepared by following the general procedure for Suzuki coupling described above in step 3 using method A with 4-fluorophenylboronic acid. HR-ES(+) calcd for $C_{33}H_{39}O_7F$ (M+Na)$^+$ 589.2572. found 589.2574.

Example 11

4-{2-(2-Carboxy-ethyl)-3-[6-(4'-chloro-5-methoxymethyl-biphenyl-3-yloxy)-hexyl]-phenoxy}-butyric acid

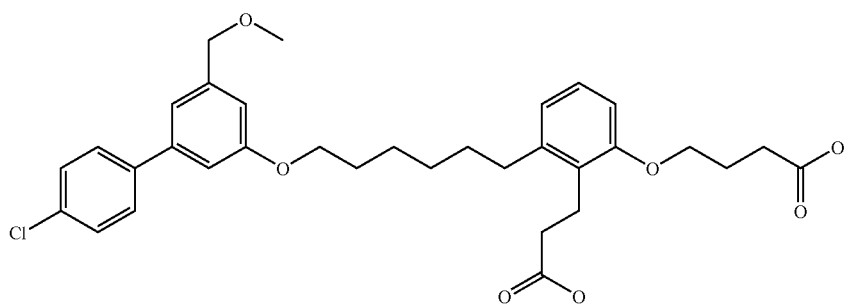

The title compound was prepared by following the general procedure for Suzuki coupling described above in step 3 using method A with 4-chlorophenylboronic acid. HR-ES(+) calcd for $C_{33}H_{39}O_7Cl$ (M+Na)$^+$ 605.2276. found 605.2279.

Example 12

4-(2-(2-Carboxy-ethyl)-3-{6-[3-(2,3-dihydro-benzo[1,4]dioxin-6-yl)-5-methoxy methyl-phenoxy]-hexyl}-phenoxy)-butyric acid

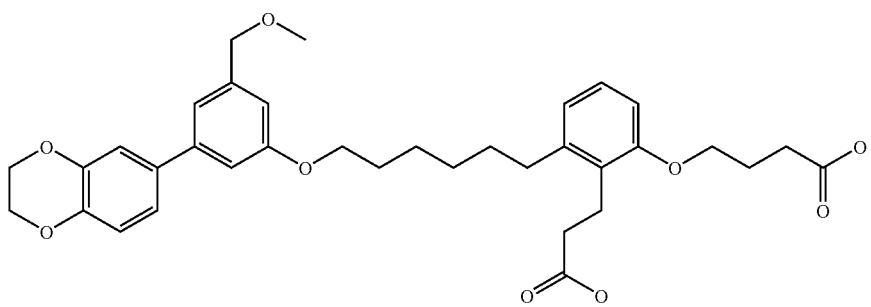

The title compound was prepared by following the general procedure for Suzuki coupling described above in step 3 using method A with 1,4-benzodioxane-6-boronic acid. HR-ES(+) calcd for $C_{35}H_{42}O_9$ (M+Na)$^+$ 629.2721. found 629.2719.

Example 13

4-(2-(2-Carboxy-ethyl)-3-{6-[3-methoxymethyl-5-(4-methyl-thiophen-3-yl)-phenoxy]-hexyl}-phenoxy)-butyric acid

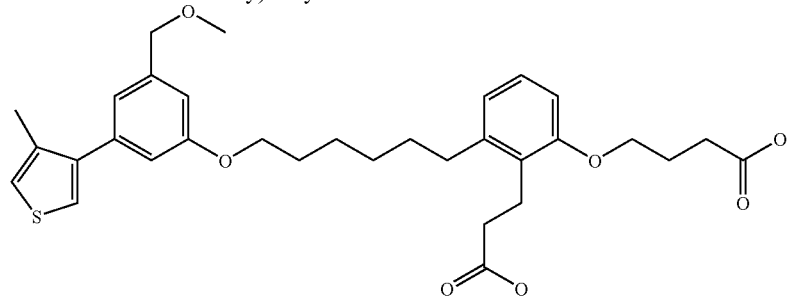

The title compound was prepared by following the general procedure for Suzuki coupling described above in step 3 using method A with 4-methyl-3-thiopheneboronic acid. HR-ES(+) calcd for $C_{32}H_{40}O_7S$ (M+Na)$^+$ 591.2387. found 591.2387.

Example 14

4-{2-(2-Carboxy-ethyl)-3-[6-(3'-fluoro-5-methoxymethyl-biphenyl-3-yloxy)-hexyl]-phenoxy}-butyric acid

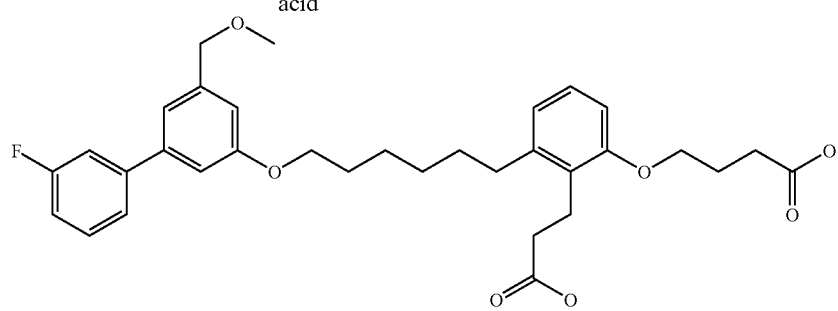

The title compound was prepared by following the general procedure for Suzuki coupling described above in step 3 using method A with 3-fluorophenylboronic acid. HR-ES(+) calcd for $C_{33}H_{39}O_7F$ (M+Na)$^+$ 589.2572. found 589.2571.

Example 15

4-{2-(2-Carboxy-ethyl)-3-[6-(2'-fluoro-5-methoxymethyl-biphenyl-3-yloxy)-hexyl]-phenoxy}-butyric acid

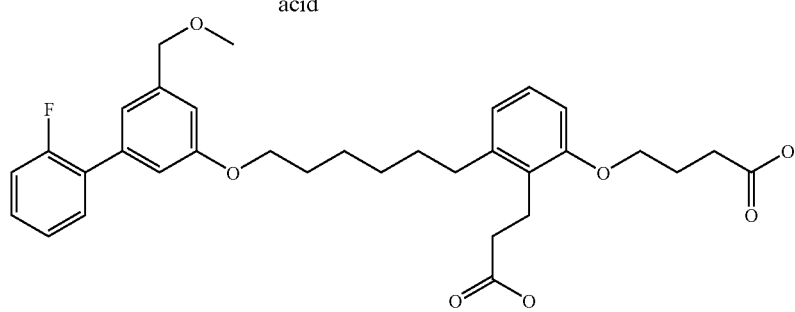

The title compound was prepared by following the general procedure for Suzuki coupling described above in step 3 using method A with 2-fluorophenylboronic acid. HR-ES(+) calcd for $C_{33}H_{39}O_7F$ $(M+Na)^+$ 589.2572. found 589.2573.

Example 16

4-{2-(2-Carboxy-ethyl)-3-[6-(3',5'-difluoro-5-methoxymethyl-biphenyl-3-yloxy)-hexyl]-phenoxy}-butyric acid

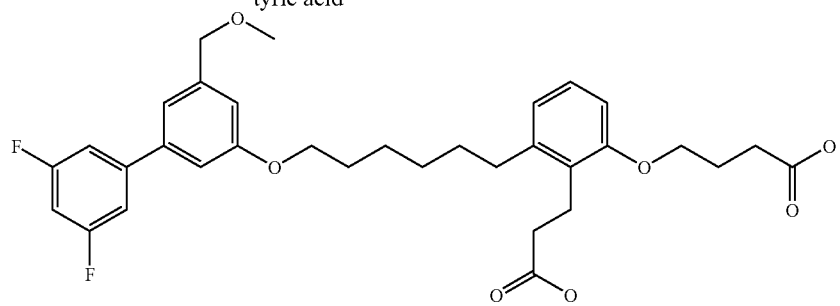

The title compound was prepared by following the general procedure for Suzuki coupling described above in step 3 using method A with 3,5-difluorophenylboronic acid. HR-ES(+) calcd for $C_{33}H_{38}O_7F_2$ $(M+Na)^+$ 607.2478. found 607.2474.

Example 17

4-{2-(2-Carboxy-ethyl)-3-[6-(5-methoxymethyl-4'-trifluoromethyl-biphenyl-3-yloxy)-hexyl]-phenoxy}-butyric acid

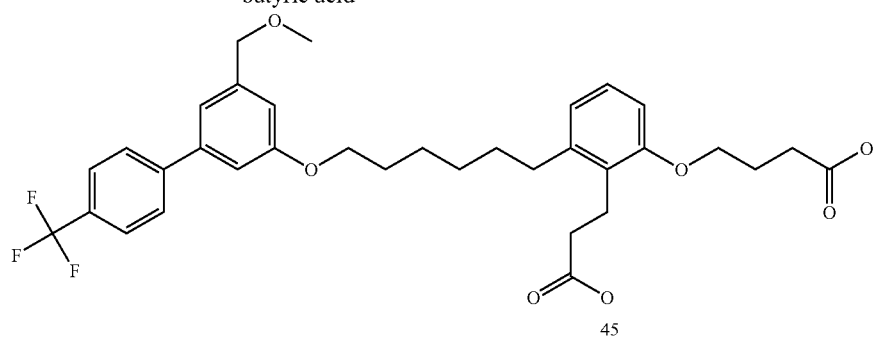

The title compound was prepared by following the general procedure for Suzuki coupling described above in step 3 using method A with 4-trifluoromethylphenylboronic acid. HR-ES(+) calcd for $C_{34}H_{39}O_7F_3$ $(M+Na)^+$ 639.2540. found 639.2537.

Example 18

4-{2-(2-Carboxy-ethyl)-3-[6-(3'-chloro-5-methoxymethyl-biphenyl-3-yloxy)-hexyl]-phenoxy}-butyric acid

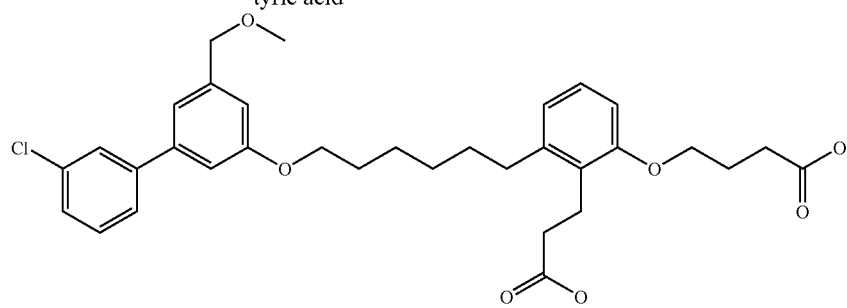

The title compound was prepared by following the general procedure for Suzuki coupling described above in step 3 using method A with 3-chlorophenylboronic acid. HR-ES(+) calcd for $C_{33}H_{39}O_7Cl$ (M+Na)$^+$ 605.2276. found 605.2279.

Example 19

4-{2-(2-Carboxy-ethyl)-3-[6-(3'-methoxy-5-methoxymethyl-biphenyl-3-yloxy)-hexyl]-phenoxy}-butyric acid

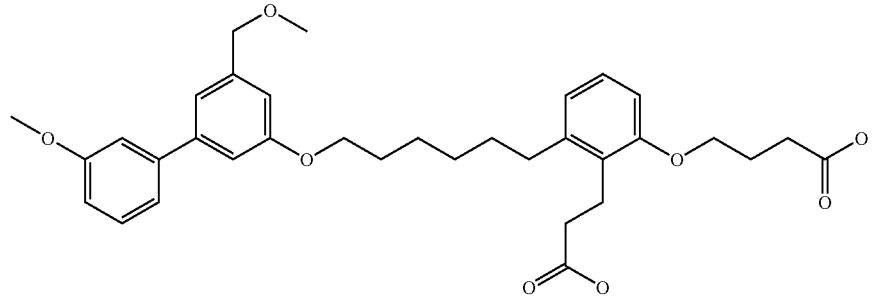

The title compound was prepared by following the general procedure for Suzuki coupling described above in step 3 using method A with 3-methoxyphenylboronic acid. HR-ES (+) calcd for $C_{34}H_{42}O_8$ (M+Na)$^+$ 601.2772. found 601.2774.

Example 20

4-{2-(2-Carboxy-ethyl)-3-[6-(5-methoxymethyl-4'-trifluoromethoxy-biphenyl-3-yloxy)-hexyl]-phenoxy}-butyric acid

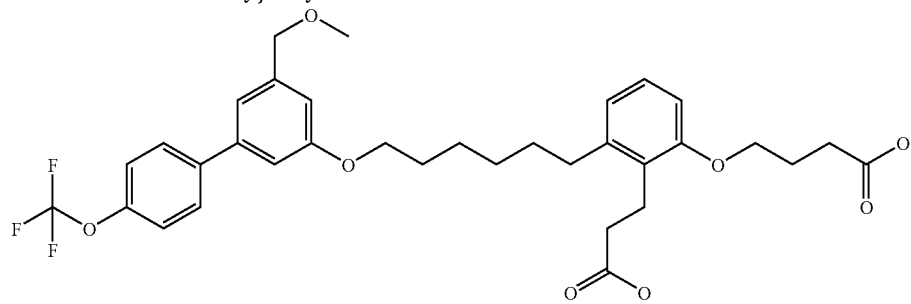

The title compound was prepared by following the general procedure for Suzuki coupling described above in step 3 using method A with 4-trifluoromethoxyphenylboronic acid. HR-ES(+) calcd for $C_{34}H_{39}O_8F_3$ (M+Na)$^+$ 655.2489. found 655.2489.

Example 21

4-[2-(2-Carboxy-ethyl)-3-[6-(3',4'-difluoro-5-methoxymethyl-biphenyl-3-yloxy)-hexyl]-phenoxy]-butyric acid

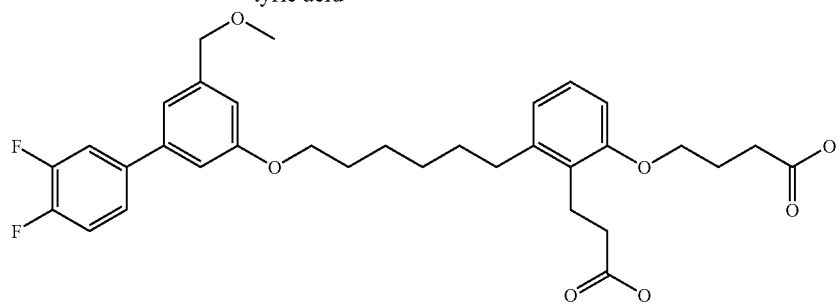

A similar procedure as described in step 3, method B was used, starting from 4-[3-[6-(3-bromo-5-methoxymethyl-phenoxy)-hexyl]-2-(2-carboxy-ethyl)-phenoxy]-butyric acid (184 mg, 0.33 mmol), 3,4-difluorophenylboronic acid (106 mg, 0.66 mmol), [1,1'-bis(diphenylphosphino)ferrocene]dichloropalladium(II) (44 mg, 0.06 mmol), and cesium carbonate (434 mg, 1.33 mmol) to obtain 4-[2-(2-carboxy-ethyl)-3-[6-(3',4'-difluoro-5-methoxymethyl-biphenyl-3-yloxy)-hexyl]-phenoxy]-butyric acid (180 mg, 93%) as a light yellow paste: ES(+)-HRMS m/e calcd for $C_{33}H_{38}F_2O_7$ (M+Na)$^+$ 607.2478. found 607.2478.

Example 22

4-[2-(2-Carboxy-ethyl)-3-[6-(3-methoxymethyl-5-pyrimidin-5-yl-phenoxy)-hexyl]-phenoxy]-butyric acid

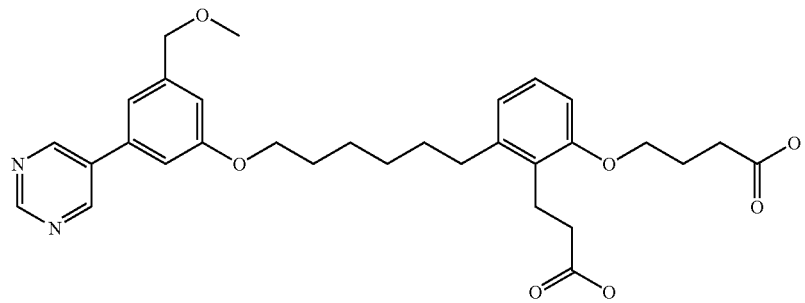

A similar procedure as described in step 3, method B was used, starting from 4-[3-[6-(3-bromo-5-methoxymethyl-phenoxy)-hexyl]-2-(2-carboxy-ethyl)-phenoxy]-butyric acid (209 mg, 0.38 mmol), 5-pyrimidinylboronic acid (94 mg, 0.76 mmol), [1,1'-bis(diphenylphosphino)ferrocene]dichloropalladium(II) (51 mg, 0.07 mmol), and cesium carbonate (492 mg, 1.51 mmol) to obtain 4-[2-(2-carboxy-ethyl)-3-[6-(3-methoxymethyl-5-pyrimidin-5-yl-phenoxy)-hexyl]-phenoxy]-butyric acid (146 mg, 70%) as a light brown paste: ES(+)-HRMS m/e calcd for $C_{31}H_{38}N_2O_7$ (M+H)$^+$ 551.2752. found 551.2748.

Example 23

4-[2-(2-Carboxy-ethyl)-3-{6-[3-(1H-indol-5-yl)-5-methoxymethyl-phenoxy]-hexyl}-phenoxy]-butyric acid A similar procedure as described in step 3, method B was used, starting from 4-[3-[6-(3-bromo-5-methoxymethyl-phenoxy)-hexyl]-2-(2-carboxy-ethyl)-phen-oxy]butyric acid (175 mg, 0.31 mmol), 5-indoleboronic acid (104 mg, 0.64 mmol), [1,1'-bis(diphenylphosphino)ferrocene]dichloropalladium(II) (51 mg, 0.07 mmol), and cesium carbonate (417 mg, 1.28 mmol) to obtain 4-[2-(2-carboxy-ethyl)-3-{6-[3-(1H-indol-5-yl)-5-methoxymethyl-phenoxy]-hexyl}-phenoxy]-butyric acid (125 mg, 69%) as a light brown solid: ES(+)-HRMS m/e calcd for $C_{35}H_{41}NO_7$ (M+Na)$^+$ 610.2775. found 610.2774.

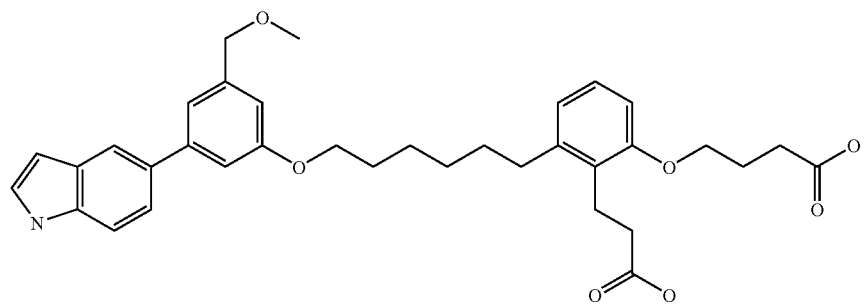

Example 24

4-[2-(2-Carboxy-ethyl)-3-[6-(4'-methanesulfonyl-5-methoxymethyl-biphenyl-3-yloxy)-hexyl]-phenoxy]-butyric acid

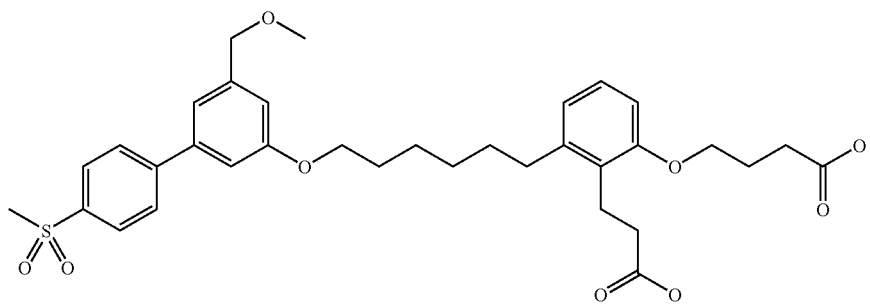

Step 1: 4-{2-(2-Ethoxycarbonyl-ethyl)-3-[6-(4'-methanesulfonyl-5-methoxymethyl-biphenyl-3-yloxy)-hexyl]-phenoxy}-butyric acid ethyl ester

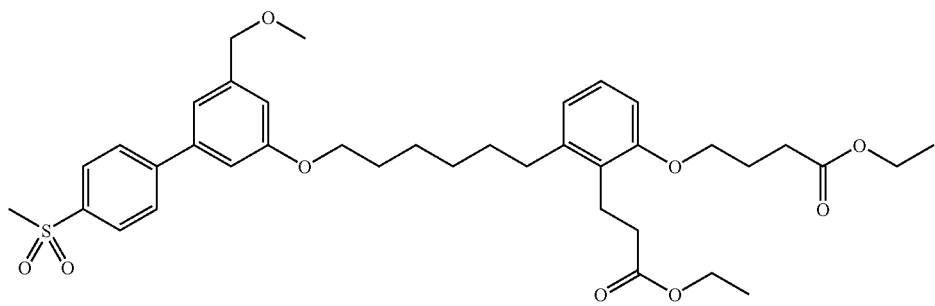

To a solution of 4-{2-(2-ethoxycarbonyl-ethyl)-3-[6-(5-hydroxymethyl-4'-methanesulfonyl-biphenyl-3-yloxy)-hexyl]-phenoxy}-butyric acid ethyl ester (250 mg, 0.37 mmol) in DMF (5 mL) were added sodium hydride (29.9 mg, 0.75 mmol), and iodomethane (106.2 mg, 0.75 mmol) at room temperature. The resulting suspension was stirred for 15 h and then the excess sodium hydride was quenched by slow addition of water (5 mL). The mixture was diluted with 1.0N hydrochloric acid (25 mL) and the organic compound was extracted into ethyl acetate (2×25 mL). The combined extracts were washed with brine solution (50 mL) and dried over anhydrous magnesium sulfate. Filtration of the drying agent and removal of the solvent under vacuum afforded the crude residue which was purified by using an ISCO 40 g column to obtain 4-{2-(2-ethoxycarbonyl-ethyl)-3-[6-(4'-methanesulfonyl-5-methoxymethyl-biphenyl-3-yloxy)-hexyl]-phenoxy}-butyric acid ethyl ester (200 mg, 78%) as a light brown oil: ES(+)-HRMS m/e calcd for $C_{38}H_{50}O_9S$ (M+Na)$^+$ 705.3068. found 705.3069.

Step 2: 4-[2-(2-Carboxy-ethyl)-3-[6-(-4'-methanesulfonyl-5-methoxymethyl-biphenyl-3-yloxy)-hexyl]-phenoxy]-butyric acid

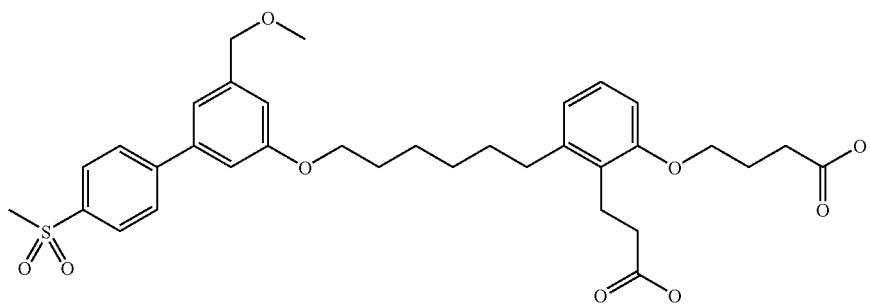

To a solution of the 4-{2-(2-ethoxycarbonyl-ethyl)-3-[6-(4'-methanesulfonyl-5-methoxymethyl-biphenyl-3-yloxy)-hexyl]-phenoxy}-butyric acid ethyl ester (195 mg, 0.29 mmol) in THF (5 mL) and ethanol (5 mL) was added aqueous 1.0 N sodium hydroxide (3 mL) at room temperature. The resulting suspension was stirred for 5 h at room temperature at which time TLC analysis of the mixture indicated the absence of starting material. Then, the reaction mixture was concentrated and the residue was diluted with water (20 mL) and extracted with diethyl ether (30 mL) to remove any neutral impurities. The aqueous layer was acidified with 1.0 N hydrochloric acid and the precipitated white organic compound was extracted into ethyl acetate (2×30 mL). The combined ethyl acetate extracts were washed with brine solution (50 mL) and the organic layers were dried over anhydrous magnesium sulfate. Filtration of the drying agent and removal of the solvent afforded 4-[2-(2-carboxy-ethyl)-3-[6-(-4'-methanesulfonyl-5-methoxymethyl-biphenyl-3-yloxy)-hexyl]-phenoxy]-butyric acid (168 mg, 94%) as a white solid: ES(+)-HRMS m/e calcd for $C_{34}H_{42}O_9S$ (M+Na)$^+$ 649.2442. found 649.2440.

Example 25

4-[3-[6-(3-Benzo[1,3]dioxol-5-yl-5-ethoxymethyl-phenoxy)-hexyl]-2-(2-carboxy-ethyl)-phenoxy]-butyric acid

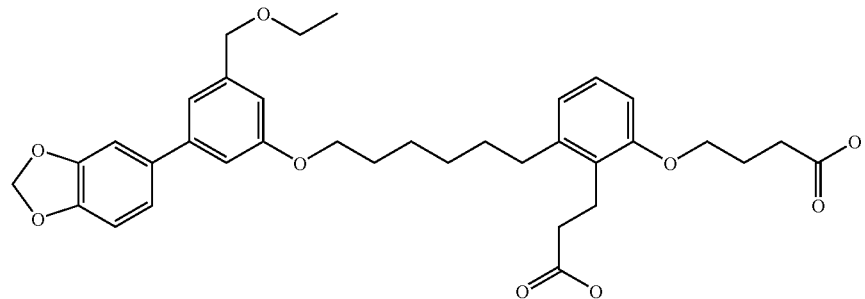

Step 1: 4-[3-[6-(3-Bromo-5-ethoxymethyl-phenoxy)-hexyl]-2-(2-ethoxycarbonyl-ethyl)-phenoxy]-butyric acid ethyl ester

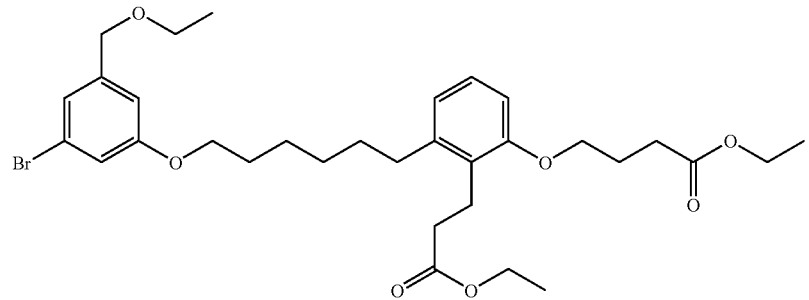

To a solution of 4-[3-[6-(3-bromo-5-hydroxymethyl-phenoxy)-hexyl]-2-(2-ethoxycarbonyl-ethyl)-phenoxy]-butyric acid ethyl ester (1.0 g, 1.68 mmol) in N,N-dimethylformamide (10 mL) was added iodoethane (403 µL, 5.04 mmol) and sodium hydride, 60% dispersion in mineral oil (202 mg, 5.04 mmol) at room temperature. The resulting suspension was stirred for 5 h. Then, the reaction mixture was diluted with water and brine. The organic compound was extracted into ethyl acetate and the combined organic extracts were washed with brine solution. The organic layers were dried over anhydrous sodium sulfate and the solvent was removed under reduced pressure. The crude material was purified by column chromatography (Isco™ 40 g) with 0-30% ethyl acetate/hexanes as eluting solvents to afford the title compound (550 mg, 53%) as a colorless oil.

HR-ES(+) calcd for $C_{32}H_{45}O_7Br$ [M+Na]$^+$ 643.2241, observed 643.2240.

Step 2: General Procedure for Suzuki Reaction and Saponification

To a solution of 4-[3-[6-(3-Bromo-5-ethoxymethyl-phenoxy)-hexyl]-2-(2-ethoxycarbonyl-ethyl)-phenoxy]-butyric acid ethyl ester (100 mg, 0.16 mmol), cesium carbonate (207 mg, 0.64 mmol) and boronic acid (0.32 mmol) in DME (4 mL) was added Pd(PPh$_3$)$_4$ (9 mg, 5 mol %). The reaction mixture was heated at 90° C. for 12 h, cooled down to room temperature then diluted with EtOAc. The resulting solution was washed with 10% aq. HCl and brine. The organic layer was then dried over anhydrous sodium sulfate and concentrated under vacuo to afford the crude material. Without further purification, the crude sample was dissolved in hot ethanol (4 mL) and 2.0N sodium hydroxide (1 mL) was added. The resulting solution was heated to 60° C. and stirred for 4 h. Then, the reaction mixture was cooled down and diluted with EtOAc, washed with 10% aq. HCl and brine. The combined ethyl acetate extracts were dried over anhydrous sodium sulfate and the solvent was removed under reduced pressure. The desired products were isolated by preparative HPLC.

4-[3-[6-(3-Benzo[1,3]dioxol-5-yl-5-
ethoxymethyl-phenoxy)-hexyl]-2-(2-carboxy-
ethyl)-phenoxy]-
butyric acid

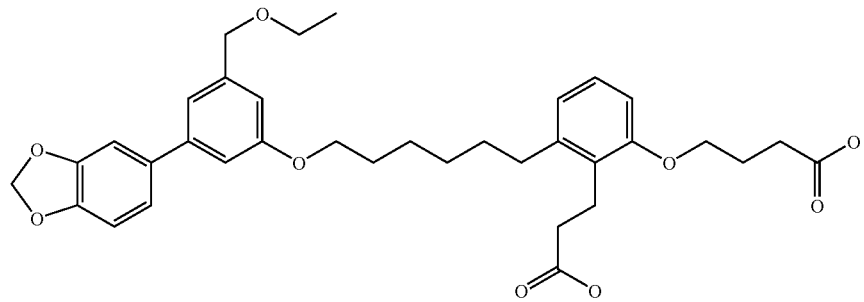

The title compound was prepared by following the general procedure for Suzuki coupling described above in step 2 with 3,4-methylenedioxyphenyl boronic acid. HR-ES(+) calcd for $C_{35}H_{42}O_9$ $(M+Na)^+$ 629.2721. found 629.2724.

Example 26

4-{2-(2-Carboxy-ethyl)-3-[6-(5-ethoxymethyl-4'-
fluoro-biphenyl-3-yloxy)-hexyl]-phenoxy}-butyric
acid

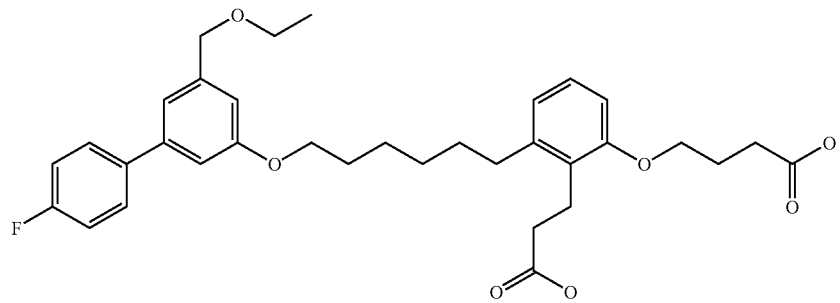

The title compound was prepared by following the general procedure for Suzuki coupling described above in step 2 with 4-fluorophenylboronic acid. HR-ES(+) calcd for $C_{34}H_{41}O_7F$ $(M+Na)^+$ 603.2728. found 603.2733.

Example 27

4-{2-(2-Carboxy-ethyl)-3-[6-(5-ethoxymethyl-4'-
trifluoromethyl-biphenyl-3-yloxy)-hexyl]-phenoxy}-
butyric acid

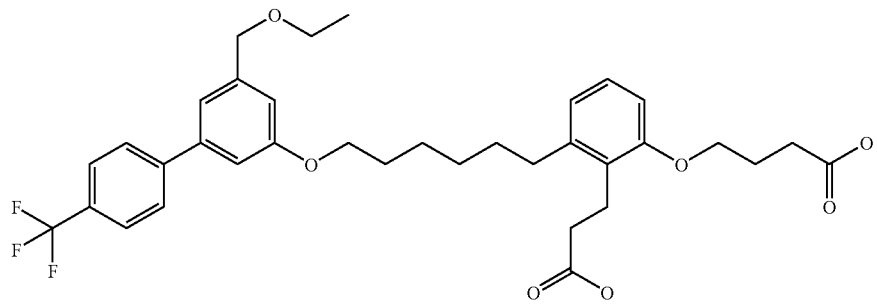

The title compound was prepared by following the general procedure for Suzuki coupling described above in step 2 with 4-trifluoromethylphenylboronic acid. HR-ES(+) calcd for $C_{35}H_{41}O_7F_3$ (M+Na)$^+$ 653.2696. found 653.2700.

Example 28

4-{2-(2-Carboxy-ethyl)-3-[6-(5-ethoxymethyl-4'-chloro-biphenyl-3-yloxy)-hexyl]-phenoxy}-butyric acid

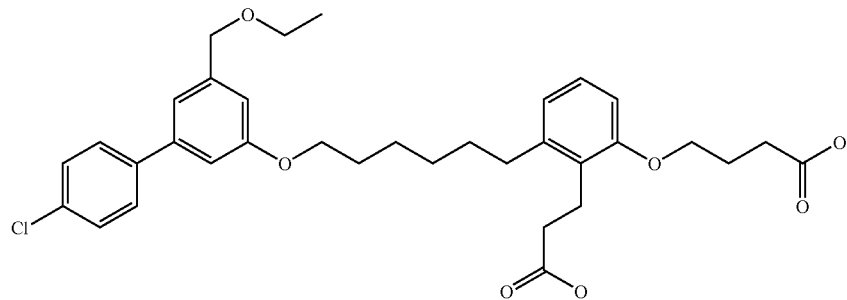

The title compound was prepared by following the general procedure for Suzuki coupling described above in step 2 with 4-chlorophenylboronic acid. HR-ES(+) calcd for $C_{34}H_{41}O_7Cl$ (M+Na)$^+$ 619.2433. found 619.2434.

Example 29

4-[2-(2-Carboxy-ethyl)-3-[6-(5-ethoxymethyl-4'-methanesulfonyl-biphenyl-3-yloxy)-hexyl]-phenoxy]-butyric acid

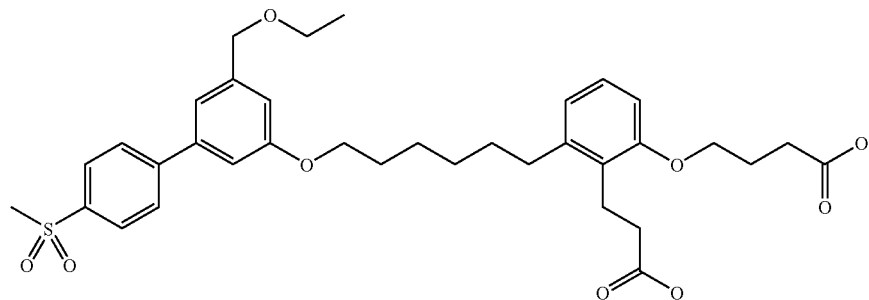

Step 1: 4-{2-(2-Ethoxycarbonyl-ethyl)-3-[6-(5-ethoxymethyl-4'-methanesulfonyl-biphenyl-3-yloxy)-hexyl]-phenoxy}-butyric acid ethyl ester

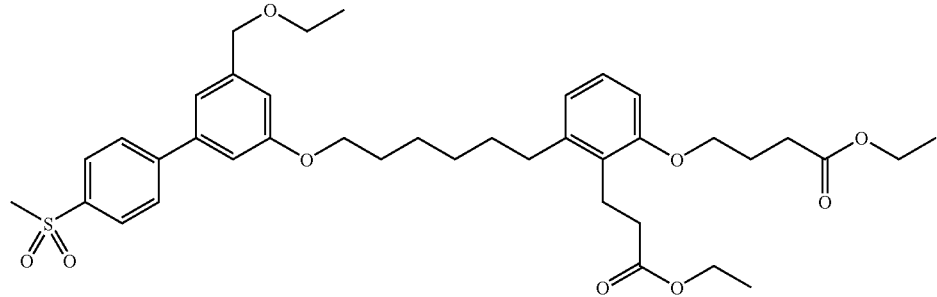

A similar procedure as described in Example 24, step 1 was used, starting from 4-{2-(2-ethoxycarbonyl-ethyl)-3-[6-(5-hydroxymethyl-4'-methanesulfonyl-biphenyl-3-yloxy)-hexyl]-phenoxy}-butyric acid ethyl ester (250 mg, 0.37 mmol), sodium hydride (29.9 mg, 0.75 mmol), and iodoethane (116.7 mg, 0.75 mmol) to obtain 4-{2-(2-ethoxycarbonyl-ethyl)-3-[6-(5-ethoxymethyl-4'-methanesulfonyl-biphenyl-3-yloxy)-hexyl]-phenoxy}-butyric acid ethyl ester (110 mg, 42%) as a light brown oil: ES(+)-HRMS m/e calcd for $C_{39}H_{52}O_9S$ (M+Na)$^+$ 719.3224, found 719.3227.

Step 2: 4-[2-(2-Carboxy-ethyl)-3-[6-(5-ethoxymethyl-4'-methanesulfonyl-biphenyl-3-yloxy)-hexyl]-phenoxy]-butyric acid To a solution of 4-[3-[6-(3-Bromo-5-hydroxymethyl-phenoxy)-hexyl]-2-(2-ethoxycarbonyl-ethyl)-phenoxy]-butyric acid ethyl ester (2.99 g, 5.05 mmol) in DCM (100 mL), TEA (3.52 mL, 25.26 mmol), DMAP (62 mg, 0.505 mmol) were added, followed by MsCl (0.60 mL, 7.58 mmol), and stirred at room temperature for 2.5 h. MeOH (4 mL) was added to quench the reaction. The solvent was removed under reduced pressure. Flash column chromatography (40% EtOAc/Hex) provided a colorless oil (2.51 g, 74% yield). $^1$H NMR (CDCl$_3$): δ 7.11-7.05 (m, 3H), 6.86 (s, 1H), 6.77 (d, 1H), 6.68 (d, 1H), 5.14 (s, 2H), 4.17-4.08 (m, 4H), 4.01-3.91 (m, 4H), 2.99-2.93 (m, 5H), 2.63 (dd, 2H), 2.56-2.46 (m, 4H), 2.17-0.89 (m, 16H).

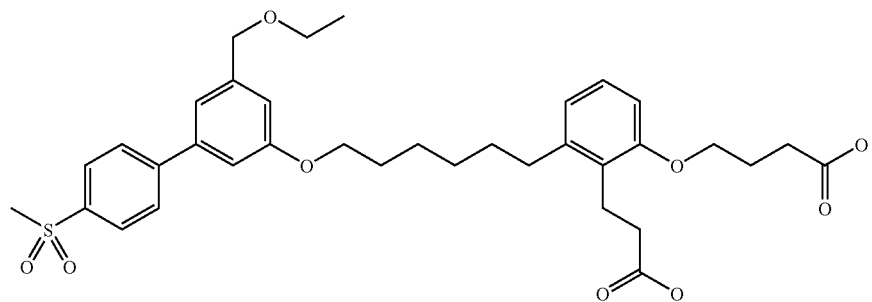

A similar procedure as described in Example 24, step 2 was used, starting from 4-{2-(2-ethoxycarbonyl-ethyl)-3-[6-(5-ethoxymethyl-4'-methanesulfonyl-biphenyl-3-yloxy)-hexyl]-phenoxy}-butyric acid ethyl ester (101 mg, 0.145 mmol) and 1.0 N aqueous sodium hydroxide (1.5 mL) to afford 4-[2-(2-carboxy-ethyl)-3-[6-(5-ethoxymethyl-4'-methanesulfonyl-biphenyl-3-yloxy)-hexyl]-phenoxy]-butyric acid (90 mg, 97%) as a white solid: ES(+)-HRMS m/e calcd for $C_{35}H_{44}O_9S$ (M+Na)$^+$ 663.2598. found 663.2594.

Method C

Step 1: 4-[3-[6-(3-Bromo-5-methanesulfonyloxymethyl-phenoxy)-hexyl]-2-(2-ethoxycarbonyl-ethyl)-phenoxy]-butyric acid ethyl ester

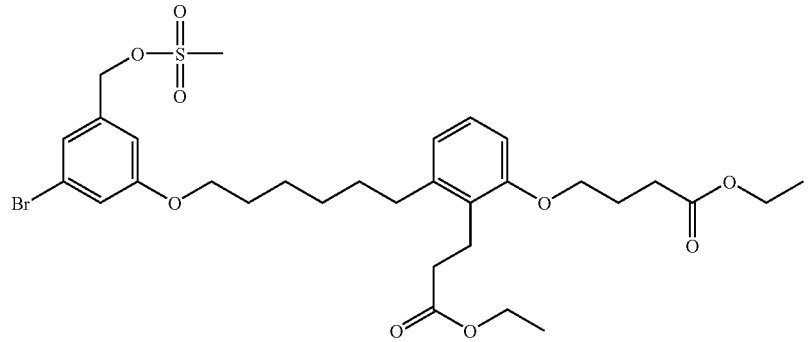

Step 2: 4-[3-[6-(3-Bromo-5-dimethylamino-methyl-phenoxy)-hexyl]-2-(2-ethoxycarbonyl-ethyl)-phenoxy]-butyric acid ethyl ester

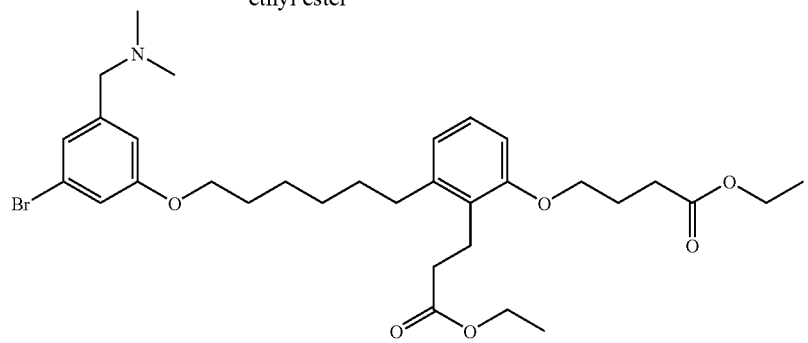

The a solution of 4-[3-[6-(3-Bromo-5-methanesulfonyloxymethyl-phenoxy)-hexyl]-2-(2-ethoxycarbonyl-ethyl)-phenoxy]-butyric acid ethyl ester (2.5 g, 3.72 mmol) in MeCN (40 mL), N,N-dimethylamine 2M/THF (3.72 mL, 7.44 mmol) was added, and stirred at room temperature overnight. The solvent was removed under reduced pressure. Flash column chromatography (50% EtOAc/Hex) provided a light yellow oil (1.47 g, 64% yield). $^1$H NMR (CDCl$_3$): δ 7.08 (t, 1H), 7.03 (s, 1H), 6.93 (s, 1H), 6.79 (s, 1H), 6.77 (d, 1H), 6.68 (d, 1H), 4.17-4.06 (m, 4H), 3.99 (dd, 2H), 3.92 (dd, 2H), 3.34 (s, 2H), 2.97 (dd, 2H), 2.63 (dd, 2H), 2.56-2.46 (m, 4H), 2.23 (s, 6H), 2.17-0.89 (m, 16H).

Step 3: 4-[3-[6-(3-Bromo-5-cyanomethyl-phenoxy)-hexyl]-2-(2-ethoxy carbonylethyl)-phenoxy]-butyric acid ethyl ester

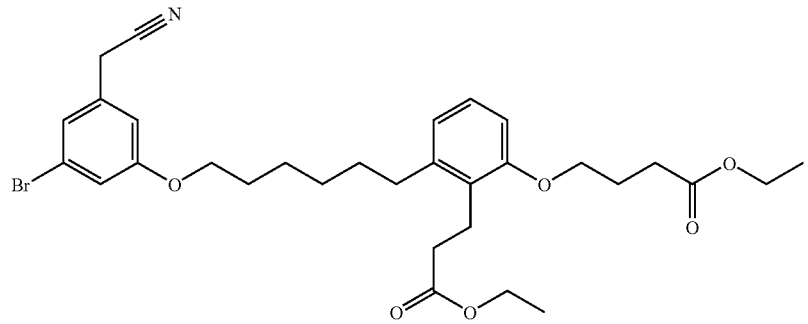

To a solution of 4-[3-[6-(3-bromo-5-methanesulfonyloxymethyl-phenoxy)-hexyl]-2-(2-ethoxycarbonyl-ethyl)-phenoxy]-butyric acid ethyl ester (2.51 g, 3.74 mmol) in DMF (40 mL), KCN (292 mg, 4.48 mmol) was added and stirred a 60° C. overnight. The reaction was diluted with EtOAc (250 mL) washed with water (100 mL×2), brine (50 mL), dried with Na$_2$SO$_4$. Concentration under reduced pressure provided an oil. Flash column chromatography (30% EtOAc/Hex) provided a light yellow oil (1.19 g, 53% yield). $^1$H NMR (CDCl$_3$): δ 7.08 (t, 1H), 7.04 (s, 1H), 6.99 (s, 1H), 6.79 (s, 1H), 6.77 (d, 1H), 6.68 (d, 1H), 4.17-4.06 (m, 4H), 4.01-3.91 (m, 4H), 3.68 (s, 2H), 2.97 (dd, 2H), 2.63 (dd, 2H), 2.56-2.46 (m, 4H), 2.17-0.89 (m, 16H).

Step 4: General Procedure for Suzuki Reaction and Saponification

In a sealable tube, an aryl bromide derivative (100 mg, 0.157 mmol) in DME (3 mL) was added, followed by Boronic acid (100 mg), Cs$_2$CO$_3$ (100 mg), and PdCl$_2$(dppf) (20 mg). The reaction mixture was shaken at 90° C. overnight. The reaction was diluted with EtOAc (5 mL), washed with water (3 mL). The organic layer was separated, concentration under reduced pressure gave an oil, which was used in the next step without further purification. The residue oil was dissolved in EtOH (5 mL), 3N NaOH (0.5 mL) was added and stirred at 60° C. for 3 h. 3N HCl (0.55 mL) was added to neutralize the reactions. Concentration under reduced pressure gave an oil which was purified by preparative HPLC to provide the following compounds.

Example 30

4-[3-[6-(3-Benzo[1,3]dioxol-5-yl-5-dimethylaminomethyl-phenoxy)-hexyl]-2-(2-carboxy-ethyl)-phenoxy]-butyric acid

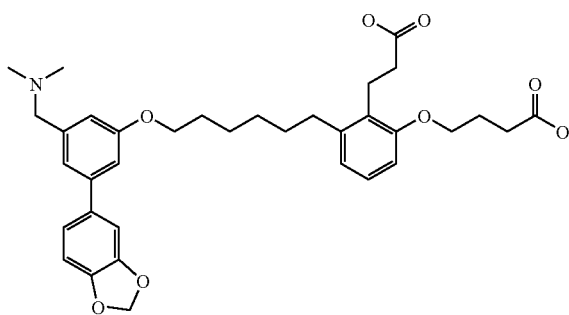

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 3,4-methylenedioxyphenylboronic Acid. LC/MS indicated a purity of 93% as measured by UV 214 nM. HR-ES(+):calculated for $C_{35}H_{44}NO_8$ $(M+H)^{1+}$ 606.3062. found 606.3060.

Example 31

4-{2-(2-Carboxy-ethyl)-3-[6-(3-dimethylaminomethyl-5-thiophen-3-yl-phenoxy)-hexyl]-phenoxy}-butyric acid

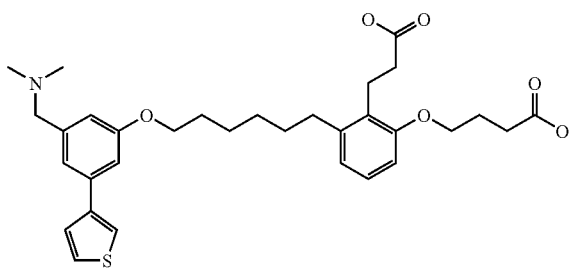

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with thiopheneboronic acid. LC/MS indicated a purity of 100% as measured by UV 214 nM. HR-ES(+):calculated for $C_{32}H_{42}NO_6S$ $(M+H)^{1+}$ 568.2728, found 568.2726.

Example 32

4-{2-(2-Carboxy-ethyl)-3-[6-(5-dimethylaminomethyl-biphenyl-3-yloxy)-hexyl]-phenoxy}-butyric acid

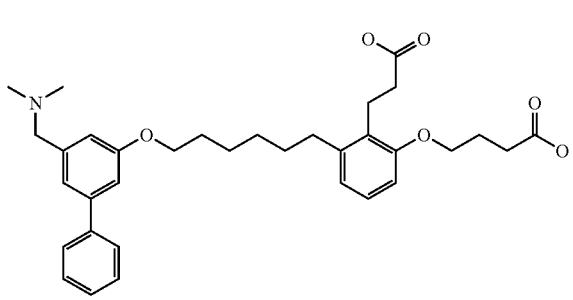

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with phenylboronic acid. LC/MS indicated a purity of 100% as measured by UV 214 nM. HR-ES(+):calculated for $C_{34}H_{44}NO_6$ $(M+H)^{1+}$ 562.3163, found 562.3161.

Example 33

4-{2-(2-Carboxy-ethyl)-3-[6-(5-dimethylaminomethyl-4'-fluoro-biphenyl-3-yloxy)-hexyl]-phenoxy}-butyric acid

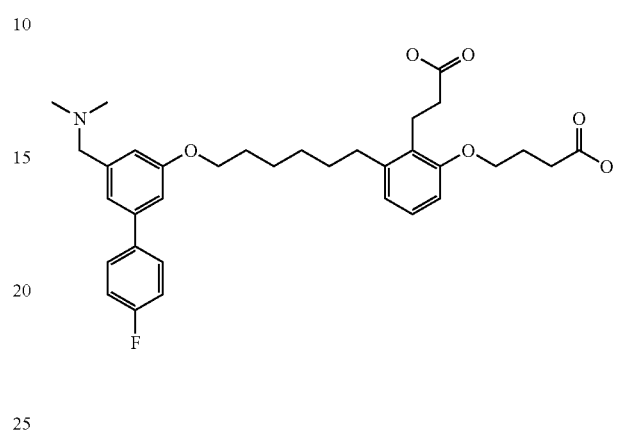

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 4-fluorophenylboronic acid. LC/MS indicated a purity of 100% as measured by UV 214 nM. HR-ES(+):calculated for $C_{34}H_{43}NO_6F$ $(M+H)^{1+}$ 580.3069. found 580.3068.

Example 34

4-{2-(2-Carboxy-ethyl)-3-[6-(4'-chloro-5-dimethylaminomethyl-biphenyl-3-yloxy)-hexyl]-phenoxy}-butyric acid

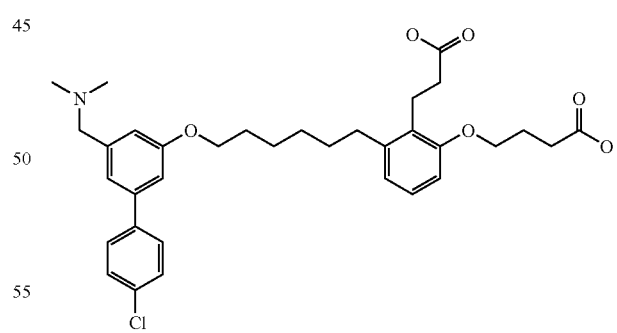

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 4-chlorophenylboronic acid. LC/MS indicated a purity of 100% as measured by UV 214 nM. HR-ES(+):calculated for $C_{34}H_{43}NO_6Cl$ $(M+H)^{1+}$ 596.2774. found 596.2774.

Example 35

4-{2-(2-Carboxy-ethyl)-3-[6-(5-dimethylaminomethyl-3'-fluoro-4'-methyl-biphenyl-3-yloxy)-hexyl]-phenoxy}-butyric acid

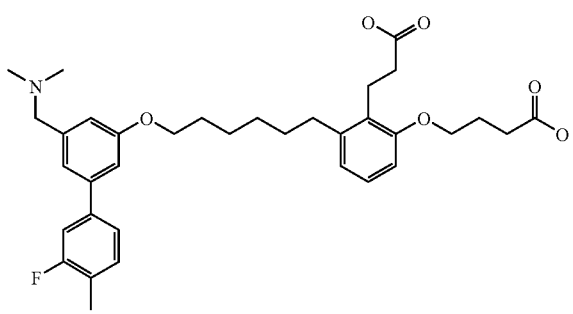

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 3-fluor-4-methylphenylboronic acid. LC/MS indicated a purity of 100% as measured by UV 214 nM. HR-ES(+):calculated for $C_{35}H_{45}NO_6F$ (M+H)$^{1+}$ 594.3226. found 594.3225.

Example 36

4-{2-(2-Carboxy-ethyl)-3-[6-(5-dimethylaminomethyl-3'-fluoro-biphenyl-3-yloxy)-hexyl]-phenoxy}-butyric acid

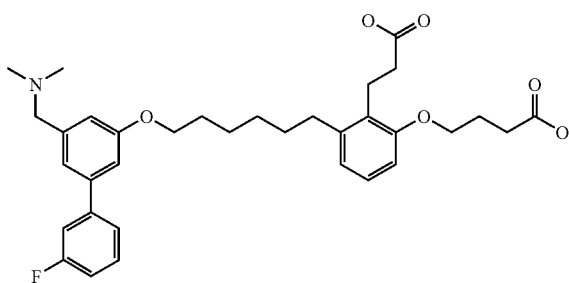

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 3-fluorophenylboronic acid. LC/MS indicated a purity of 100% as measured by UV 214 nM. HR-ES(+):calculated for $C_{34}H_{43}NO_6F$ (M+H)$^{1+}$ 580.3069. found 580.3065.

Example 37

4-{2-(2-Carboxy-ethyl)-3-[6-(5-dimethylaminomethyl-4'-trifluoromethyl-biphenyl-3-yloxy)-hexyl]phenoxy}-butyric acid

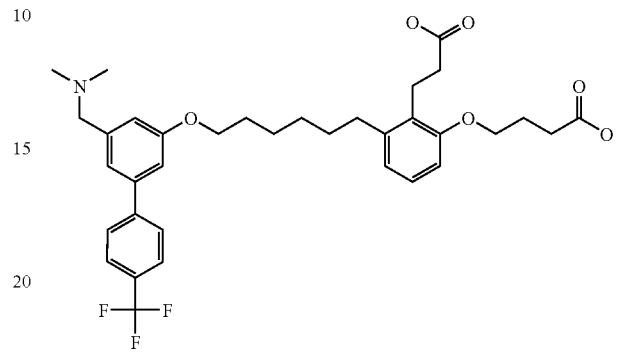

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 4-trifluoromethylphenylboronic acid. LC/MS indicated a purity of 86% as measured by UV 214 nM. LC/MS: calculated for $C_{35}H_{43}F_3NO_6$ (M+H)$^{1+}$ 630.30. found 630.30.

Example 38

4-{2-(2-Carboxy-ethyl)-3-[6-(5-dimethylaminomethyl-4'-methanesulfonyl-biphenyl-3-yloxy)-hexyl]-phenoxy}-butyric acid

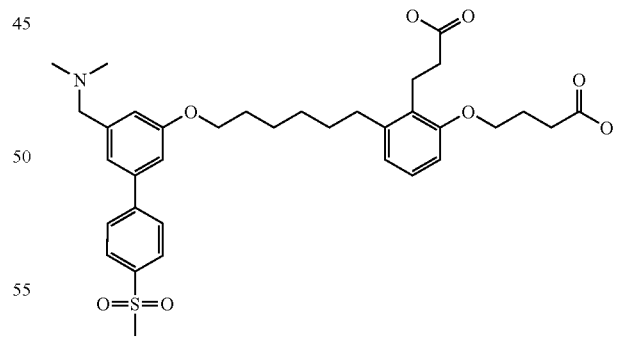

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 4-methanesulfonylphenylboronic acid. LC/MS indicated a purity of 85% as measured by UV 214 nM. HR-ES(+):calculated for $C_{35}H_{46}NO_8S$ (M+H)$^{1+}$ 640.2939. found 640.2940.

Example 39

4-{2-(2-Carboxy-ethyl)-3-[6-(5-dimethylaminomethyl-3'-methanesulfonyl-biphenyl-3-yloxy)-hexyl]-phenoxy}-butyric acid

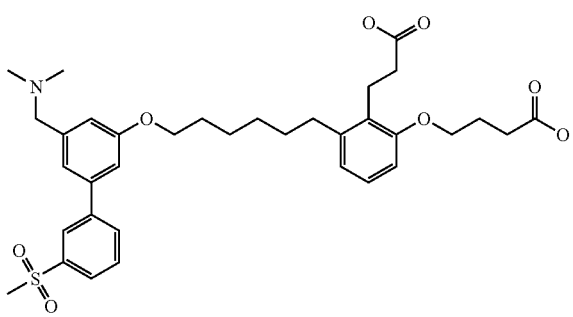

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 3-methanesulfonylphenylboronic acid. LC/MS indicated a purity of 85% as measured by UV 214 nM. HR-ES(+):calculated for $C_{35}H_{46}NO_8S$ $(M+H)^{1+}$ 640.2939. found 640.2937.

Example 40

4-{2-(2-Carboxy-ethyl)-3-[6-(3-dimethylaminomethyl-5-pyridin-4-yl-phenoxy)-hexyl]-phenoxy}-butyric acid

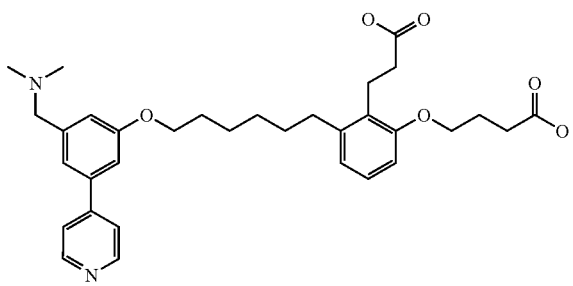

The title compound was prepared according to general method described in step 4 by reaction of 4-[3-[6-(3-dimethylaminomethyl-5-bromo-phenoxy)-hexyl]-2-(2-ethoxy-carbonyl-ethyl)-phenoxy]-butyric acid ethyl ester with 4-pyridineboronic acid. LC/MS indicated a purity of 100% as measured by UV 214 nM. HR-ES(+):calculated for $C_{33}H_{43}N_2O_6$ $(M+H)^{1+}$ 563.3116, found 563.3113.

Example 41

4-{2-(2-Carboxy-ethyl)-3-[6-(3-cyanomethyl-5-thiophen-3-yl-phenoxy)-hexyl]-phenoxy}-butyric acid

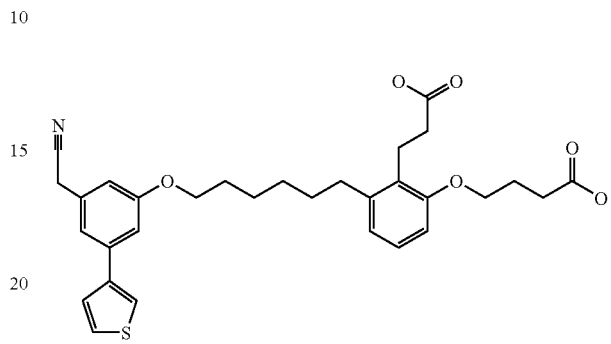

The title compound was prepared according to general method described in step 4 by reaction of 4-[3-[6-(3-cyanomethyl-5-bromo-phenoxy)-hexyl]-2-(2-ethoxycarbonyl-ethyl)-phenoxy]-butyric acid ethyl ester with thiophene-3-boronic acid. LC/MS indicated a purity of 100% as measured by UV 214 nM. Calculated for $C_{31}H_{36}NO_6S$ $(M+H)^{1+}$ 550.22. found 550.20.

Example 42

4-{2-(2-Carboxy-ethyl)-3-[6-(5-cyanomethyl-biphenyl-3-yloxy)-hexyl]-phenoxy}-butyric acid

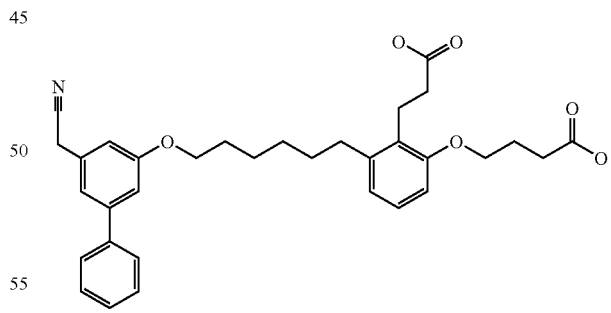

The title compound was prepared according to general method described in step 4 by reaction of 4-[3-[6-(3-dyanomethyl-5-bromo-phenoxy)-hexyl]-2-(2-ethoxycarbonyl-ethyl)-phenoxy]-butyric acid ethyl ester with phenylboronic acid. LC/MS indicated a purity of 100% as measured by UV 214 nM. HR-ES(+):calculated for $C_{33}H_{38}NO_6$ $(M+H)^{1+}$ 566.2513. found 566.2513.

Method D

Example 43

4-[3-[6-(3-Benzo[1,3]dioxol-5-yl-5-ethoxy-phenoxy)-hexyl]-2-(2-carboxy-ethyl)-phenoxy]-butyric acid

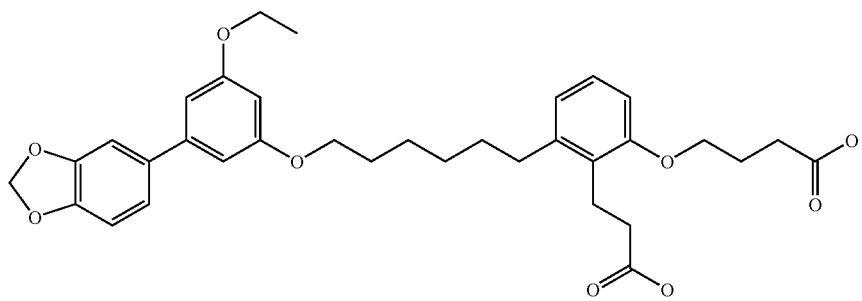

Step 1: 5-Bromo-benzene-1,3-diol

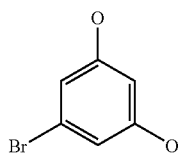

To a suspension of 5-bromo-1,3-dimethoxy-benzene (15 g, 67.02 mmol) and sodium iodide (100.5 g, 670.2 mmol) in acetonitrile (577 mL) was added trimethylsilyl chloride (42.39 mL, 335.1 mmol) at room temperature. Then, the resulting light yellow suspension was heated to reflux for 48 h. Then, it was cooled to room temperature and diluted with water (150 mL). The organic compound was extracted into ethyl acetate (2×150 mL) and the combined ethyl acetate extracts were washed with saturated sodium thiosulfate solution (300 mL) to remove the iodine color and was also washed with brine solution (300 mL). Then, the organic layer was dried over anhydrous magnesium sulfate, filtered, and concentrated in vacuo. The crude residue was purified by using an ISCO 330 g column, eluting with 5-30% ethyl acetate in hexanes to obtain 5-bromo-benzene-1,3-diol (9.24 g, 73%) as a light brown solid: ES(+)-HRMS m/e calcd for $C_6H_5BrO_2$ $(M+H)^+$ 189.2341. found 189.2346.

Step 2: 4-[3-[6-(3-Bromo-5-hydroxy-phenoxy)-hexyl]-2-(2-ethoxycarbonyl-ethyl)-phenoxy]-butyric acid ethyl ester

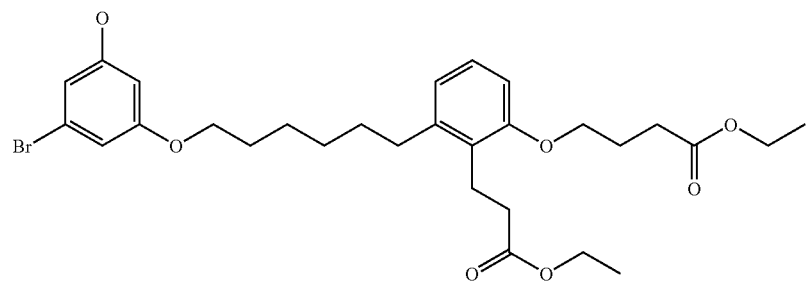

To a solution of 4-[3-(6-bromo-hexyl)-2-(2-ethoxycarbonyl-ethyl)-phenoxy]-butyric acid ethyl ester (4.48 g, 9.5 mmol) and 5-bromo-benzene-1,3-diol (1.79 g, 9.47 mmol) in dimethylsulfoxide (30 mL) was added lithium hydride (160 mg, 20 mmol) at room temperature. The resulting suspension was stirred for 48 h and then the reaction mixture was diluted with water (100 mL). The organic compound was extracted into ethyl acetate (3×50 mL) and the combined organic extracts were washed with water (100 mL) and brine solution (100 mL). The organic layers were dried over anhydrous magnesium sulfate and filtration of the drying agent and concentration of the solvent under vacuum gave the crude product which was purified by using an ISCO 120 g column, eluting with 0-30% ethyl acetate in hexanes to afford 4-[3-[6-(3-bromo-5-hydroxy-phenoxy)-hexyl]-2-(2-ethoxycarbonyl-ethyl)-phenoxy]-butyric acid ethyl ester (2.73 g, 74%) as a white solid: ES(+)-HRMS m/e calcd for $C_{29}H_{39}BrO_7$ (M+Na)$^+$ 601.1771, found 601.1773.

Step 3: 4-[3-[6-(3-Bromo-5-ethoxy-phenoxy)-hexyl]-2-(2-ethoxycarbonyl-ethyl)-phenoxy]-butyric acid ethyl ester

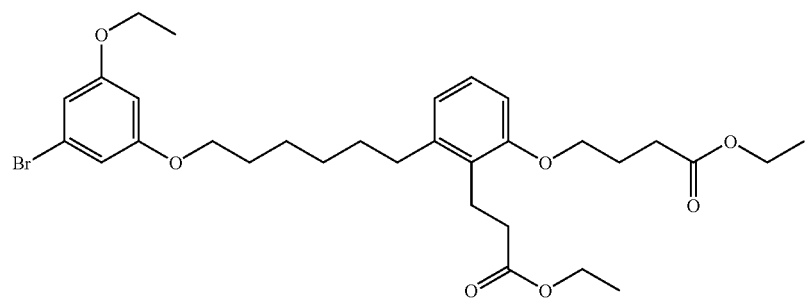

To a mixture of 4-[3-[6-(3-bromo-5-hydroxy-phenoxy)-hexyl]-2-(2-ethoxycarbonyl-ethyl)-phenoxy]-butyric acid ethyl ester (163 mg, 0.28 mmol) and potassium carbonate (117 mg, 0.84 mmol) were added dimethylformamide (4 mL), acetone (8 mL), and iodoethane (219 mg, 1.4 mmol) at room temperature. The resulting suspension was heated to reflux for 2 days. Then, the reaction mixture was cooled to room temperature and diluted with water (20 mL). The organic compound was extracted into ethyl acetate (2×25 mL) and the combined organic extracts were washed with water (50 mL) and brine solution (50 mL). The organic layers were dried over anhydrous magnesium sulfate and filtration of the drying agent and concentration of the solvent gave the crude product which was purified by using an ISCO 40 g column, eluting with 0-30% ethyl acetate in hexanes to afford 4-[3-[6-(3-bromo-5-ethoxy-phenoxy)-hexyl]-2-(2-ethoxycarbonyl-ethyl)-phenoxy]-butyric acid ethyl ester (166 mg, 98%) as a colorless oil: ES(+)-HRMS m/e calcd for $C_{31}H_{43}BrO_7$ (M+H)$^+$ 607.2265. found 607.2270.

Step 4: 4-[3-[6-(3-Benzo[1,3]dioxol-5-yl-5-ethoxy-phenoxy)-hexyl]-2-(2-ethoxycarbonyl-ethyl)-phenoxy]-butyric acid ethyl ester

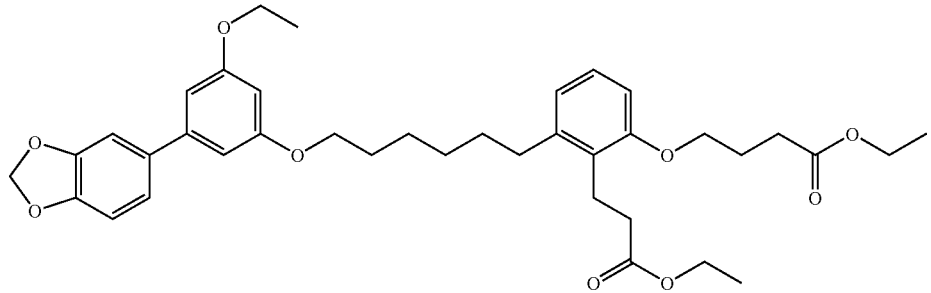

To a mixture of 4-[3-[6-(3-bromo-5-ethoxy-phenoxy)-hexyl]-2-(2-ethoxycarbonyl-ethyl)-phenoxy]-butyric acid ethyl ester (155 mg, 0.255 mmol), 3,4-methylenedioxybenzeneboronic acid (85 mg, 0.51 mmol), [1,1'-bis(diphenylphosphino)ferrocene]dichloropalladium(II) (73 mg, 0.1 mmol), and cesium carbonate (166 mg, 0.51 mmol) was added dimethoxyethane (10 mL) at room temperature under nitrogen atmosphere. The resulting brown reaction mixture was heated to 96° C. and stirred for 15 h at which time the TLC analysis of the reaction mixture indicated the absence of starting material. Then, the reaction mixture was cooled to room temperature and diluted with water (50 mL) and ethyl acetate (50 mL). The two layers were separated and the aqueous layer was extracted with ethyl acetate (50 mL) and the combined organic extracts were washed with water (50 mL) and brine solution (50 mL). The organic layer was dried over anhydrous magnesium sulfate and filtration of the drying agent and removal of the solvent under vacuum gave the colored residue which was purified by using an ISCO 40 column, eluting with 0-25% ethyl acetate in hexanes to obtain 4-[3-[6-(3-benzo[1,3]dioxol-5-yl-5-ethoxy-phenoxy)-hexyl]-2-(2-ethoxycarbonyl-ethyl)-phenoxy]-butyric acid ethyl ester (165 mg, 99%) as a colorless viscous oil: ES(+)-LRMS m/e calcd for $C_{38}H_{48}O_9$ (M+Na)$^+$ 671.3190. found 671.3185.

Step 5: 4-[3-[6-(3-Benzo[1,3]dioxol-5-yl-
5-ethoxy-phenoxy)-hexyl]-2-(2-carboxy-
ethyl)-phenoxy]-
butyric acid

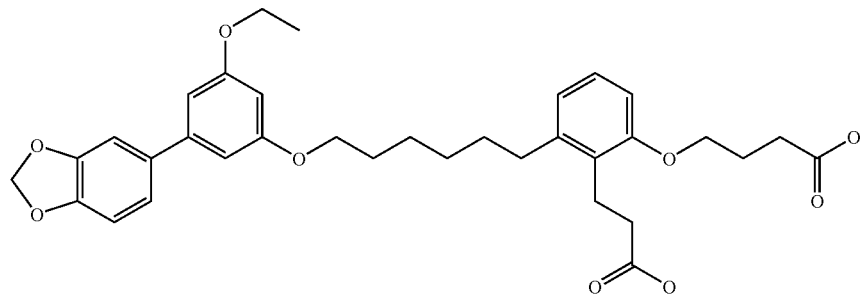

To a solution of the 4-[3-[6-(3-benzo[1,3]dioxol-5-yl-5-ethoxy-phenoxy)-hexyl]-2-(2-ethoxycarbonyl-ethyl)-phenoxy]-butyric acid ethyl ester (152 mg, 0.23 mmol) in THF (5 mL) and ethanol (5 mL) was added aqueous 1.0 N sodium hydroxide (5 mL) at room temperature. The resulting suspension was stirred for 5 h at room temperature at which time TLC analysis of the mixture indicated the absence of starting material. Then, the reaction mixture was concentrated and the residue was diluted with water (20 mL) and extracted with diethyl ether (30 mL) to remove any neutral impurities. The aqueous layer was acidified with 1.0 N hydrochloric acid and the precipitated white organic compound was extracted into ethyl acetate (2×30 mL). The combined ethyl acetate extracts were washed with brine solution (50 mL) and the organic layers were dried over anhydrous magnesium sulfate. Filtration of the drying agent and removal of the solvent afforded 4-[3-[6-(3-benzo[1,3]dioxol-5-yl-5-ethoxy-phenoxy)-hexyl]-2-(2-carboxy-ethyl)-phenoxy]-butyric acid (129 mg, 95%) as a off-white waxy solid: ES(+)-HRMS m/e calcd for $C_{34}H_{40}O_9$ (M+H)$^+$ 593.2745. found 593.2744.

Example 44

4-[2-(2-Carboxy-ethyl)-3-[6-(5-ethoxy-biphenyl-3-yloxy)-hexyl]-phenoxy]-butyric acid Step 1: 3-Bromo-5-ethoxy-phenol

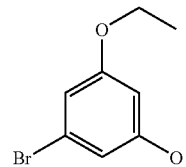

A similar procedure as described in Example 43, step 2 was used, starting from 5-bromo-benzene-1,3-diol (9.2 g, 48.67 mmol), iodoethane (8.13 g, 51.1 mmol), and lithium hydride (720 mg, 97.34 mmol) to afford 3-bromo-5-ethoxy-phenol (3.38 g, 32%) as a light yellow oil: ES(+)-HRMS m/e calcd for $C_8H_9BrO_2$ (M+Na)$^+$ 217. found 217.

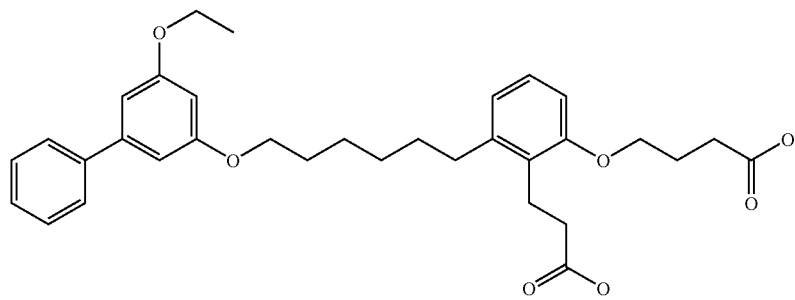

Step 2: 4-[3-[6-(3-Bromo-5-ethoxy-phenoxy)-hexyl]-2-(2-ethoxycarbonyl-ethyl)-phenoxy]-butyric acid ethyl ester

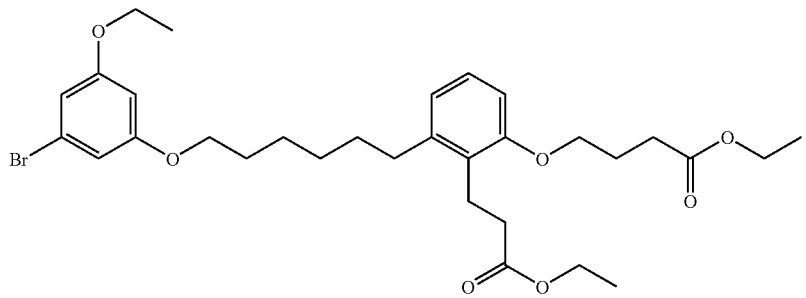

A similar procedure as described in Example 43, step 3 was used, starting from 4-[3-(6-bromo-hexyl)-2-(2-ethoxycarbonyl-ethyl)-phenoxy]-butyric acid ethyl ester (8.07 g, 17.13 mmol), 3-bromo-5-ethoxy-phenol (3.38 g, 15.57 mmol), and potassium carbonate (4.3 g, 31.14 mmol) to obtain 4-[3-[6-(3-bromo-5-ethoxy-phenoxy)-hexyl]-2-(2-ethoxycarbonyl-ethyl)-phenoxy]-butyric acid ethyl ester (7.77 g, 82%) as a colorless oil: ES(+)-HRMS m/e calcd for $C_{31}H_{43}BrO_7$ (M+H)$^+$ 607.2265. found 607.2270.

Step 3: 4-[3-[6-(5-Ethoxy-biphenyl-3-yloxy)-hexyl]-2-(2-ethoxycarbonyl-ethyl)-phenoxy]-butyric acid ethyl ester

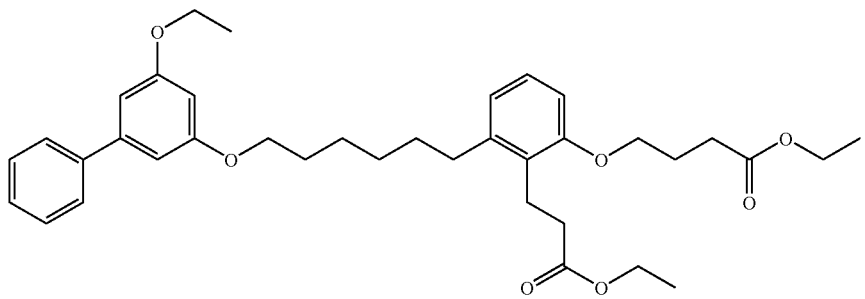

To a mixture of 4-[3-[6-(3-bromo-5-ethoxy-phenoxy)-hexyl]-2-(2-ethoxycarbonyl-ethyl)-phenoxy]-butyric acid ethyl ester (305 mg, 0.5 mmol), phenylboronic acid (125 mg, 1.0 mmol), [1,1'-bis(diphenylphosphino)ferrocene]dichloropalladium(II) (55 mg, 0.075 mmol), and cesium carbonate (331 mg, 1.0 mmol) in a microwave tube was added dimethoxyethane (5.9 mL) under nitrogen atmosphere at room temperature. The resulting brown reaction mixture was heated to 120° C. in a microwave for 30 minutes. The reaction mixture was diluted with ethyl acetate (50 mL) and the undissolved residue was filtered off and washed with water (50 mL). Then, the two layers of filtrate were separated and the aqueous layer was extracted with ethyl acetate (20 mL). The combined organic extracts were washed with water (50 mL) and brine solution (50 mL). The organic layer was dried over anhydrous magnesium sulfate and filtration of the drying agent and removal of the solvent under vacuum gave the colored residue which was purified by using an ISCO 40 column, eluting with 2-25% ethyl acetate in hexanes to obtain 4-[3-[6-(5-ethoxy-biphenyl-3-yloxy)-hexyl]-2-(2-ethoxycarbonyl-ethyl)-phenoxy]-butyric acid ethyl ester (255 mg, 84%) as a colorless viscous oil: ES(+)-LRMS m/e calcd for $C_{37}H_{48}O_7$ (M+Na)$^+$ 627.3292. found 627.3292.

Step 4: 4-[2-(2-Carboxy-ethyl)-3-[6-(5-ethoxy-biphenyl-3-yloxy)-hexyl]-phenoxy]-butyric acid

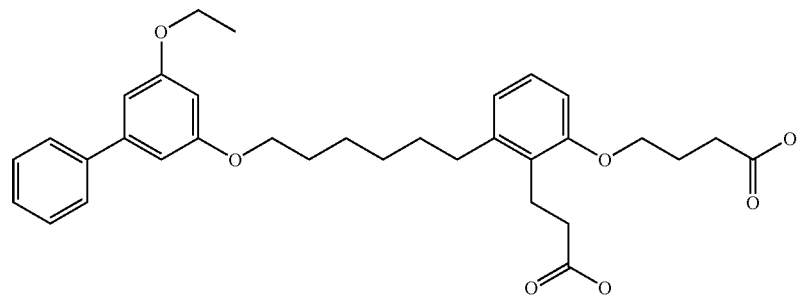

A similar procedure as described in Example 43, step 5 was used, starting from 4-[3-[6-(5-ethoxy-biphenyl-3-yloxy)-hexyl]-2-(2-ethoxycarbonyl-ethyl)-phenoxy]-butyric acid ethyl ester (240 mg, 0.4 mmol) and 1.0 N aqueous sodium hydroxide (4 mL) to afford 4-[2-(2-carboxy-ethyl)-3-[6-(5-ethoxy-biphenyl-3-yloxy)-hexyl]-phenoxy]-butyric acid (210 mg, 96%) as a light brown waxy solid: ES(+)-HRMS m/e calcd for $C_{33}H_{40}O_7$ (M+Na)$^+$ 571.2666. found 571.2665.

Example 45

4-[2-(2-Carboxy-ethyl)-3-[6-(3-ethoxy-5-thiophen-3-yl-phenoxy)-hexyl]-phenoxy]-butyric acid hexyl]-2-(2-ethoxycarbonyl-ethyl)-phenoxy]-butyric acid -ethyl ester (305 mg, 0.5 mmol), 3-thiophenylboronic acid (131 mg, 1.0 mmol), [1,1'-bis(diphenylphosphino)ferrocene]dichloropalladium(II) (55 mg, 0.075 mmol), and cesium carbonate (331 mg, 1.0 mmol) to obtain 4-[2-(2-ethoxycarbonyl-ethyl)-3-[6-(3-ethoxy-5-thiophen-3-yl-phenoxy)-hexyl]-phenoxy]-butyric acid ethyl ester (160 mg, 52%) as a colorless viscous oil: ES(+)-HRMS m/e calcd for $C_{35}H_{46}O_7S$ (M+Na)$^+$ 633.2856. found 633.2860.

Step 2: 4-[2-(2-Carboxy-ethyl)-3-[6-(3-ethoxy-5-thiophen-3-yl-phenoxy)-hexyl]-phenoxy]-butyric acid

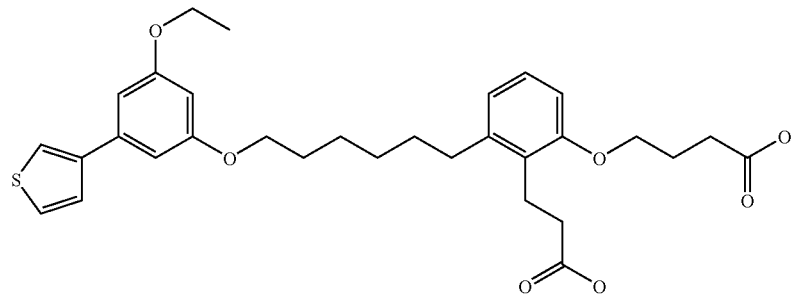

Step 1: 4-[2-(2-Ethoxycarbonyl-ethyl)-3-[6-(3-ethoxy-5-thiophen-3-yl-phenoxy)-hexyl]-phenoxy]-butyric acid ethyl ester

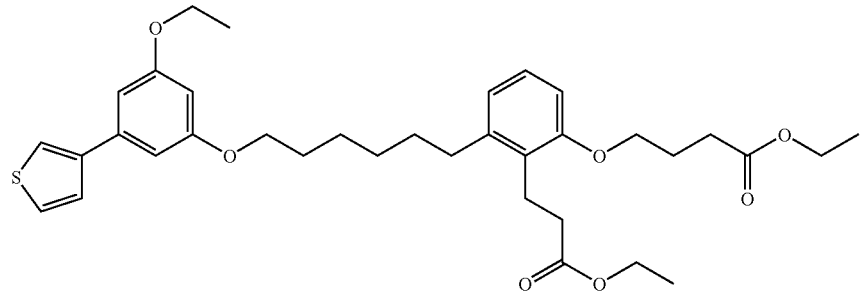

A similar procedure as described in Example 44, step 3 was used, starting from 4-[3-[6-(3-bromo-5-ethoxy-phenoxy)

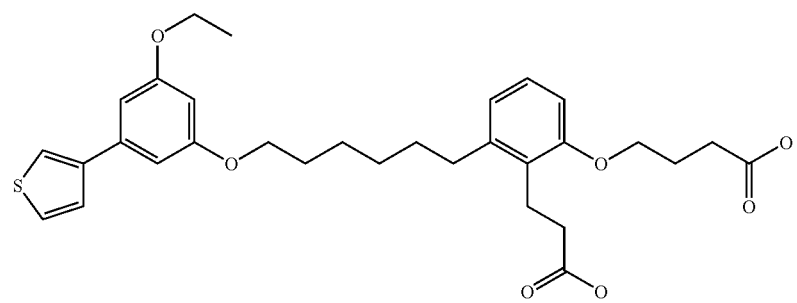

A similar procedure as described in Example 43, step 5 was used, starting from 4-[2-(2-ethoxycarbonyl-ethyl)-3-[6-(3-ethoxy-5-thiophen-3-yl-phenoxy)-hexyl]-phenoxy]-butyric acid ethyl ester (150 mg, 0.25 mmol) and 1.0 N aqueous sodium hydroxide (2.5 mL) to afford 4-[2-(2-carboxy-ethyl)-3-[6-(3-ethoxy-5-thiophen-3-yl-phenoxy)-hexyl]-phenoxy]-butyric acid (136 mg, 99%) as a light brown waxy solid: ES(+)-HRMS m/e calcd for $C_{31}H_{38}O_7S$ (M+H)$^+$ 555.2411, found 555.2410.

rocene]dichloropalladium(II) (55 mg, 0.075 mmol), and cesium carbonate (331 mg, 1.0 mmol) to obtain 4-[3-{6-[3-(2,3-dihydro-benzo[1,4]dioxin-6-yl)-5-ethoxy-phenoxy]-hexyl}-2-(2-ethoxycarbonyl-ethyl)-phenoxy]-butyric acid ethyl ester (76 mg, 23%) as a colorless viscous oil: ES(+)-HRMS m/e calcd for $C_{39}H_{50}O_9$ (M+Na)$^+$ 685.3347. found 685.3353.

Example 46

4-[2-(2-Carboxy-ethyl)-3-{6-[3-(2,3-dihydro-benzo[1,4]dioxin-6-yl)-5-ethoxy-phenoxy]-hexyl}-phenoxy]-butyric acid Step 2: 4-[2-(2-Carboxy-ethyl)-3-{6-[3-(2,3-dihydro-benzo[1,4]dioxin-6-yl)-5-ethoxy-phenoxy]-hexyl}-phenoxy]-butyric acid

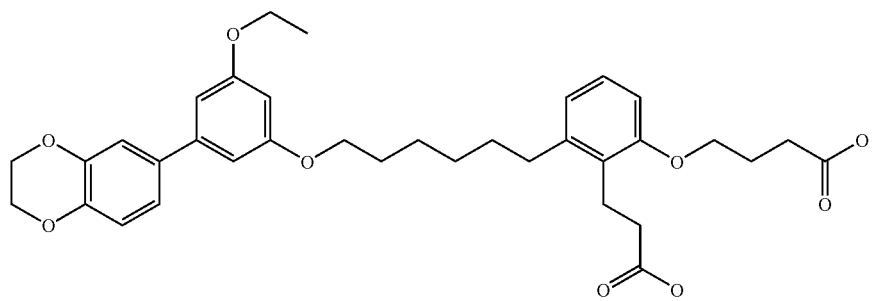

Step 1: 4-[3-{6-[3-(2,3-Dihydro-benzo[1,4]-dioxin-6-yl)-5-ethoxy-phenoxy]-hexyl}-2-(2-ethoxycarbonyl-ethyl)-phenoxy]-butyric acid ethyl ester

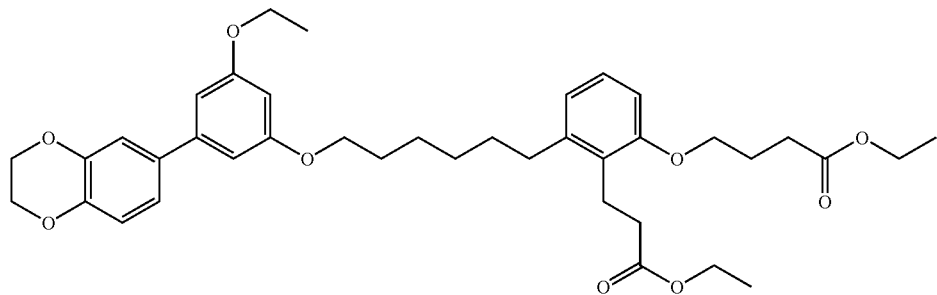

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid ethyl ester (305 mg, 0.5 mmol), 1,4-benzodioxane-6-boronic acid (184 mg, 1.0 mmol), [1,1'-bis(diphenylphosphino)fer-

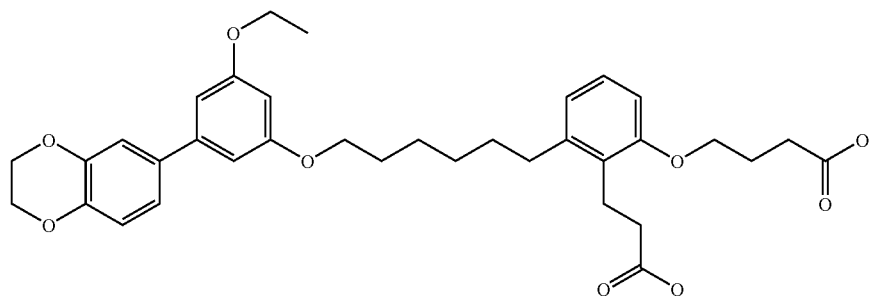

A similar procedure as described in Example 43, step 5 was used, starting from 4-[3-{6-[3-(2,3-dihydro-benzo[1,4]dioxin-6-yl)-5-ethoxy-phenoxy]-hexyl}-2-(2-ethoxycarbonylethyl)-phenoxy]-butyric acid ethyl ester (70 mg, 0.1 mmol) and 1.0 N aqueous sodium hydroxide (1 mL) to afford 4-[2-(2-carboxy-ethyl)-3-{6-[3-(2,3-dihydro-benzo[1,4]dioxin-6-yl)-5-ethoxy-phenoxy]-hexyl}-phenoxy]-butyric acid (62 mg, 99%) as a light brown waxy solid: ES(+)-HRMS m/e calcd for $C_{35}H_{42}O_9$ (M+Na)$^+$ 629.2721. found 629.2721.

bonate (331 mg, 1.0 mmol) to obtain 4-[2-(2-ethoxycarbonyl-ethyl)-3-[6-(5-ethoxy-3'-fluoro-biphenyl-3-yloxy)-hexyl]-phenoxy]-butyric acid ethyl ester (220 mg, 70%) as a colorless viscous oil: ES(+)-HRMS m/e calcd for $C_{37}H_{47}FO_7$ (M+Na)$^+$ 645.3198. found 645.3198.

Example 47

4-[2-(2-Carboxy-ethyl)-3-[6-(5-ethoxy-3'-fluoro-biphenyl-3-yloxy)-hexyl]-phenoxy]-butyric acid Step 2: 4-[2-(2-Carboxy-ethyl)-3-[6-(5-ethoxy-3'-fluoro-biphenyl-3-yloxy)-hexyl]-phenoxy]-butyric acid

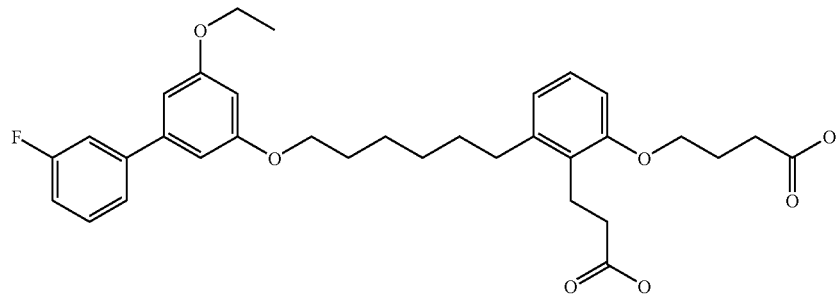

Step 1: 4-[2-(2-Ethoxycarbonyl-ethyl)-3-[6-(5-ethoxy-3'-fluoro-biphenyl-3-yloxy)-hexyl]-phenoxy]-butyric acid ethyl ester

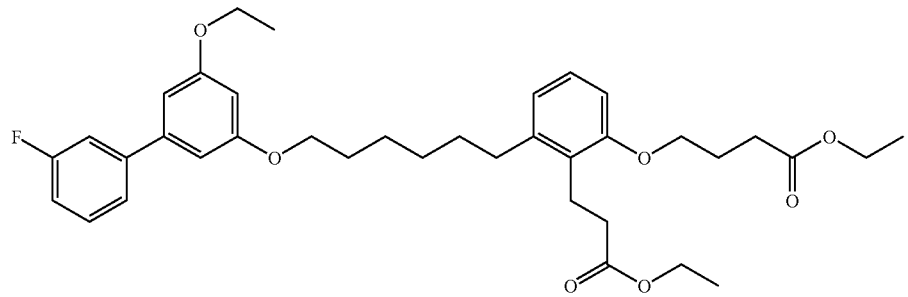

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid

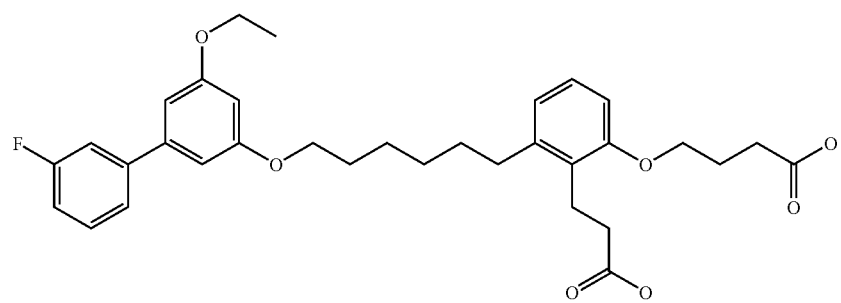

ethyl ester (305 mg, 0.5 mmol), 3-fluoro-phenylboronic acid (142 mg, 1.0 mmol), [1,1'-bis(diphenylphosphino)ferrocene]dichloropalladium(II) (55 mg, 0.075 mmol), and cesium car- A similar procedure as described in Example 43, step 5 was used, starting from 4-[2-(2-ethoxycarbonyl-ethyl)-3-[6-(5-ethoxy-3'-fluoro-biphenyl-3-yloxy)-hexyl]-phenoxy]-butyric acid ethyl ester (210 mg, 0.34 mmol) and 1.0 N aqueous sodium hydroxide (3.4 mL) to afford 4-[2-(2-carboxy-ethyl)-3-[6-(5-ethoxy-3'-fluoro-biphenyl-3-yloxy)-hexyl]-phenoxy]-butyric acid (190 mg, 99%) as a light brown waxy solid: ES(+)-HRMS m/e calcd for $C_{33}H_{39}FO_7$ (M+Na)$^+$ 589.2572. found 589.2573.

Example 48

4-[2-Carboxy-ethyl)-3-[6-(5-ethoxy-4'-fluoro-biphenyl-3-yloxy)-hexyl]-phenoxy]-butyric acid

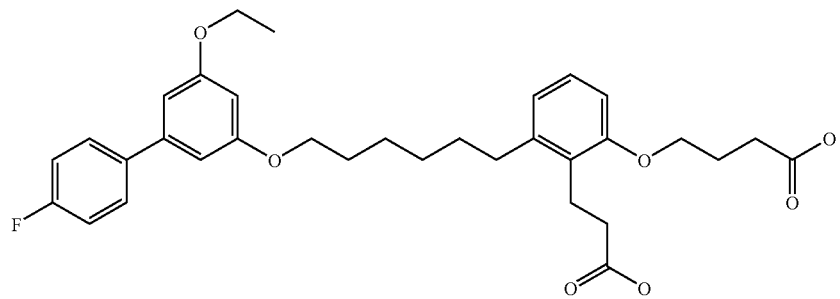

Step 1: 4-[2-(2-Ethoxycarbonyl-ethyl)-3-[6-(5-ethoxy-4'-fluoro-biphenyl-3-yloxy)-hexyl]-phenoxy]-butyric acid ethyl ester

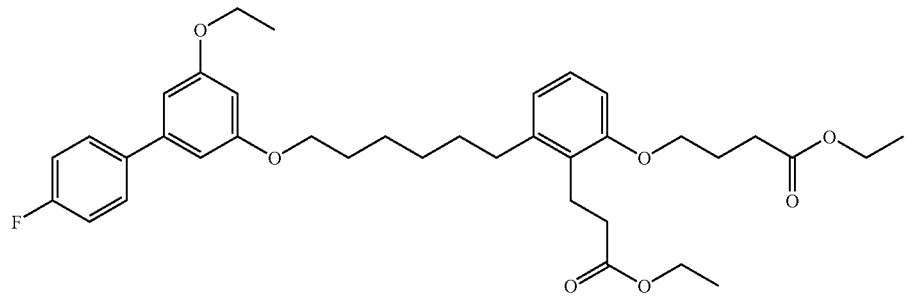

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid ethyl ester (305 mg, 0.5 mmol), 4-fluoro-phenylboronic acid (141 mg, 1.0 mmol), [1,1'-bis(diphenylphosphino)ferrocene]dichloropalladium(II) (55 mg, 0.075 mmol), and cesium carbonate (331 mg, 1.0 mmol) to obtain 4-[2-(2-ethoxycarbonyl-ethyl)-3-[6-(5-ethoxy-4'-fluoro-biphenyl-3-yloxy)-hexyl]-phenoxy]-butyric acid ethyl ester (161 mg, 52%) as a colorless viscous oil: ES(+)-HRMS m/e calcd for $C_{37}H_{47}FO_7$ (M+Na)$^+$ 645.3198. found 645.3196.

Step 2: 4-[2-(2-Carboxy-ethyl)-3-[6-(5-ethoxy-4'-fluoro-biphenyl-3-yloxy)-hexyl]-phenoxy]-butyric acid

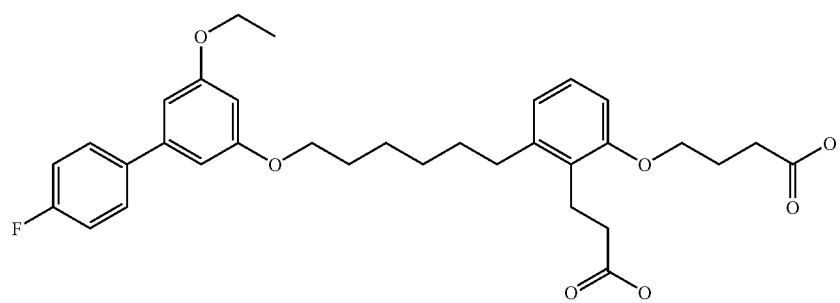

A similar procedure as described in Example 43, step 5 was used, starting from 4-[2-(2-ethoxycarbonyl-ethyl)-3-[6-(5-ethoxy-4'-fluoro-biphenyl-3-yloxy)-hexyl]-phenoxy]-bu tyric acid ethyl ester (150 mg, 0.24 mmol) and 1.0 N aqueous sodium hydroxide (2.4 mL) to afford 4-[2-(2-carboxy-ethyl)-3-[6-(5-ethoxy-4'-fluoro-biphenyl-3-yloxy)-hexyl]-phenoxy]-butyric acid (135 mg, 99%) as a light brown waxy solid: ES(+)-HRMS m/e calcd for $C_{33}H_{39}FO_7$ (M+Na)$^+$ 589.2572. found 589.2573.

Example 49

4-[2-(2-Carboxy-ethyl)-3-[6-(4'-chloro-5-ethoxy-biphenyl-3-yloxy)-hexyl]-phenoxy]-butyric acid

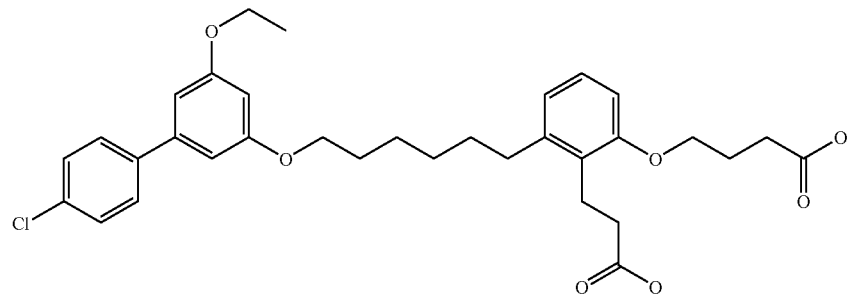

Step 1: 4-[3-[6-(4'-Chloro-5-ethoxy-biphenyl-3-yloxy)-hexyl]-2-(2-ethoxycarbonyl-ethyl)-phenoxy]-butyric acid ethyl ester

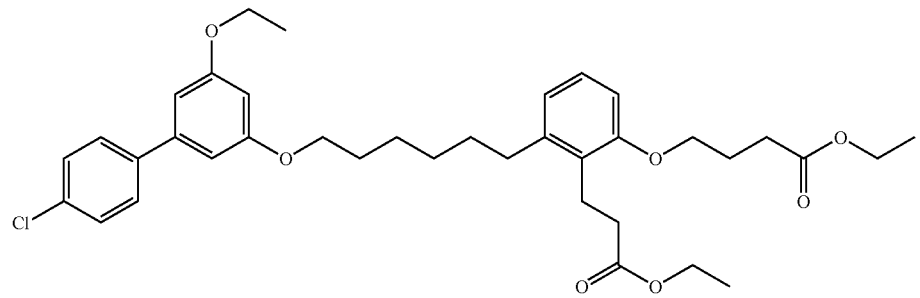

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid ethyl ester (305 mg, 0.5 mmol), 4-chloro-phenylboronic acid (165 mg, 1.0 mmol), [1,1'-bis(diphenylphosphino)ferrocene]dichloropalladium(II) (55 mg, 0.075 mmol), and cesium carbonate (331 mg, 1.0 mmol) to obtain 4-[3-[6-(4'-chloro-5-ethoxy-biphenyl-3-yloxy)-hexyl]-2-(2-ethoxycarbonyl-ethyl)-phenoxy]-butyric acid ethyl ester (231 mg, 72%) as a colorless viscous oil: ES(+)-HRMS m/e calcd for $C_{37}H_{47}ClO_7$ (M+Na)$^+$ 661.2902. found 661.2905.

Step 2: 4-[2-(2-Carboxy-ethyl)-3-[6-(4'-chloro-5-ethoxy-biphenyl-3-yloxy)-hexyl]-phenoxy]-butyric acid

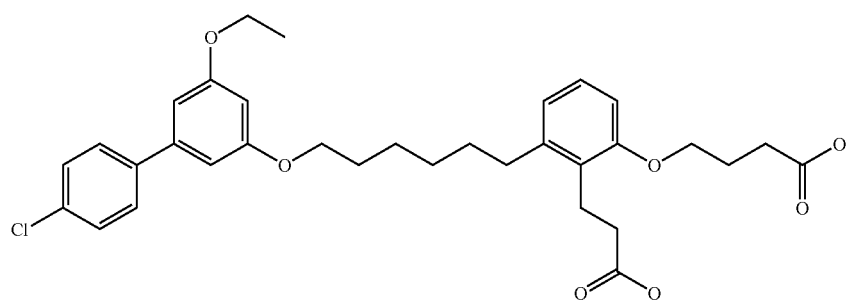

A similar procedure as described in Example 43, step 5 was used, starting from 4-[3-[6-(4'-chloro-5-ethoxy-biphenyl-3-yloxy)-hexyl]-2-(2-ethoxycarbonyl-ethyl)-phenoxy]-butyric acid ethyl ester (150 mg, 0.24 mmol) and 1.0 N aqueous sodium hydroxide (2.4 mL) to afford 4-[2-(2-carboxy-ethyl)-3-[6-(4'-chloro-5-ethoxy-biphenyl-3-yloxy)-hexyl]-phenoxy]-butyric acid (200 mg, 98%) as a light brown waxy solid: ES(+)-HRMS m/e calcd for $C_{33}H_{39}ClO_7$ (M+Na)$^+$ 605.2276. found 605.2278.

Example 50

4-[2-(2-Carboxy-ethyl)-3-[6-(3',4'-difluoro-5-ethoxy-biphenyl-3-yloxy)-hexyl]-phenoxy]-butyric acid cesium carbonate (331 mg, 1.0 mmol) to obtain 4-[2-(2-ethoxycarbonyl-ethyl)-3-[6-(3',4'-difluoro-5-ethoxy-biphenyl-3-yloxy)-hexyl]-phenoxy]-butyric acid ethyl ester (75 mg, 23%) as a colorless viscous oil: ES(+)-HRMS m/e calcd for $C_{37}H_{46}F_2O_7$ (M+Na)$^+$ 663.3104. found 663.3102.

Step 2: 4-[2-(2-Carboxy-ethyl)-3-[6-(3',4'-difluoro-5-ethoxy-biphenyl-3-yloxy)-hexyl]-phenoxy]-butyric acid

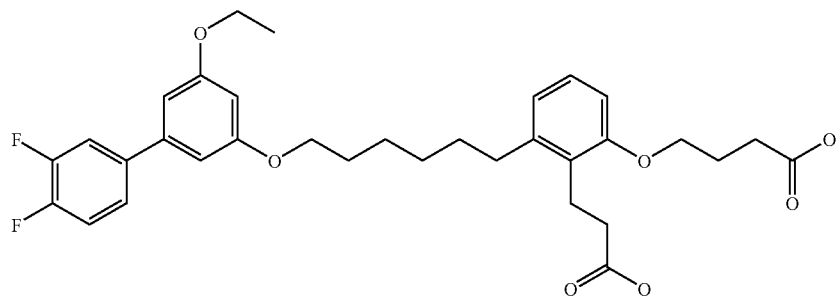

Step 1: 4-[2-(2-Ethoxycarbonyl-ethyl)-3-[6-(3',4'-difluoro-5-ethoxy-biphenyl-3-yloxy)-hexyl]-phenoxy]-butyric acid ethyl ester

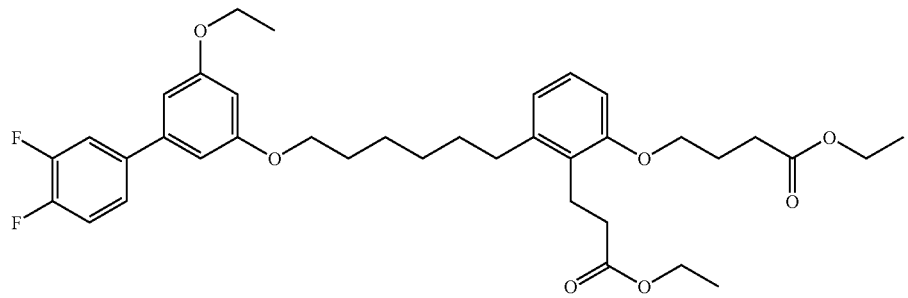

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid

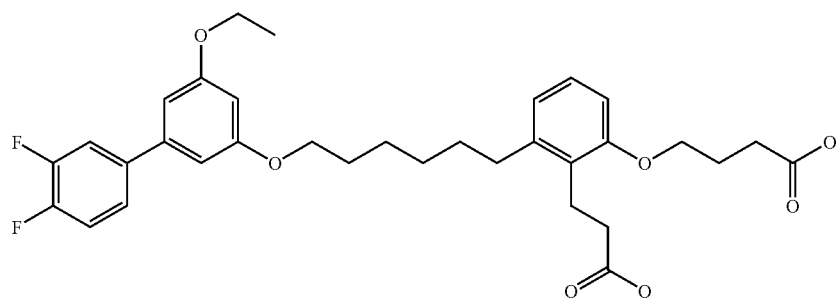

ethyl ester (305 mg, 0.5 mmol), 3,4-difluoro-phenylboronic acid (164 mg, 1.0 mmol), [1,1'-bis(diphenylphosphino)ferrocene]dichloropalladium(II) (55 mg, 0.075 mmol), and A similar procedure as described in Example 43, step 5 was used, starting from 4-[2-(2-ethoxycarbonyl-ethyl)-3-[6-(3',4'-difluoro-5-ethoxy-biphenyl-3-yloxy)-hexyl]-phenoxy]- butyric acid ethyl ester (65 mg, 0.1 mmol) and 1.0 N aqueous sodium hydroxide (1.0 mL) to afford 4-[2-(2-carboxy-ethyl)-3-[6-(3',4'-difluoro-5-ethoxy-biphenyl-3-yloxy)-hexyl]-phenoxy]-butyric acid (58 mg, 98%) as a light brown waxy solid: ES(+)-HRMS m/e calcd for $C_{33}H_{38}F_2O_7$ (M+Na)$^+$ 607.2478. found 607.2481.

Example 51

4-[2-(2-Carboxy-ethyl)-3-[6-(5-ethoxy-4'-methanesulfonyl-biphenyl-3-yloxy)-hexyl]-phenoxy]-butyric acid

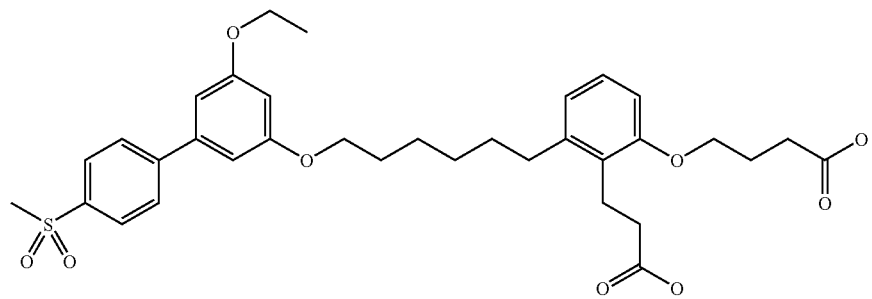

hexyl]-2-(2-ethoxycarbonyl-ethyl)-phenoxy]-butyric acid ethyl ester (305 mg, 0.5 mmol), 4-methanesulfonyl-phenyl-boronic acid (207 mg, 1.0 mmol), [1,1'-bis(diphenylphosphino)ferrocene]dichloropalladium(II) (55 mg, 0.075 mmol), and cesium carbonate (331 mg, 1.0 mmol) to obtain 4-[2-(2-ethoxycarbonyl-ethyl)-3-[6-(5-ethoxy-4'-methanesulfonyl-biphenyl-3-yloxy)-hexyl]-phenoxy]-butyric acid ethyl ester (57 mg, 17%) as a light brown oil: ES(+)-HRMS m/e calcd for $C_{38}H_{50}O_9S$ (M+Na)$^+$ 705.3068. found 705.3065.

Step 1: 4-[2-(2-Ethoxycarbonyl-ethyl)-3-[6-(5-ethoxy-4'-methanesulfonyl-biphenyl-3-yloxy)-hexyl]-phenoxy]-butyric acid ethyl ester Step 2: 4-[2-(2-Carboxy-ethyl)-3-[6-(5-ethoxy-4'-methanesulfonyl-biphenyl-3-yloxy)-hexyl]-phenoxy]-butyric acid

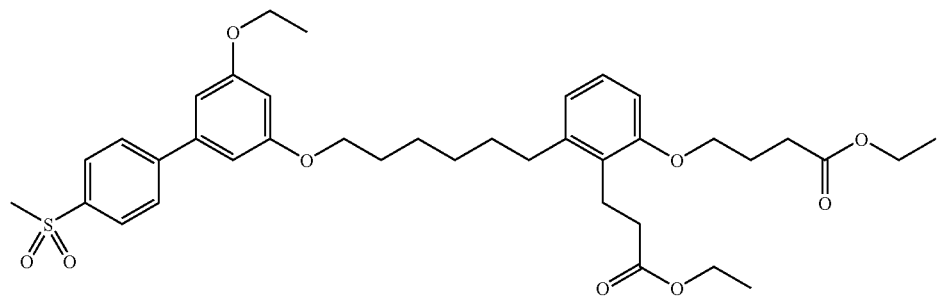

A similar procedure as described in Example 44, step 3 was used, starting from 4-[3-[6-(3-bromo-5-ethoxy-phenoxy)-

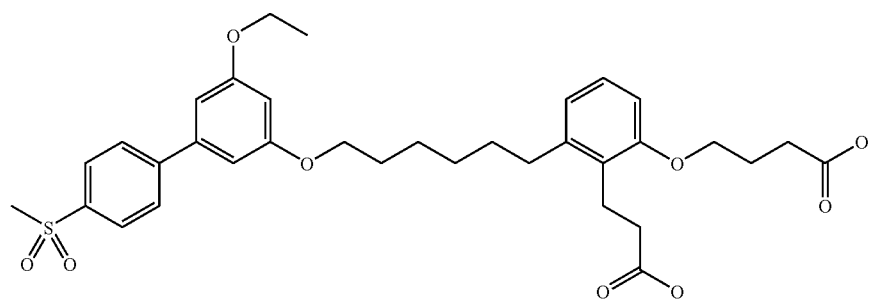

A similar procedure as described in Example 43, step 5 was used, starting from 4-[2-(2-ethoxycarbonyl-ethyl)-3-[6-(5-ethoxy-4'-methanesulfonyl-biphenyl-3-yloxy)-hexyl]-phenoxy]-butyric acid ethyl ester (52 mg, 0.076 mmol) and 1.0 N aqueous sodium hydroxide (1.0 mL) to afford 4-[2-(2-carboxy-ethyl)-3-[6-(5-ethoxy-4'-methanesulfonyl-biphenyl-3-yloxy)-hexyl]-phenoxy]-butyric acid (44 mg, 91%) as a light brown solid: ES(+)-HRMS m/e calcd for $C_{34}H_{42}O_9S$ (M+Na)$^+$ 649.2442. found 649.2442.

Example 52

4-[2-(2-Carboxy-ethyl)-3-[6-[3-(2-chloro-pyridin-4-yl)-5-ethoxy-phenoxy]-hexyl]-phenoxy]-butyric acid hexyl]-2-(2-ethoxycarbonyl-ethyl)-phenoxy]-butyric acid ethyl ester (305 mg, 0.5 mmol), 2-chloro-pyridin-4-ylboronic acid (161 mg, 1.0 mmol), [1,1'-bis(diphenylphosphino)ferrocene]dichloropalladium(II) (55 mg, 0.075 mmol), and cesium carbonate (331 mg, 1.0 mmol) to obtain 4-[3-{6-[3-(2-chloro-pyridin-4-yl)-5-ethoxy-phenoxy]-hexyl}-2-(2-ethoxycarbonyl-ethyl)-phenoxy]-butyric acid ethyl ester (115 mg, 36%) as a light yellow oil: ES(+)-HRMS m/e calcd for $C_{36}H_{46}ClNO_7$ (M+H)$^+$ 640.3036. found 640.3032.

Step 2: 4-[2-(2-Carboxy-ethyl)-3-[6-[3-(2-chloro-pyridin-4-yl)-5-ethoxy-phenoxy]-hexyl]-phenoxy]-butyric acid

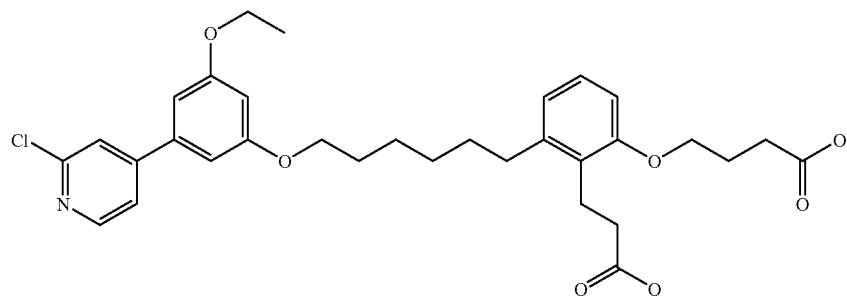

Step 1: 4-[3-{6-[3-(2-Chloro-pyridin-4-yl)-5-ethoxy-phenoxy]-hexyl}-2-(2-ethoxycarbonyl-ethyl)-phenoxy]-butyric acid ethyl ester

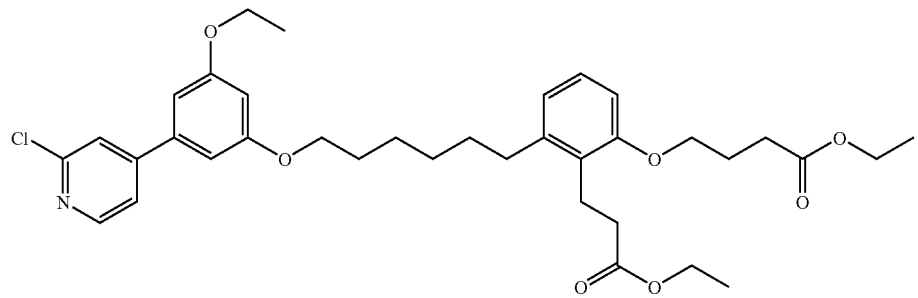

A similar procedure as described in Example 44, step 3 was used, starting from 4-[3-[6-(3-bromo-5-ethoxy-phenoxy)-

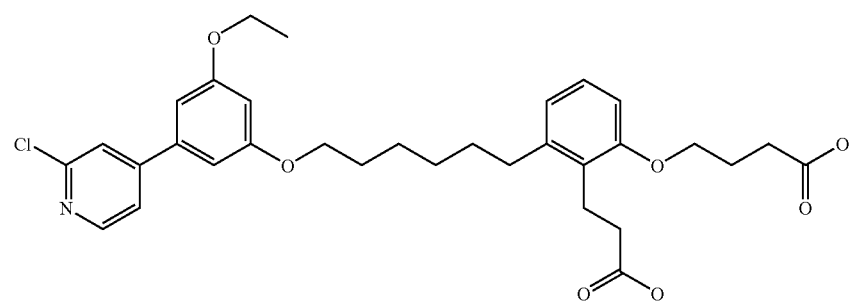

A similar procedure as described in Example 43, step 5 was used, starting from 4-[3-{6-[3-(2-chloro-pyridin-4-yl)-5-ethoxy-phenoxy]-hexyl}-2-(2-ethoxycarbonyl-ethyl)-phenoxy]-butyric acid ethyl ester (105 mg, 0.16 mmol) and 1.0 N aqueous sodium hydroxide (1.6 mL) to afford 4-[2-(2-carboxy-ethyl)-3-[6-[3-(2-chloro-pyridin-4-yl)-5-ethoxy-phenoxy]-hexyl]-phenoxy]-butyric acid (92 mg, 96%) as a light brown solid: ES(+)-HRMS m/e calcd for $C_{32}H_{38}ClNO_7$ $(M+H)^+$ 584.2410. found 584.2412.

Example 53

4-[2-(2-Carboxy-ethyl)-3-[6-(3-ethoxy-5-pyrimidin-5-yl-phenoxy)-hexyl]-phenoxy]-butyric acid

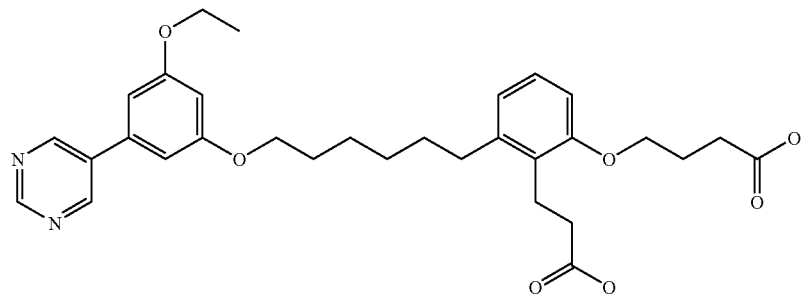

Step 1: 4-[2-(2-Ethoxycarbonyl-ethyl)-3-[6-(3-ethoxy-5-pyrimidin-5-yl-phenoxy)-hexyl]-phenoxy]-butyric acid ethyl ester

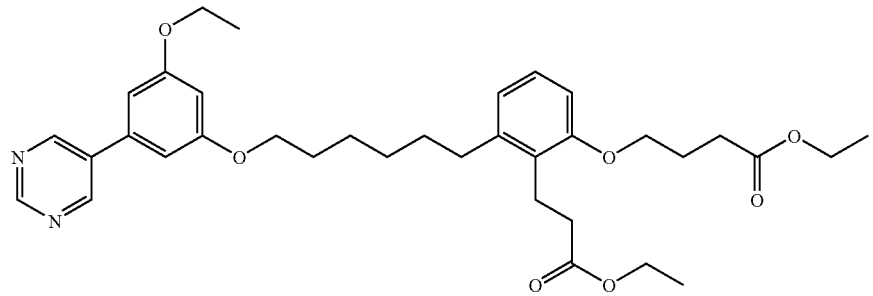

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid ethyl ester (305 mg, 0.5 mmol), pyrimidin-5-ylboronic acid (124 mg, 1.0 mmol), [1,1'-bis(diphenylphosphino)ferrocene] dichloropalladium(II) (55 mg, 0.075 mmol), and cesium carbonate (331 mg, 1.0 mmol) to obtain 4-[2-(2-ethoxycarbonyl-ethyl)-3-[6-(3-ethoxy-5-pyrimidin-5-yl-phenoxy)-hexyl]-phenoxy]-butyric acid ethyl ester (94 mg, 31%) as a light brown oil: ES(+)-HRMS m/e calcd for $C_{35}H_{46}N_2O_7$ $(M+H)^+$ 607.3378. found 607.3379.

Step 2: 4-[2-(2-Carboxy-ethyl)-3-[6-(3-ethoxy-5-pyrimidin-5-yl-phenoxy)-hexyl]-phenoxy]-butyric acid

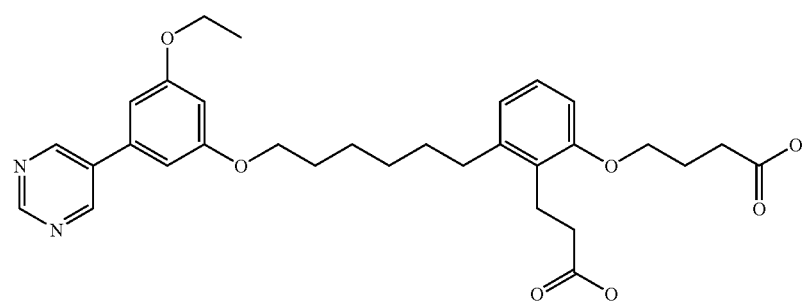

A similar procedure as described in Example 43, step 5 was used, starting from 4-[2-(2-ethoxycarbonyl-ethyl)-3-[6-(3-ethoxy-5-pyrimidin-5-yl-phenoxy)-hexyl]-phenoxy]-butyric acid ethyl ester (76 mg, 0.13 mmol) and 1.0 N aqueous sodium hydroxide (1.3 mL) to afford 4-[2-(2-carboxy-ethyl)-3-[6-(3-ethoxy-5-yl-phenoxy)-hexyl]-phenoxy]-butyric acid (63 mg, 92%) as a light brown solid: ES(+)-HRMS m/e calcd for $C_{31}H_{38}N_2O_7$ (M+H)$^+$ 551.2752. found 551.2750.

Example 54

4-[2-(2-Carboxy-ethyl)-3-{6-[3-ethoxy-5-(1H-indol-5-yl)-phenoxy]-hexyl}-phenoxy]-butyric acid

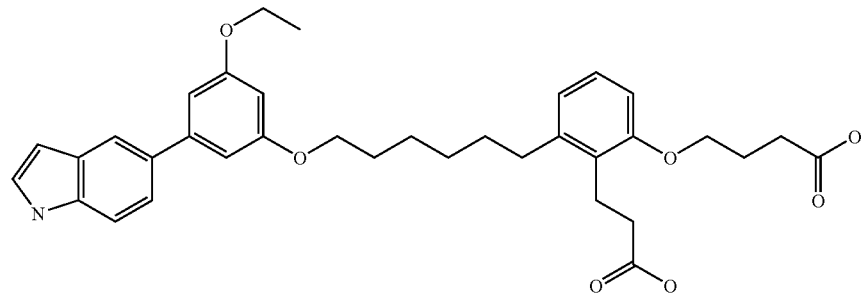

Step 1: 4-[2-(2-Ethoxycarbonyl-ethyl)-3-{6-[3-ethoxy-5-(1H-indol-5-yl)-phenoxy]-hexyl}-phenoxy]-butyric acid ethyl ester

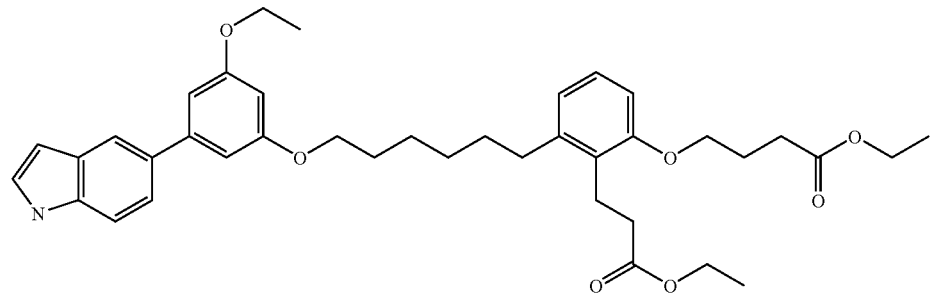

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid ethyl ester (305 mg, 0.5 mmol), 5-indolineboronic acid (170 mg, 1.0 mmol), [1,1'-bis(diphenylphosphino)ferrocene]dichloropalladium(II) (55 mg, 0.075 mmol), and cesium carbonate (331 mg, 1.0 mmol) to obtain 4-[2-(2-ethoxycarbonyl-ethyl)-3-{6-[3-ethoxy-5-(1H-indol-5-yl)-phenoxy]-hexyl}-phenoxy]-butyric acid ethyl ester (25 mg, 8%) as a light yellow oil: ES(+)-HRMS m/e calcd for $C_{39}H_{49}NO_7$ (M+Na)$^+$ 666.3401. found 666.3399.

Step 2: 4-[2-(2-Carboxy-ethyl)-3-{6-[3-ethoxy-5-(1H-indol-5-yl)-phenoxy]-hexyl}-phenoxy]-butyric acid

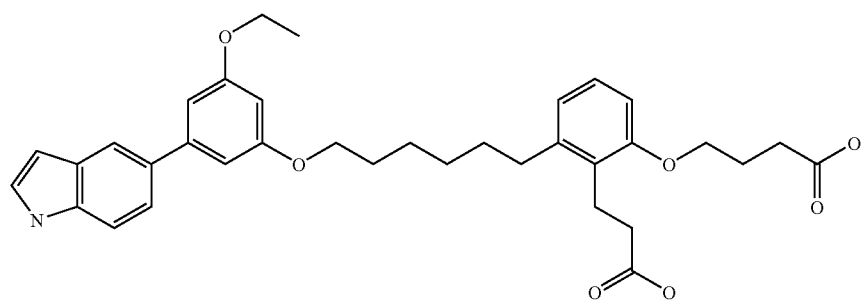

A similar procedure as described in Example 43, step 5 was used, starting from 4-[2-(2-ethoxycarbonyl-ethyl)-3-{6-[3-ethoxy-5-(1H-indol-5-yl)-phenoxy]-hexyl}-phenoxy]-butyric acid ethyl ester (24 mg, 0.04 mmol) and 1.0 N aqueous sodium hydroxide (0.4 mL) to afford 4-[2-(2-carboxy-ethyl)-3-{6-[3-ethoxy-5-(1H-indol-5-yl)-phenoxy]-hexyl}-phenoxy]-butyric acid (20 mg, 91%) as a light brown solid: ES(+)-HRMS m/e calcd for $C_{35}H_{41}NO_7$ (M+Na)$^+$ 610.2775, found 610.2773.

Example 55

4-[2-(2-Carboxy-ethyl)-3-{6-[3-ethoxy-5-(1H-indol-6-yl)-phenoxy]-hexyl}-phenoxy]-butyric acid bonate (331 mg, 1.0 mmol) to obtain 4-[2-(2-ethoxycarbonyl-ethyl)-3-{6-[3-ethoxy-5-(1H-indol-6-yl)-phenoxy]-hexyl}-phenoxy]-butyric acid ethyl ester (125 mg, 39%) as a light yellow oil: ES(+)-HRMS m/e calcd for $C_{39}H_{49}NO_7$ (M+Na)$^+$ 666.3401. found 666.3396.

Step 2: 4-[2-(2-Carboxy-ethyl)-3-{6-[3-ethoxy-5-(1H-indol-6-yl)-phenoxy]-hexyl}-phenoxy]-butyric acid

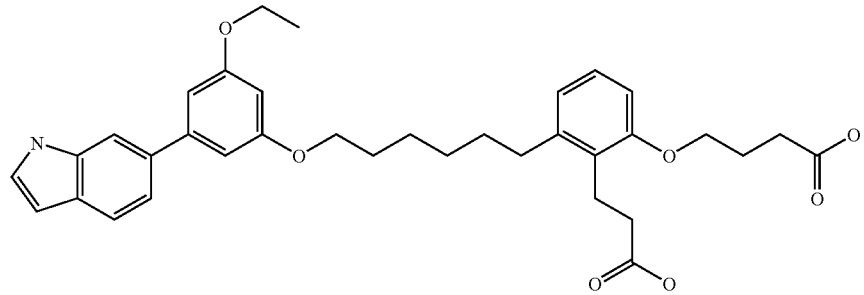

Step 1: 4-[2-(2-Ethoxycarbonyl-ethyl)-3-{6-[3-ethoxy-5-(1H-indol-6-yl)-phenoxy]-hexyl}-phenoxy]-butyric acid ethyl ester

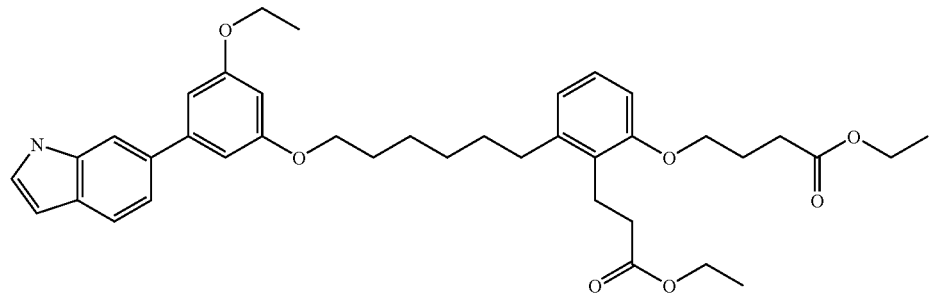

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid

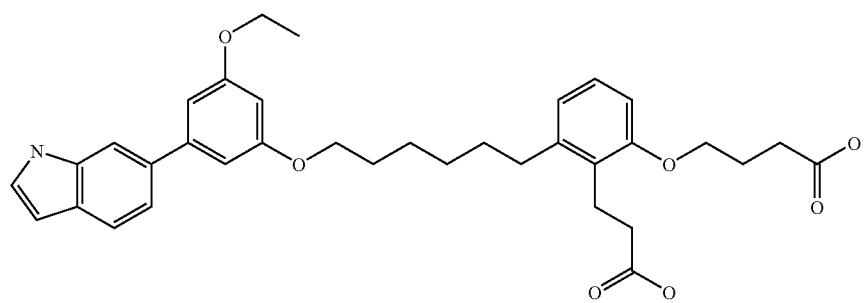

ethyl ester (305 mg, 0.5 mmol), 6-indolineboronic acid (170 mg, 1.0 mmol), [1,1'-bis(diphenylphosphino)ferrocene]dichloropalladium(II) (55 mg, 0.075 mmol), and cesium car- A similar procedure as described in Example 43, step 5 was used, starting from 4-[2-(2-ethoxycarbonyl-ethyl)-3-{6-[3-ethoxy-5-(1H-indol-6-yl)-phenoxy]-hexyl}-phenoxy]-bu tyric acid ethyl ester (111 mg, 0.17 mmol) and 1.0 N aqueous sodium hydroxide (1.7 mL) to afford 4-[2-(2-carboxy-ethyl)-3-{6-[3-ethoxy-5-(1H-indol-6-yl)-phenoxy]-hexyl}-phenoxy]-butyric acid (79 mg, 78%) as a light brown solid: ES(+)-HRMS m/e calcd for $C_{35}H_{41}NO_7$ (M+Na)$^+$ 610.2775, found 610.2774.

Example 56

4-[3-{6-[3-Benzothiazol-5-yl-5-ethoxy-phenoxy]-hexyl}-2-(2-carboxy-ethyl)-phenoxy]-butyric acid

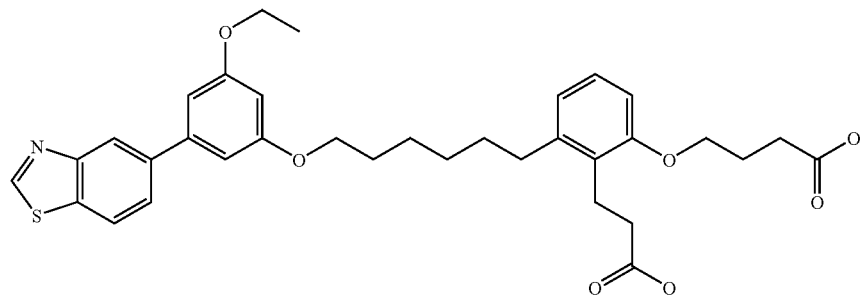

Step 1: 4-[3-{6-(3-Benzothiazol-5-yl-5-ethoxy-phenoxy)-hexyl}-2-(2-ethoxycarbonyl-ethyl)-phenoxy]-butyric acid ethyl ester

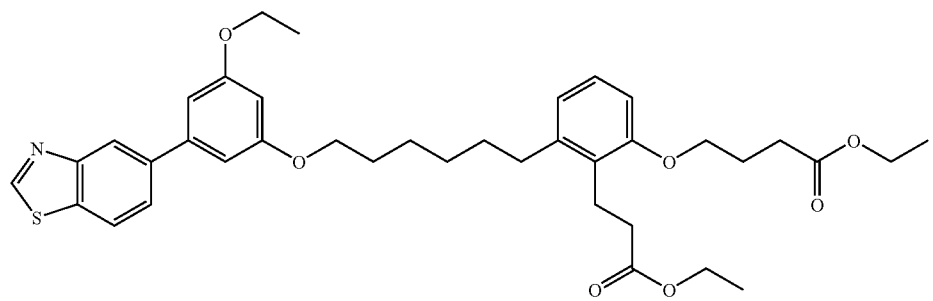

To a suspension of palladium(II) acetate (11.32 mg, 0.05 mmol), triphenyphosphine (26.2 mg, 0.1 mmol), and benzothiazol-5-yl pinacolboronate (258 mg, 0.99 mmol) in dioxane (7.5 mL) were added 4-[3-[6-(3-bromo-5-ethoxy-phenoxy)-hexyl]-2-(2-ethoxycarbonyl-ethyl)-phenoxy]-butyric acid ethyl ester (300 mg, 0.49 mmol), potassium phosphate (216 mg, 0.99 mmol), and pure water (15 mg, 0.99 mmol) at room temperature. Then, the resulting mixture was heated to 100° C. for 2 h. Then, the reaction mixture was cooled to room temperature and diluted with water (50 mL) and ethyl acetate (50 mL). The two layers were separated and the aqueous layer was extracted with ethyl acetate (50 mL) and the combined organic extracts were washed with water (50 mL) and brine solution (50 mL). The organic layer was dried over anhydrous magnesium sulfate and filtration of the drying agent and removal of the solvent under vacuum gave the colored residue which was purified by using an ISCO 40 g column, eluting with 2-25% ethyl acetate in hexanes to obtain 4-[3-{6-(3-benzothiazol-5-yl-5-ethoxy-phenoxy)-hexyl}-2-(2-ethoxycarbonyl-ethyl)-phenoxy]-butyric acid ethyl ester (61 mg, 99%) as a off-white solid: ES(+)-LRMS m/e calcd for $C_{38}H_{47}NO_7S$ (M+H)$^+$ 662.3146. found 662.3144.

Step 2: 4-[3-{6-[3-Benzothiazol-5-yl-5-ethoxy-phenoxy]-hexyl}-2-(2-carboxy-ethyl)-phenoxy]-butyric acid

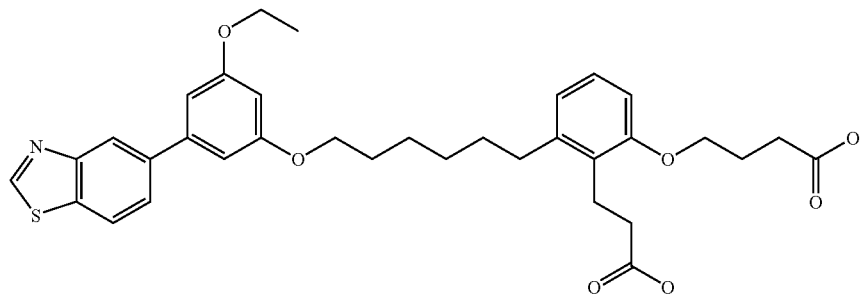

A similar procedure as described in Example 43, step 5 was used, starting from 4-[3-{6-(3-benzothiazol-5-yl-5-ethoxy-phenoxy)-hexyl}-2-(2-ethoxycarbonyl-ethyl)-phenoxy]-butyric acid ethyl ester (61 mg, 0.17 mmol) and 1.0 N aqueous sodium hydroxide (1.0 mL) to afford 4-[3-{6-[3-benzothiazol-5-yl-5-ethoxy-phenoxy]-hexyl}-2-(2-carboxy-ethyl)-phenoxy]-butyric acid (9.2 mg, 17%) as a light brown solid: ES(+)-HRMS m/e calcd for $C_{34}H_{39}NO_7S$ (M+H)$^+$ 606.2520. found 606.2523.

Example 57

4-(2-(2-Carboxy-ethyl)-3-{6-[3-(2,2-difluoro-benzo[1,3]dioxol-5-yl)-5-ethoxy-phenoxy]-hexyl}-phenoxy)-butyric acid

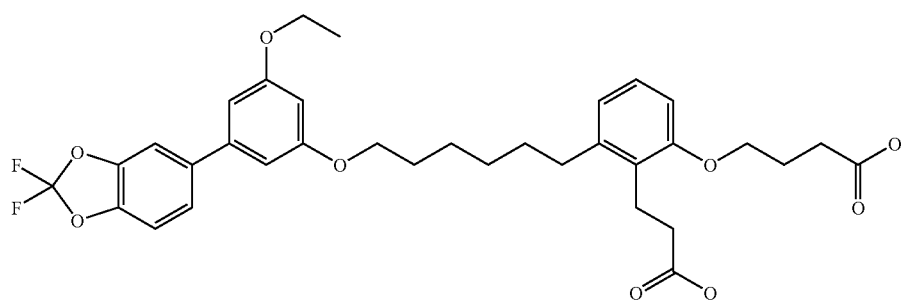

Step 1: 2,2-Difluoro-benzo[1,3]dioxole-5-boronic acid

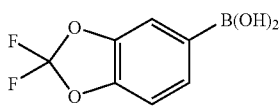

n-BuLi in hexanes (2.5 M solution, 46 mL) was added to anhydrous THF (250 mL) cooled in acetone-dry ice bath under the flow of nitrogen. After 10 min 5-bromo-2,2-difluoro-1,3-benzodioxole (25.0 g) was added dropwise and the resulting solution was stirred for 30 min. Then, boron isopropoxide (30 mL) was added dropwise and the reaction mixture was allowed to reach room temperature over a period of 3 h. Then acetic acid (30 mL) was added in one portion and the resulting mixture was stirred at room temperature for 10 min. The reaction mixture was then diluted with ethyl acetate and washed with water and brine. The organic extract was dried over anhydrous sodium sulfate and concentrated under reduced pressure. The title compound was obtained by trituration with hexanes as a white solid (14.2 g, 73% yield). HRMS calcd for $C_7H_5O_4BF_2$ [2M–H—H$_2$O]$^-$ 385.0324, observed 385.0319.

Step 2: 4-[3-{6-[3-(2,2-Difluoro-benzo[1,3]dioxol-5-yl)-5-ethoxy-phenoxy)-hexyl}-2-(2-ethoxycarbonyl-ethyl)-phenoxy]-butyric acid ethyl ester

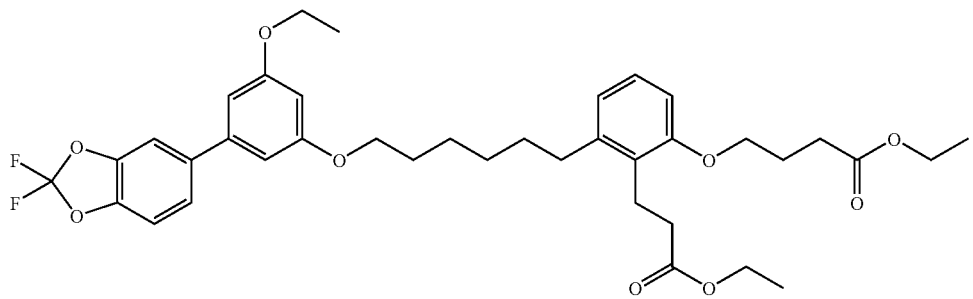

A similar procedure as described in Example 44, step 3 was used, starting from 4-[3-[6-(3-bromo-5-ethoxy-phenoxy)-hexyl]-2-(2-ethoxycarbonyl-ethyl)-phenoxy]-butyric acid ethyl ester (577 mg, 0.95 mmol), 2,2-difluoro-benzo[1,3]dioxo-5-ylboronic acid trimer (524 mg, 0.95 mmol), [1,1'-bis(diphenylphosphino)ferrocene]dichloropalladium(II) (104 mg, 0.14 mmol), and cesium carbonate (625 mg, 1.9 mmol) to obtain 4-[3-{6-[3-(2,2-difluoro-benzo[1,3]dioxol-5-yl)-5-ethoxy-phenoxy)-hexyl}-2-(2-ethoxycarbonyl-ethyl)-phenoxy]-butyric acid ethyl ester (410 mg, 63%) as a colorless viscous oil: ES(+)-HRMS m/e calcd for $C_{38}H_{46}F_2O_9$ $(M+H)^+$ 685.3183, found 685.3180.

Step 3: 4-(2-(2-Carboxy-ethyl)-3-{6-[3-(2,2-difluoro-benzo[1,3]dioxol-5-yl)-5-ethoxy-phenoxy]-hexyl}-phenoxy)-butyric acid

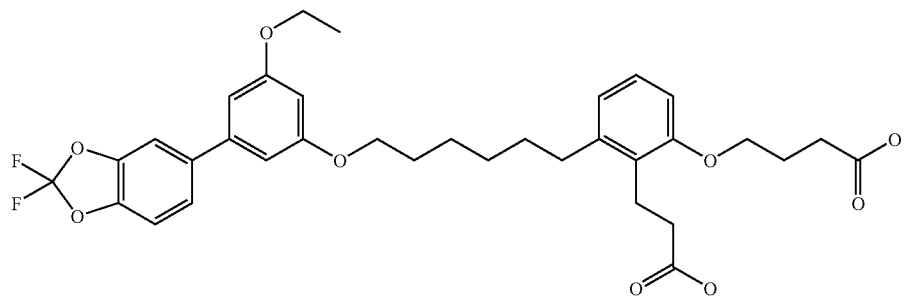

A similar procedure as described in Example 43, step 5 was used, starting from 4-[3-{6-[3-(2,2-difluoro-benzo[1,3]dioxol-5-yl)-5-ethoxy-phenoxy)-hexyl}-2-(2-ethoxycarbonyl-ethyl)-phenoxy]-butyric acid ethyl ester (395 mg, 0.58 mmol) and 1.0 N aqueous sodium hydroxide (5.8 mL) to afford 4-(2-(2-carboxy-ethyl)-3-{6-[3-(2,2-difluoro-benzo[1,3]dioxol-5-yl)-5-ethoxy-phenoxy]-hexyl}-phenoxy)-butyric acid (260 mg, 72%) as a light yellow solid: ES(+)-HRMS m/e calcd for $C_{34}H_{38}F_2O_9$ $(M+Na)^+$ 651.2376. found 651.2381.

Example 58

4-[3-[6-(5-Benzyloxy-biphenyl-3-yloxy)-hexyl]-2-(2-carboxy-ethyl)-phenoxy]-butyric acid

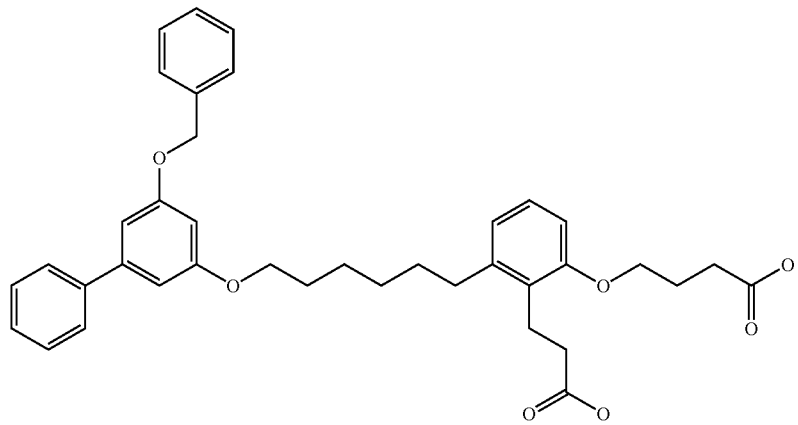

Step 1: 4-[3-[6-(3-Benzyloxy-5-bromo-phenoxy)-hexyl]-2-(2-ethoxycarbonyl-ethyl)-phenoxy]-butyric acid ethyl ester

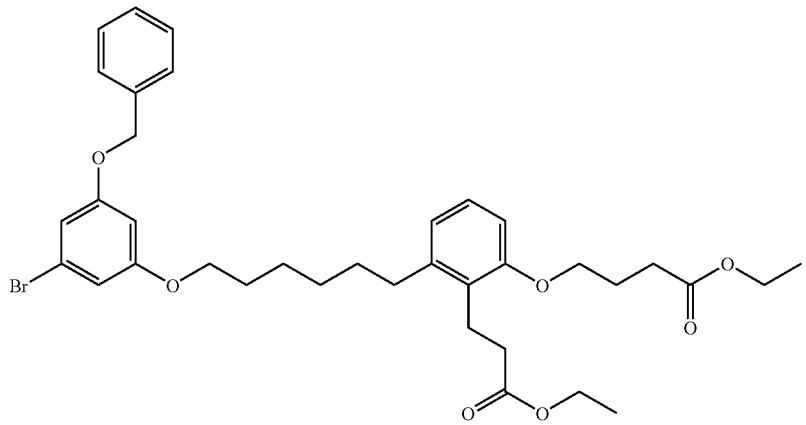

A similar procedure as described in Example 43, step 3 was used, starting from 4-[3-[6-(3-bromo-5-hydroxy-phenoxy)-hexyl]-2-(2-ethoxycarbonyl-ethyl)-phenoxy]-butyric acid ethyl ester (930 mg, 1.6 mmol), benzyl bromide (343 mg, 2.0 mmol), and potassium carbonate (553 mg, 4.0 mmol) to afford 4-[3-[6-(3-benzyloxy-5-bromo-phenoxy)-hexyl]-2-(2-ethoxycarbonyl-ethyl)-phenoxy]-butyric acid ethyl ester (1.06 g, 98%) as a colorless viscous oil: ES(+)-HRMS m/e calcd for $C_{36}H_{45}BrO_7$ (M+Na)$^+$ 691.2241. found 691.2238.

Step 2: 4-[3-[6-(5-Benzyloxy-biphenyl-3-yloxy)-hexyl]-2-(2-ethoxycarbonyl-ethyl)-phenoxy]-butyric acid ethyl ester A similar procedure as described in Example 43, step 4 was used, starting from 4-[3-[6-(3-benzyloxy-5-bromo-phenoxy)-hexyl]-2-(2-ethoxycarbonyl-ethyl)-phenoxy]-butyric acid ethyl ester (260 mg, 0.39 mmol), phenylboronic acid (95 mg, 0.78 mmol), [1,1'-bis(diphenylphosphino)ferrocene]dichloropalladium(II) (73 mg, 0.1 mmol), and cesium carbonate (253 mg, 0.78 mmol) to obtain 4-[3-[6-(5-benzyloxy-biphenyl-3-yloxy)-hexyl]-2-(2-ethoxycarbonyl-ethyl)-phenoxy]-butyric acid ethyl ester (230 mg, 89%) as a colorless viscous oil: ES(+)-HRMS m/e calcd for $C_{42}H_{50}O_7$ (M+Na)$^+$ 689.3449. found 689.3447.

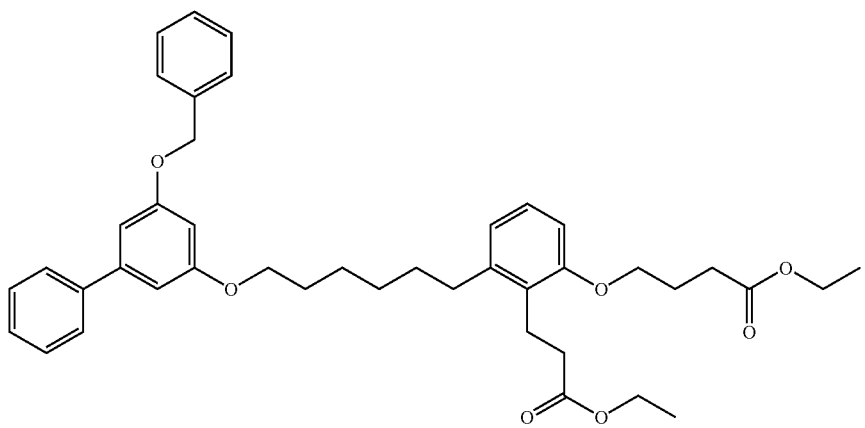

Step 3: 4-[3-[6-(5-Benzyloxy-biphenyl-3-yloxy)-hexyl]-2-(2-carboxy-ethyl)-phenoxy]-butyric acid

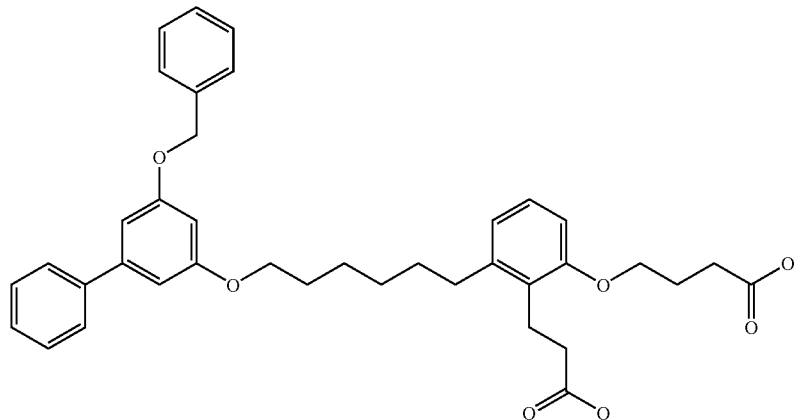

A similar procedure as described in Example 43, step 5 was used, starting from 4-[3-[6-(5-benzyloxy-biphenyl-3-yloxy)-hexyl]-2-(2-ethoxycarbonyl-ethyl)-phenoxy]-butyric acid ethyl ester (224 mg, 0.34 mmol) and 1.0 N aqueous sodium hydroxide (5 mL) to afford 4-[3-[6-(5-benzyloxy-biphenyl-3-yloxy)-hexyl]-2-(2-carboxy-ethyl)-phenoxy]-butyric acid (165 mg, 80%) as an amorphous white solid: ES(+)-HRMS m/e calcd for $C_{38}H_{42}O_7$ (M+Na)$^+$ 633.2823. found 633.2820.

Example 59

4-[3-[6-(5-Benzyloxy-3'-fluoro-biphenyl-3-yloxy)-hexyl]-2-(2-carboxy-ethyl)-phenoxy]-butyric acid

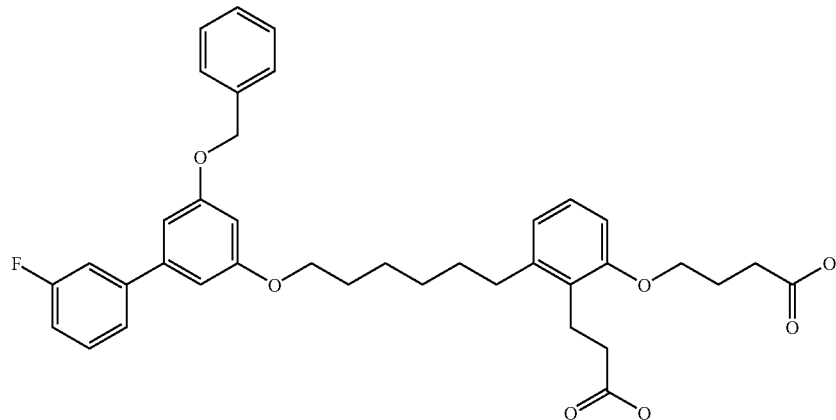

Step 1: 4-[3-[6-(5-Benzyloxy-3'-fluoro-biphenyl-3-yloxy)-hexyl]-2-(2-ethoxycarbonyl-ethyl)-phenoxy]-butyric acid ethyl ester

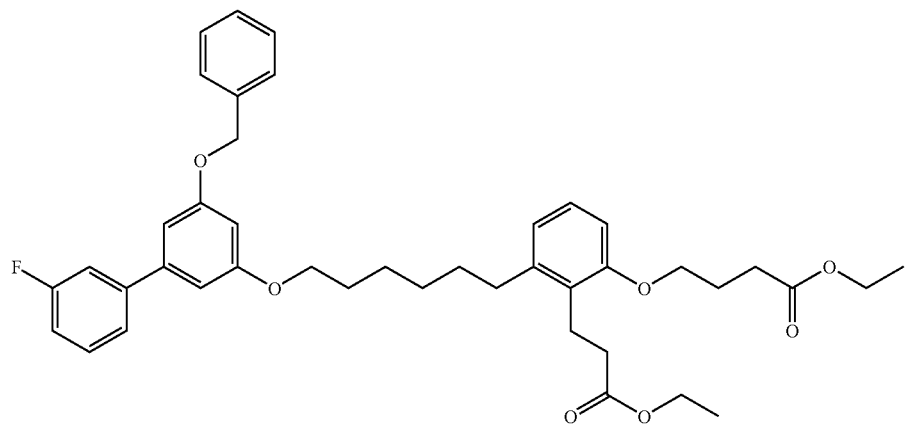

A similar procedure as described in Example 43, step 4 was used, starting from 4-[3-[6-(3-benzyloxy-5-bromo-phenoxy)-hexyl]-2-(2-ethoxycarbonyl-ethyl)-phenoxy]-butyric acid ethyl ester (260 mg, 0.39 mmol), 3-fluoro-phenylboronic acid (109 mg, 0.78 mmol), [1,1'-bis(diphenylphosphino)ferrocene]dichloropalladium(II) (73 mg, 0.1 mmol), and cesium carbonate (253 mg, 0.78 mmol) to obtain 4-[3-[6-(5-benzyloxy-3'-fluoro-biphenyl-3-yloxy)-hexyl]-2-(2-ethoxycarbonyl-ethyl)-phenoxy]-butyric acid ethyl ester (244 mg, 92%) as a colorless viscous oil: ES(+)-HRMS m/e calcd for $C_{42}H_{49}FO_7$ (M+Na)$^+$ 707.3354. found 707.3355.

Step 2: 4-[3-[6-(5-Benzyloxy-3'-fluoro-biphenyl-3-yloxy)-hexyl]-2-(2-carboxy-ethyl)-phenoxy]-butyric acid

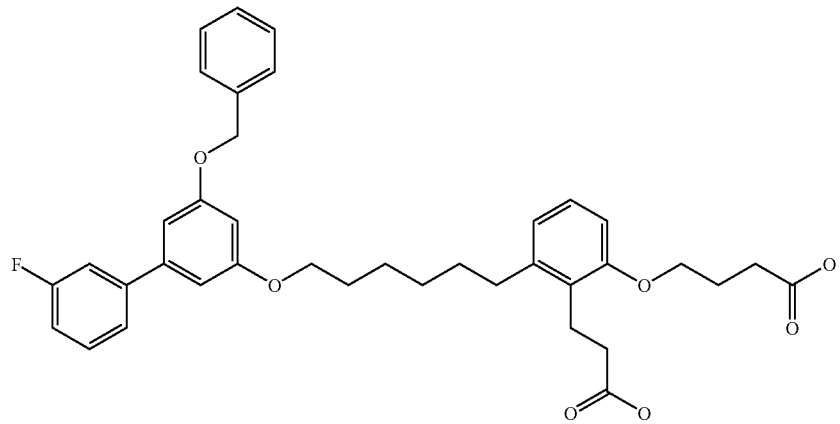

A similar procedure as described in Example 43, step 5 was used, starting from 4-[3-[6-(5-benzyloxy-3'-fluoro-biphenyl-3-yloxy)-hexyl]-2-(2-ethoxycarbonyl-ethyl)-phenoxy]-butyric acid ethyl ester (229 mg, 0.34 mmol) and 1.0 N aqueous sodium hydroxide (5 mL) to afford 4-[3-[6-(5-benzyloxy-3'-fluoro-biphenyl-3-yloxy)-hexyl]-2-(2-carboxy-ethyl)-phenoxy]-butyric acid (163 mg, 78%) as an amorphous white solid: ES(+)-HRMS m/e calcd for $C_{38}H_{41}FO_7$ (M+Na)$^+$ 651.2728. found 651.2729.

Example 60

4-[3-[6-(3-Benzo[1,3]dioxol-5-yl-5-benzyloxy-phenoxy)-hexyl]-2-(2-carboxy-ethyl)-phenoxy]-butyric acid

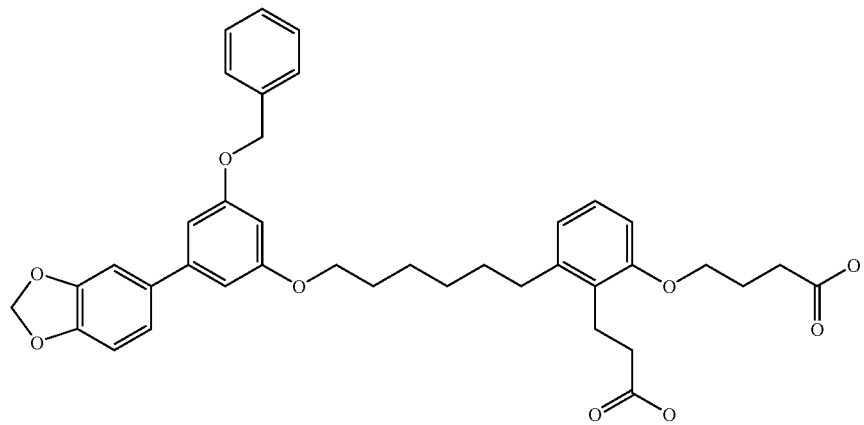

Step 1: 4-[3-[6-(3-Benzo[1,3]dioxol-5-yl-5-benzyloxy-phenoxy)-hexyl]-2-(2-ethoxycarbonyl-ethyl)-phenoxy]-butyric acid ethyl ester

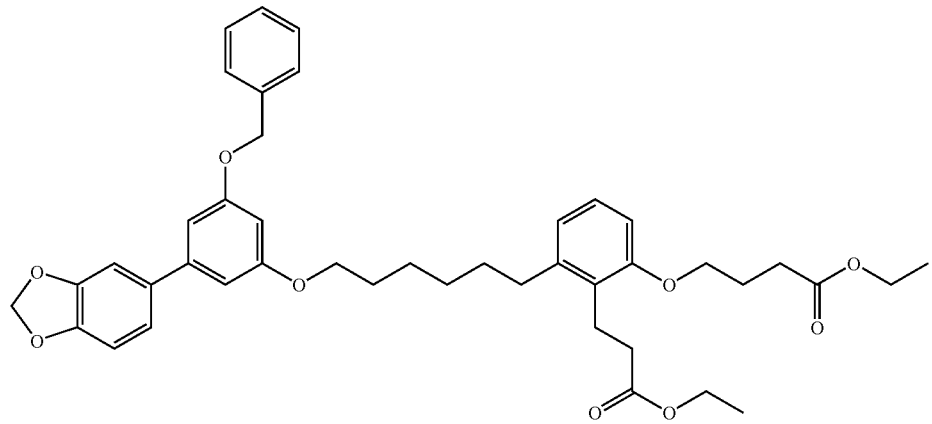

A similar procedure as described in Example 43, step 4 was used, starting from 4-[3-[6-(3-benzyloxy-5-bromo-phenoxy)-hexyl]-2-(2-ethoxycarbonyl-ethyl)-phenoxy]-butyric acid ethyl ester (260 mg, 0.39 mmol), 3,4-methylenedioxyphenylboronic acid (127 mg, 0.78 mmol), [1,1'-bis(diphenylphosphino)ferrocene]dichloropalladium(II) (73 mg, 0.1 mmol), and cesium carbonate (253 mg, 0.78 mmol) to obtain 4-[3-[6-(3-benzo[1,3]dioxol-5-yl-5-benzyloxy-phenoxy)-hexyl]-2-(2-ethoxycarbonyl-ethyl)-phenoxy]-butyric acid ethyl ester (260 mg, 94%) as a colorless viscous oil: ES(+)-HRMS m/e calcd for $C_{43}H_{50}O_9$ (M+Na)$^+$ 733.3347. found 733.3345.

Step 2: 4-[3-[6-(3-Benzo[1,3]dioxol-5-yl-5-benzyloxy-phenoxy)-hexyl]-2-(2-carboxy-ethyl)-phenoxy]-butyric acid A similar procedure as described in Example 43, step 5 was used, starting from 4-[3-[6-(3-benzo[1,3]dioxol-5-yl-5-benzyloxy-phenoxy)-hexyl]-2-(2-ethoxycarbonyl-ethyl)-phenoxy]-butyric acid ethyl ester (254 mg, 0.36 mmol) and 1.0 N aqueous sodium hydroxide (5 mL) to afford 4-[3-[6-(3-benzo[1,3]dioxol-5-yl-5-benzyloxy-phenoxy)-hexyl]-2-(2-carboxy-ethyl)-phenoxy]-butyric acid (107 mg, 46%) as an amorphous off-white solid: ES(+)-HRMS m/e calcd for $C_{39}H_{42}O_9$ (M+Na)$^+$ 677.2721. found 677.2718.

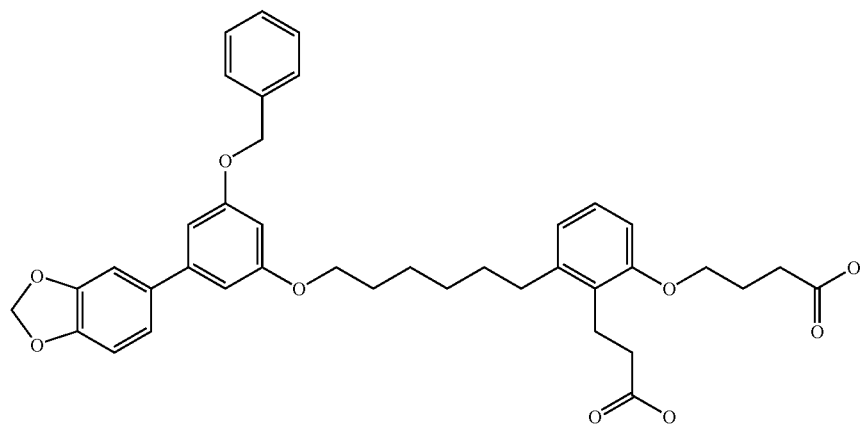

Example 61

4-[3-[6-(3-Benzyloxy-5-thiophen-3-yl-phenoxy)-hexyl]-2-(2-carboxy-ethyl)-phenoxy]-butyric acid

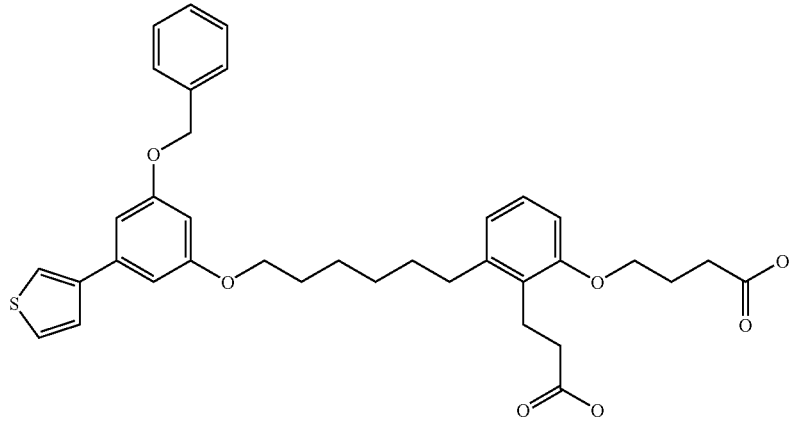

Step 1: 4-[3-[6-(3-Benzyloxy-5-thiophen-3-yl-phenoxy)-hexyl]-2-(2-ethoxycarbonyl-ethyl)-phenoxy]-butyric acid ethyl ester

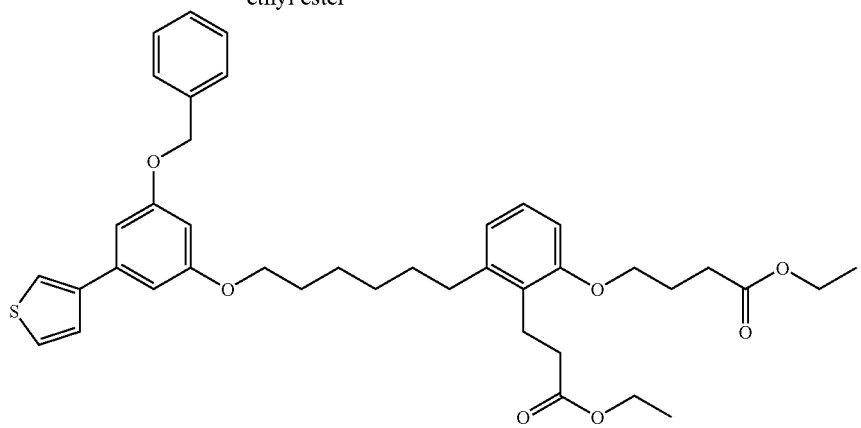

A similar procedure as described in Example 43, step 4 was used, starting from 4-[3-[6-(3-benzyloxy-5-bromo-phenoxy)-hexyl]-2-(2-ethoxycarbonyl-ethyl)-phenoxy]-butyric acid ethyl ester (260 mg, 0.39 mmol), 3-thiophenylboronic acid (99 mg, 0.78 mmol), [1,1'-bis(diphenylphosphino)ferrocene]dichloropalladium(II) (73 mg, 0.1 mmol), and cesium carbonate (253 mg, 0.78 mmol) to obtain 4-[3-[6-(3-benzyloxy-5-thiophen-3-yl-phenoxy)-hexyl]-2-(2-ethoxycarbonyl-ethyl)-phenoxy]-butyric acid ethyl ester (165 mg, 67%) as a colorless viscous oil: ES(+)-HRMS m/e calcd for $C_{40}H_{48}O_7S$ (M+Na)$^+$ 695.3013. found 695.3008.

Step 2: 4-[3-[6-(3-Benzyloxy-5-thiophen-3-yl-phenoxy)-hexyl]-2-(2-carboxy-ethyl)-phenoxy]-butyric acid

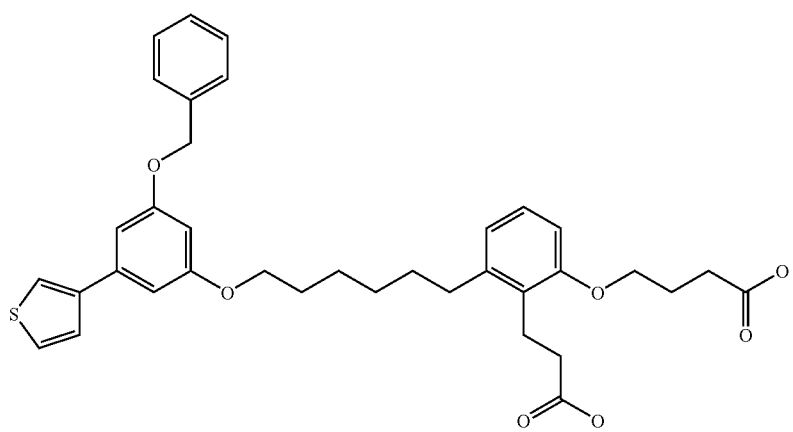

A similar procedure as described in Example 43, step 5 was used, starting from 4-[3-[6-(3-benzyloxy-5-thiophen-3-yl-phenoxy)-hexyl]-2-(2-ethoxycarbonyl-ethyl)-phenoxy]-butyric acid ethyl ester (160 mg, 0.24 mmol) and 1.0 N aqueous sodium hydroxide (5 mL) to afford 4-[3-[6-(3-benzyloxy-5-thiophen-3-yl-phenoxy)-hexyl]-2-(2-carboxy-ethyl)-phenoxy]-butyric acid (129 mg, 88%) as a light brown waxy solid: ES(+)-HRMS m/e calcd for $C_{36}H_{40}O_7S$ $(M+Na)^+$ 639.2387. found 639.2386.

Example 62

4-[2-(2-Carboxy-ethyl)-3-[6-(3-cyclopentylmethoxy-5-thiophen-3-yl-phenoxy)-hexyl]-phenoxy]-butyric acid

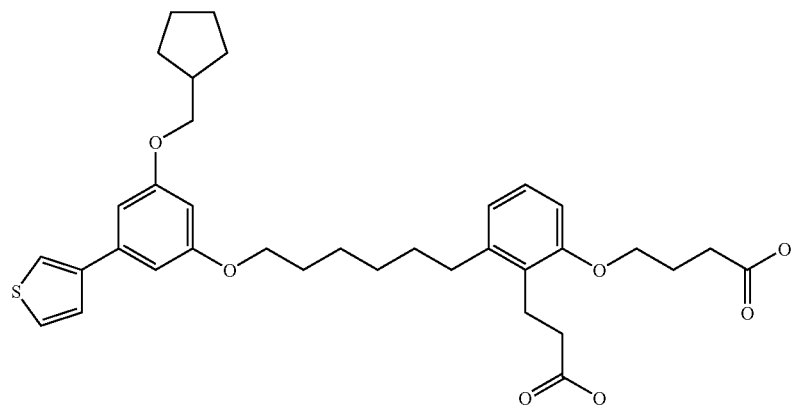

Step 1: 4-[3-[6-(3-Bromo-5-cyclopentyl-methoxy-phenoxy)-hexyl]-2-(2-ethoxycarbonyl-ethyl)-phenoxy]-butyric acid ethyl ester

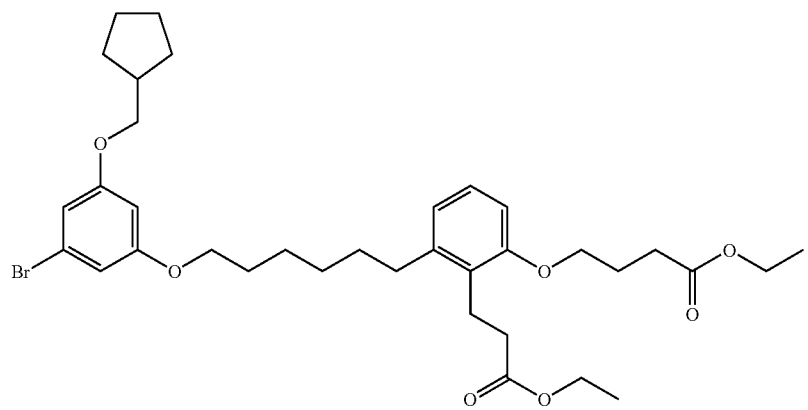

A similar procedure as described in Example 43, step 3 was used, starting from 4-[3-[6-(3-bromo-5-hydroxy-phenoxy)-hexyl]-2-(2-ethoxycarbonyl-ethyl)-phenoxy]-butyric acid ethyl ester (600 mg, 1.03 mmol), iodomethylcyclopentane (260 mg, 1.24 mmol), and potassium carbonate (356 mg, 2.57 mmol) to afford 4-[3-[6-(3-bromo-5-cyclopentylmethoxy-phenoxy)-hexyl]-2-(2-ethoxycarbonyl-ethyl)-phenoxy]-butyric acid ethyl ester (487 g, 73%) as a colorless viscous oil: EI(+)-LRMS m/e calcd for $C_{35}H_{49}BrO_7$ $(M+H)^+$ 663.45. found 663.5.

Step 2: 4-[3-[6-(3-Cyclopentylmethoxy-5-thiophen-3-yl-phenoxy)-hexyl]-2-(2-ethoxycarbonyl-ethyl)-phenoxy]-butyric acid ethyl ester

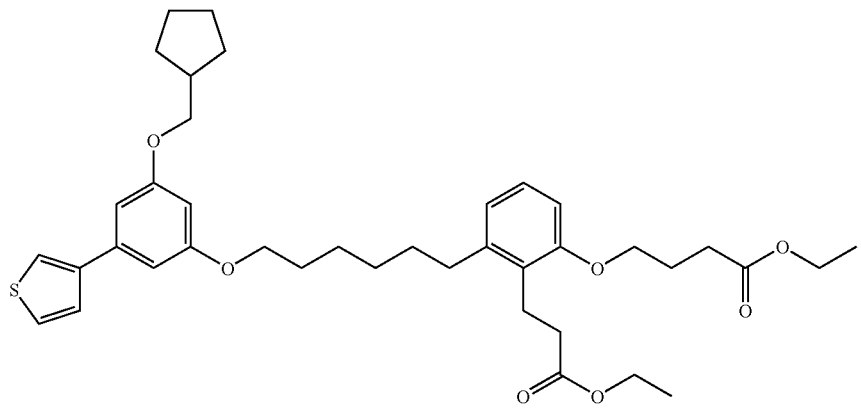

A similar procedure as described in Example 43, step 4 was used, starting from 4-[3-[6-(3-bromo-5-cyclopentyl-methoxy-phenoxy)-hexyl]-2-(2-ethoxycarbonyl-ethyl)-phenoxy]-butyric acid ethyl ester (136 mg, 0.2 mmol), 3-thiophenylboronic acid (53 mg, 0.41 mmol), [1,1'-bis(diphenylphosphino)ferrocene]dichloropalladium(II) (73 mg, 0.1 mmol), and cesium carbonate (134 mg, 0.41 mmol) to obtain 4-[3-[6-(3-cyclopentylmethoxy-5-thiophen-3-yl-phenoxy)-hexyl]-2-(2-ethoxycarbonyl-ethyl)-phenoxy]-butyric acid ethyl ester (129 mg, 95%) as a colorless viscous oil: ES(+)-HRMS m/e calcd for $C_{39}H_{52}O_7S$ (M+Na)$^+$ 687.3326. found 687.3328.

Step 3: 4-[2-(2-Carboxy-ethyl)-3-[6-(3-cyclopentyl-methoxy-5-thiophen-3-yl-phenoxy)-hexyl]-phenoxy]-butyric acid

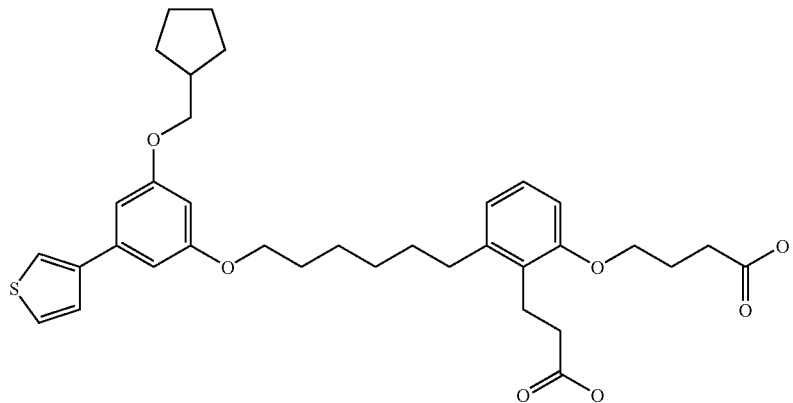

A similar procedure as described in Example 43, step 5 was used, starting from 4-[3-[6-(3-cyclopentylmethoxy-5-thiophen-3-yl-phenoxy)-hexyl]-2-(2-ethoxycarbonyl-ethyl)-phenoxy]-butyric acid ethyl ester (117 mg, 0.17 mmol) and 1.0 N aqueous sodium hydroxide (5 mL) to afford 4-[2-(2-carboxy-ethyl)-3-[6-(3-cyclopentylmethoxy-5-thiophen-3-yl-phenoxy)-hexyl]-phenoxy]-butyric acid (104 mg, 98%) as a off-white waxy solid: ES(+)-HRMS m/e calcd for $C_{35}H_{44}O_7S$ (M+H)$^+$ 609.2881. found 609.2881.

Example 63

4-[2-(2-Carboxy-ethyl)-3-[6-(5-cyclopentylmethoxy-3'-fluoro-biphenyl-3-yloxy)-hexyl]-phenoxy]-butyric acid A similar procedure as described in Example 43, step 4 was used, starting from 4-[3-[6-(3-bromo-5-cyclopentylmethoxy-phenoxy)-hexyl]-2-(2-ethoxycarbonyl-ethyl)-phenoxy]-butyric acid ethyl ester (152 mg, 0.23 mmol), 3-fluorophenylboronic acid (65 mg, 0.46 mmol), [1,1'-bis(diphenylphosphino)ferrocene]dichloropalladium(II) (73 mg, 0.1 mmol), and cesium carbonate (150 mg, 0.46 mmol) to obtain 4-[3-[6-(5-cyclopentylmethoxy-3'-fluoro-biphenyl-3-yloxy)-hexyl]-2-(2-ethoxycarbonyl-ethyl)-phenoxy]-butyric acid ethyl ester (114 mg, 74%) as a colorless viscous oil: ES(+)-HRMS m/e calcd for $C_{41}H_{53}FO_7$ (M+H)$^+$ 677.3848. found 677.3850.

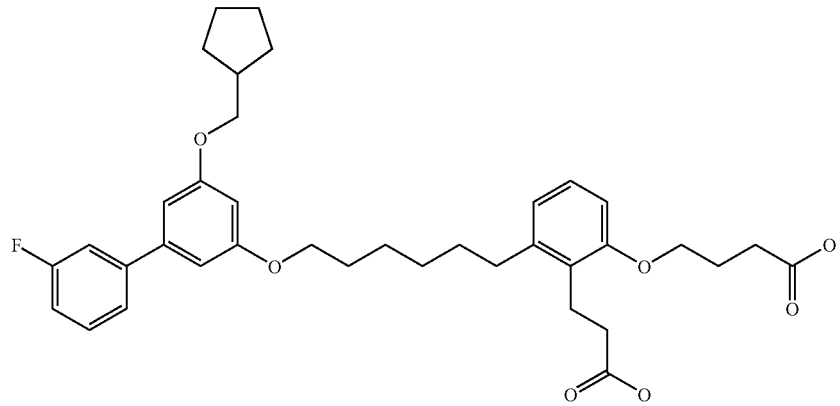

Step 1: 4-[3-[6-(5-Cyclopentylmethoxy-3'-fluoro-biphenyl-3-yloxy)-hexyl]-2-(2-ethoxycarbonyl-ethyl)-phenoxy]-butyric acid ethyl ester

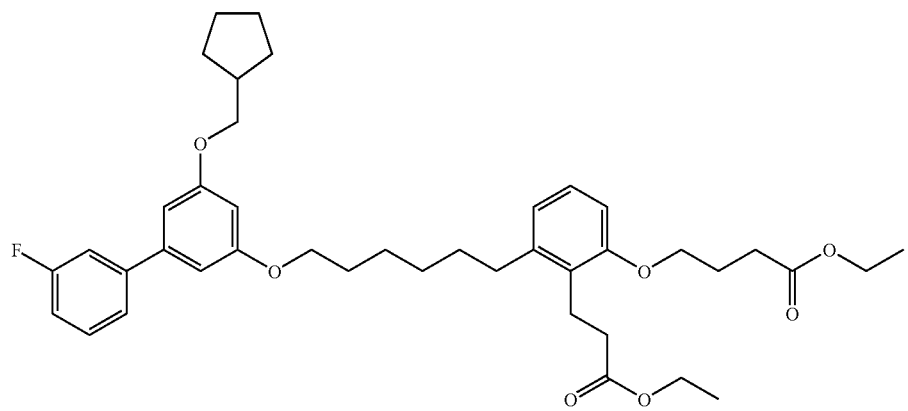

Step 2: 4-[2-(2-Carboxy-ethyl)-3-[6-(5-cyclopentylmethoxy-3'-fluoro-biphenyl-3-yloxy)-hexyl]phenoxy]-butyric acid

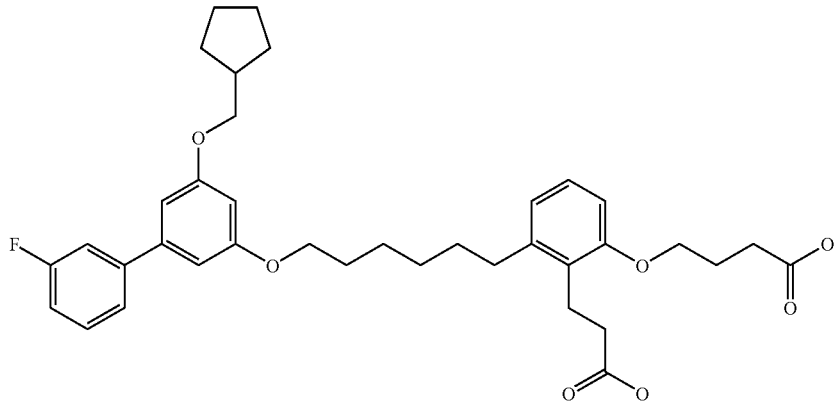

A similar procedure as described in Example 43, step 5 was used, starting from 4-[3-[6-(5-cyclopentylmethoxy-3'-fluoro-biphenyl-3-yloxy)-hexyl]-2-(2-ethoxycarbonyl-ethyl)-phenoxy]-butyric acid ethyl ester (104 mg, 0.15 mmol) and 1.0 N aqueous sodium hydroxide (5 mL) to afford 4-[2-(2-carboxy-ethyl)-3-[6-(5-cyclopentylmethoxy-3'-fluoro-biphenyl-3-yloxy)-hexyl]-phenoxy]-butyric acid (92 mg, 97%) as a off-white waxy solid: ES(+)-HRMS m/e calcd for $C_{37}H_{45}FO_7$ $(M+H)^+$ 621.3222. found 621.3222.

Method E

Example 64

4-[3-[6-(3-Acetyl-5-benzo[1,3]dioxol-5-yl-phenoxy)-hexyl]-2-(2-carboxy-ethyl)-phenoxy]-butyric acid

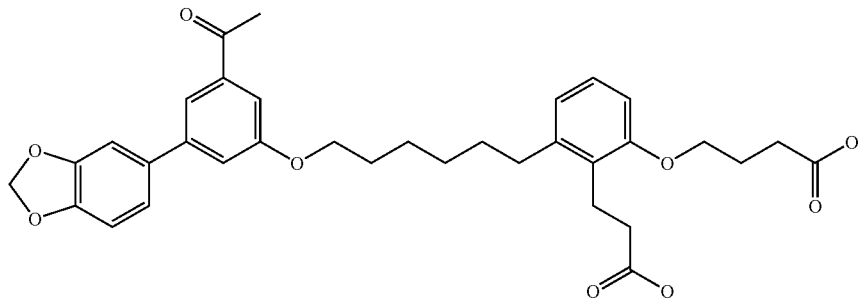

Step 1: 1-(3-Bromo-5-iodo-phenyl)-ethanone

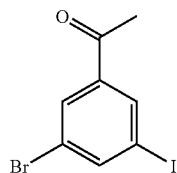

To a solution of 3-bromo-5-iodobenzoic acid (4.9 g, 15.0 mmol) in dichloromethane (50 mL) were added dimethylformamide (250 uL) and oxalyl chloride (2.54 mL, 30 mmol) at 0° C. Then, the reaction mixture was warmed to room temperature in 1 h and was stirred for 15 h. Then, the solvent was removed under vacuum and dried under high vacuum to obtain the corresponding benzoyl chloride. In another 3-necked RB flask, lithium chloride (1.69 g, 40 mmol, pre-dried at 130° C. under high vacuum for 2 h) and copper cyanide (1.79 g, 20 mmol) was charged and tetrahydrofuran (40 mL) was added at room temperature and it was stirred for 10 min to obtain a clear solution. Then, the reaction mixture was cooled to −70° C. and slowly treated with a 3M solution of methylmagnesium chloride in tetrahydrofuran (6.66 mL, 20 mmol). After addition, the reaction mixture was allowed to warm to −30° C. where it was stirred for 5 min. The resulting clear reaction mixture was again cooled back to −70° C. and then slowly treated with a solution of the above prepared substituted benzoyl chloride (15 mmol) in tetrahydrofuran (40 mL). After addition, the reaction mixture was allowed to warm to −20° C. and stirred for 15 h. The reaction mixture was then poured into a solution consisting of a saturated aqueous ammonium chloride solution (100 mL) and ammonium hydroxide (20 mL) and the organic compound was extracted into ethyl acetate (2×100 mL) and the combined ethyl acetate extracts were washed with brine solution (300 mL). Then, the organic layer was dried over anhydrous magnesium sulfate, filtered, and concentrated in vacuo. The crude residue was purified by using an ISCO 120 g column, eluting with 0-20% ethyl acetate in hexanes to obtain 1-(3-bromo-5-iodo-phenyl)-ethanone (3.15 g, 65%) as a white solid: ES(+)-HRMS m/e calcd for $C_8H_6BrIO$ $(M+)^+$ 323.8646. found 323.8642.

Step 2: 1-(3-Bromo-5-hydroxy-phenyl)-ethanone

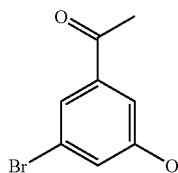

To a mixture of 1-(3-bromo-5-iodo-phenyl)-ethanone (2.28 g, 7.0 mmol), sodium hydroxide (1.4 g, 35.1 mmol), and $Cu_2O$ (143 mg, 1.0 mmol) were added pyridine (20 mL) and water (40 mL) at room temperature. The resulting suspension was heated to 110° C. and stirred for 24 h. Then the reaction mixture was cooled to room temperature and diluted with 1N hydrochloric acid (200 mL). Then, the organic compound was extracted into ethyl acetate (3×100 mL) and the combined organic extracts were washed with 1N hydrochloric acid (200 mL) and brine solution (200 mL). The organic layers were dried over anhydrous magnesium sulfate and filtration of the drying agent and concentration of the solvent under vacuum gave the crude dark brown solid which was tried to dissolve in acetonitrile (50 mL) at reflux, but it did not dissolve completely. Then, it was diluted with ethyl acetate (~10 mL) and hexanes (~15 mL). The dark suspension was stored in the refrigerator. Only few solids were formed and they were coolected by filtration and washed with acetonitrile. Then, the mother liquor was removed under vacuum and the dark brown solids were now dissolved in acetonitrile (50 mL) at reflux and it was treated with charcoal to remove some color. It was then filtered and the solvent was removed under vacuum to afford reasonably pure 1-(3-bromo-5-hydroxy-phenyl)-ethanone (965 mg, 64%) as a brown solid: ES(–)-HRMS m/e calcd for $C_8H_7BrO_2$ (M–H)⁻ 212.9556. found 212.9556.

Step 3: 4-[3-[6-(3-Acetyl-5-bromo-phenoxy)-hexyl]-2-(2-ethoxycarbonyl-ethyl)-phenoxy]-butyric acid ethyl ester

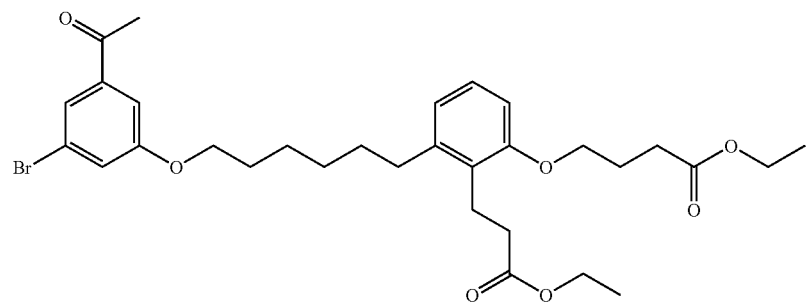

A similar procedure as described in Example 43, step 3 was used, starting from 4-[3-[6-bromo-hexyl]-2-(2-ethoxycarbonyl-ethyl)-phenoxy]-butyric acid ethyl ester (2.36 g, 5.0 mmol), 1-(3-bromo-5-hydroxy-phenyl)-ethanone (965 mg, 4.48 mmol), and potassium carbonate (1.38 g, 10 mmol) to afford 4-[3-[6-(3-acetyl-5-bromo-phenoxy)-hexyl]-2-(2-ethoxycarbonyl-ethyl)-phenoxy]-butyric acid ethyl ester (2.15 g, 79%) as a colorless viscous oil: EI(+)-HRMS m/e calcd for $C_{31}H_{41}BrO_7$ (M+Na)⁺ 627.1928. found 627.1925.

Step 4: 4-[3-[6-(3-Acetyl-5-benzo[1,3]-dioxol-5-yl-phenoxy)-hexyl]-2-(2-ethoxycarbonyl-ethyl)-phenoxy]-butyric acid ethyl ester

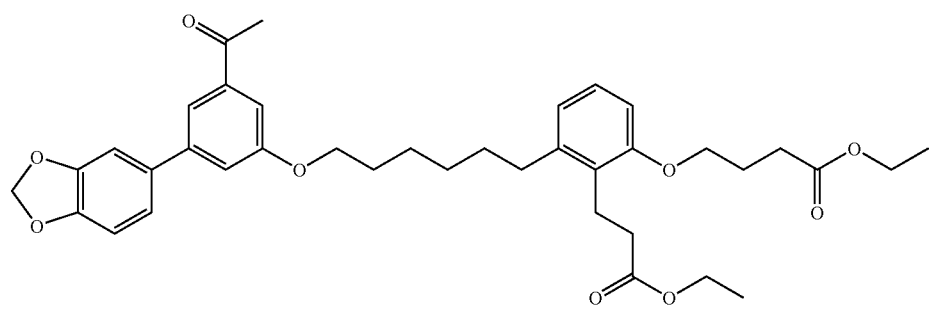

A similar procedure as described in Example 43, step 4 was used, starting from 4-[3-[6-(3-acetyl-5-bromo-phenoxy)-hexyl]-2-(2-ethoxycarbonyl-ethyl)-phenoxy]-butyric acid ethyl ester (303 mg, 0.5 mmol), 3,4-methylenedioxyphenylboronic acid (166 mg, 1.0 mmol), [1,1'-bis(diphenylphosphino)ferrocene]dichloropalladium(II) (73 mg, 0.1 mmol), and cesium carbonate (326 mg, 1.0 mmol) to obtain 4-[3-[6-(3-acetyl-5-benzo[1,3]-dioxol-5-yl-phenoxy)-hexyl]-2-(2-ethoxycarbonyl-ethyl)-phenoxy]-butyric acid ethyl ester (235 mg, 73%) as a colorless oil: ES(+)-HRMS m/e calcd for $C_{38}H_{46}O_9$ (M+Na)$^+$ 669.3034. found 669.3031.

Step 5: 4-[3-[6-(3-Acetyl-5-benzo[1,3]dioxol-5-yl-phenoxy)-hexyl]-2-(2-carboxy-ethyl)-phenoxy]-butyric acid

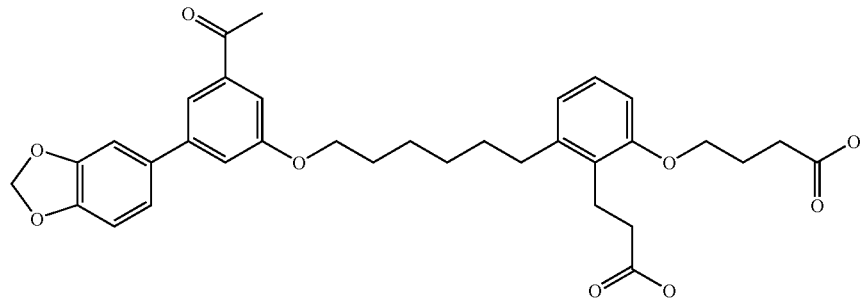

A similar procedure as described in Example 43, step 5 was used, starting from 4-[3-[6-(3-acetyl-5-benzo[1,3]-dioxol-5-yl-phenoxy)-hexyl]-2-(2-ethoxycarbonyl-ethyl)-phenoxy]-butyric acid ethyl ester (230 mg, 0.36 mmol) and 1.0 N aqueous sodium hydroxide (8 mL) to afford 4-[3-[6-(3-acetyl-5-benzo[1,3]dioxol-5-yl-phenoxy)-hexyl]-2-(2-carboxy-ethyl)-phenoxy]-butyric acid (192 mg, 92%) as a white solid: ES(+)-HRMS m/e calcd for $C_{34}H_{38}O_9$ (M+Na)$^+$ 613.2408. found 613.2407.

Example 65

4-[3-[6-(3-Acetyl-5-(2,3-dihydro-benzo[1,4]dioxin-6-yl-phenoxy)-hexyl]-2-(2-carboxy-ethyl)-phenoxy]-butyric acid

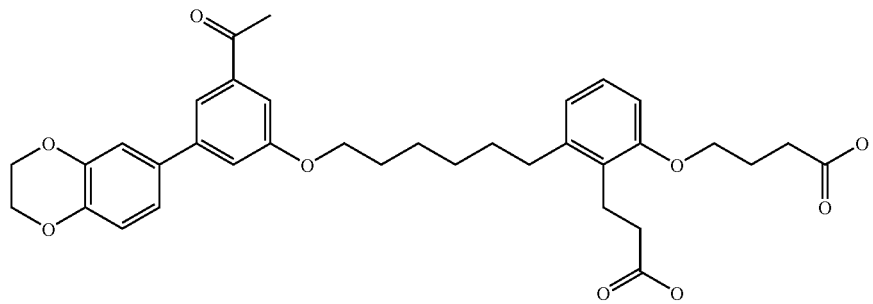

Step 1: 4-[3-[6-(3-Acetyl-5-(2,3-dihydro-benzo[1,4]-dioxin-6-yl-phenoxy)-hexyl]-2-(2-ethoxycarbonyl-ethyl)-phenoxy]-butyric acid ethyl ester

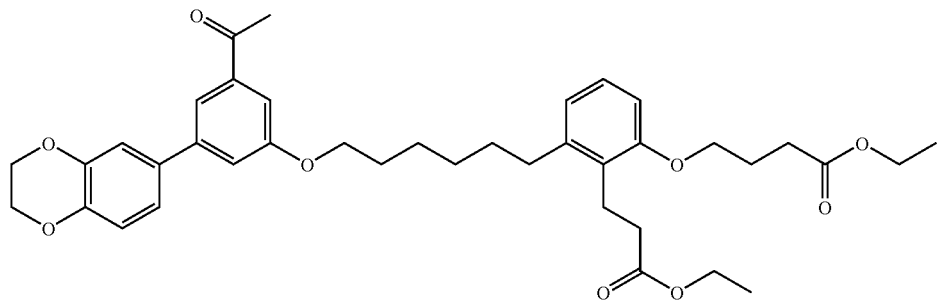

A similar procedure as described in Example 43, step 4 was used, starting from 4-[3-[6-(3-acetyl-5-bromo-phenoxy)-hexyl]-2-(2-ethoxycarbonyl-ethyl)-phenoxy]-butyric acid ethyl ester (303 mg, 0.5 mmol), 1,4-benzodioxane-6-boronic acid (180 mg, 1.0 mmol), [1,1'-bis(diphenylphosphino)ferrocene]dichloropalladium(II) (73 mg, 0.1 mmol), and cesium carbonate (326 mg, 1.0 mmol) to obtain 4-[3-[6-(3-acetyl-5-(2,3-dihydro-benzo[1,4]-dioxin-6-yl-phenoxy)-hexyl]-2-(2-ethoxycarbonyl-ethyl)-phenoxy]-butyric acid ethyl ester (330 mg, 99%) as a colorless oil: ES(+)-HRMS m/e calcd for $C_{39}H_{48}O_9$ (M+Na)$^+$ 683.3190. found 683.3194.

Step 2: 4-[3-[6-(3-Acetyl-5-(2,3-dihydro-benzo[1,4]dioxin-6-yl-phenoxy)-hexyl]-2-(2-carboxy-ethyl)-phenoxy]-butyric acid

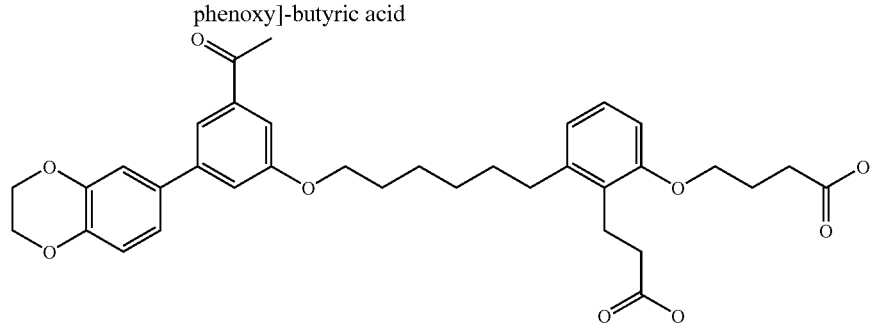

A similar procedure as described in Example 43, step 5 was used, starting from 4-[3-[6-(3-acetyl-5-(2,3-dihydro-benzo[1,4]-dioxin-6-yl-phenoxy)-hexyl]-2-(2-ethoxycarbonyl-ethyl)-phenoxy]-butyric acid ethyl ester (330 mg, 0.5 mmol) and 1.0 N aqueous sodium hydroxide (10 mL) to afford 4-[3-[6-(3-acetyl-5-(2,3-dihydro-benzo[1,4]dioxin-6-yl-phenoxy)-hexyl]-2-(2-carboxy-ethyl)-phenoxy]-butyric acid (200 mg, 61%) as a off-white solid: ES(+)-HRMS m/e calcd for $C_{35}H_{40}O_9$ (M+Na)$^+$ 627.2564. found 627.2560.

Example 66

4-[3-[6-(5-Acetyl-biphenyl-3-yloxy)-hexyl]-2-(2-carboxy-ethyl)-phenoxy]-butyric acid

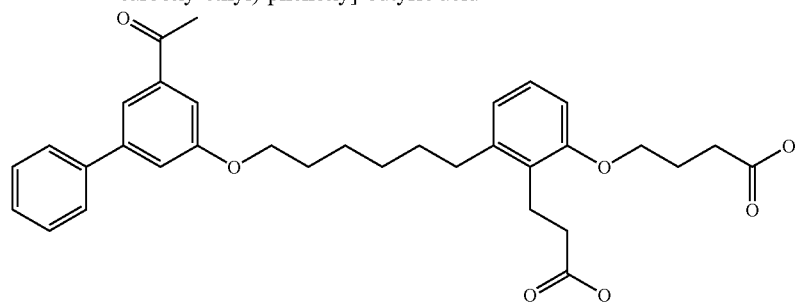

Step 1: 4-[3-[6-(5-Acetyl-biphenyl-3-yloxy)-hexyl]-2-(2-ethoxycarbonyl-ethyl)-phenoxy]-butyric acid ethyl ester

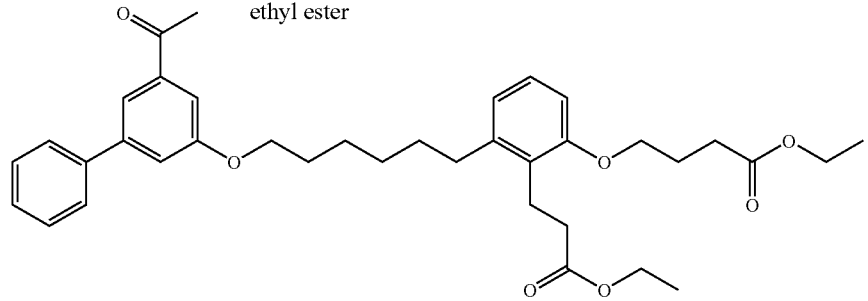

A similar procedure as described in Example 43, step 4 was used, starting from 4-[3-[6-(3-acetyl-5-bromo-phenoxy)-hexyl]-2-(2-ethoxycarbonyl-ethyl)-phenoxy]-butyric acid ethyl ester (303 mg, 0.5 mmol), phenylboronic acid (122 mg, 1.0 mmol), [1,1'-bis(diphenylphosphino)ferrocene]dichloropalladium(II) (73 mg, 0.1 mmol), and cesium carbonate (326 mg, 1.0 mmol) to obtain 4-[3-[6-(5-acetyl-biphenyl-3-yloxy)-hexyl]-2-(2-ethoxycarbonyl-ethyl)-phenoxy]-butyric acid ethyl ester (288 mg, 96%) as a colorless oil: ES(+)-HRMS m/e calcd for $C_{37}H_{46}O_7$ $(M+Na)^+$ 625.3136. found 625.3133.

Step 2: 4-[3-[6-(5-Acetyl-biphenyl-3-yloxy)-hexyl]-2-(2-carboxy-ethyl)-phenoxy]-butyric acid

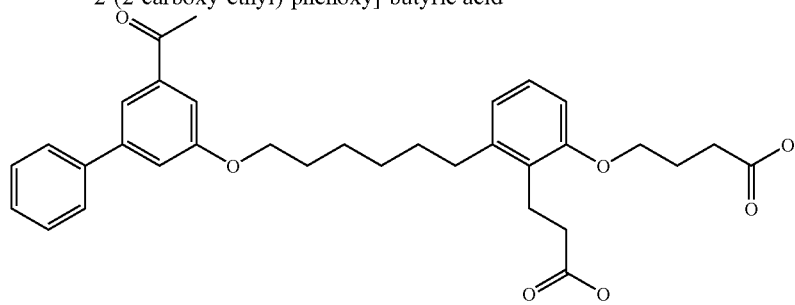

A similar procedure as described in Example 4, step 5 was used, starting from 4-[3-[6-(5-acetyl-biphenyl-3-yloxy)-hexyl]-2-(2-ethoxycarbonyl-ethyl)-phenoxy]-butyric acid ethyl ester (282 mg, 0.47 mmol) and 1.0 N aqueous sodium hydroxide (10 mL) to afford 4-[3-[6-(5-acetyl-biphenyl-3-yloxy)-hexyl]-2-(2-carboxy-ethyl)-phenoxy]-butyric acid (168 mg, 66%) as a white solid: ES(+)-HRMS m/e calcd for $C_{33}H_{38}O_7$ $(M+Na)^+$ 569.2510. found 569.2508.

Example 67

4-[3-[6-(5-Acetyl-3'-fluoro-biphenyl-3-yloxy)-hexyl]-2-(2-carboxy-ethyl)-phenoxy]-butyric acid

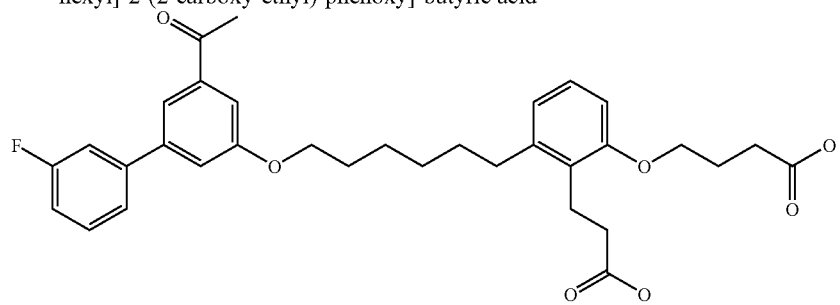

Step 1: 4-[3-[6-(5-Acetyl-3'-fluoro-biphenyl-3-yloxy)-hexyl]-2-(2-ethoxycarbonyl-ethyl)-phenoxy]-butyric acid ethyl ester

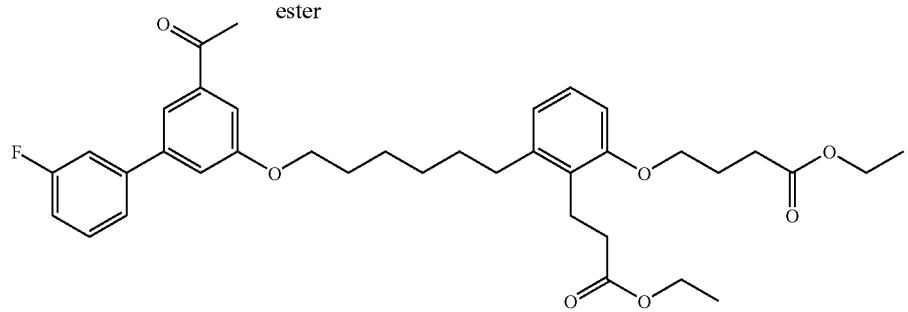

A similar procedure as described in Example 43, step 4 was used, starting from 4-[3-[6-(3-acetyl-5-bromo-phenoxy)-hexyl]-2-(2-ethoxycarbonyl-ethyl)-phenoxy]-butyric acid ethyl ester (303 mg, 0.5 mmol), 3-fluoro-phenylboronic acid (140 mg, 1.0 mmol), [1,1'-bis(diphenylphosphino)ferrocene] dichloropalladium(II) (73 mg, 0.1 mmol), and cesium carbonate (326 mg, 1.0 mmol) to obtain 4-[3-[6-(5-acetyl-3'-fluoro-biphenyl-3-yloxy)-hexyl]-2-(2-ethoxycarbonyl-ethyl)-phenoxy]-butyric acid ethyl ester (288 mg, 93%) as a colorless oil: ES(+)-HRMS m/e calcd for $C_{37}H_{45}FO_7$ (M+Na)$^+$ 643.3041. found 643.3039.

Step 2: 4-[3-[6-(5-Acetyl-3'-fluoro-biphenyl-3-yloxy)-hexyl]-2-(2-carboxy-ethyl)-phenoxy]-butyric acid

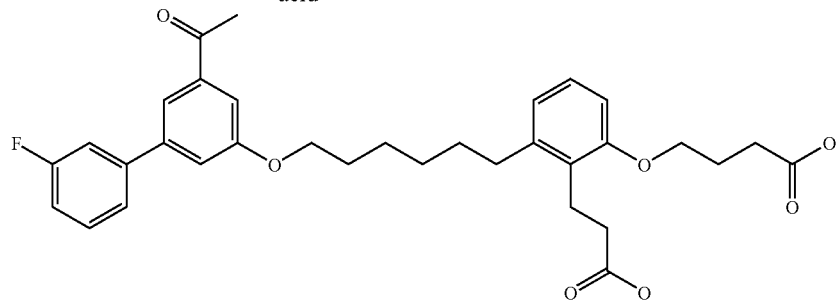

A similar procedure as described in Example 43, step 5 was used, starting from 4-[3-[6-(5-acetyl-3'-fluoro-biphenyl-3-yloxy)-hexyl]-2-(2-ethoxycarbonyl-ethyl)-phenoxy]-butyric acid ethyl ester (275 mg, 0.44 mmol) and 1.0 N aqueous sodium hydroxide (10 mL) to afford 4-[3-[6-(5-acetyl-3'-fluoro-biphenyl-3-yloxy)-hexyl]-2-(2-carboxy-ethyl)-phenoxy]-butyric acid (165 mg, 66%) as a white solid: ES(+)-HRMS m/e calcd for $C_{33}H_{37}FO_7$ (M+Na)$^+$ 587.2415. found 587.2415.

Example 68

4-[3-[6-(3-Acetyl-5-thiophen-3-yl-phenoxy)-hexyl]-2-(2-carboxy-ethyl)-phenoxy]-butyric acid

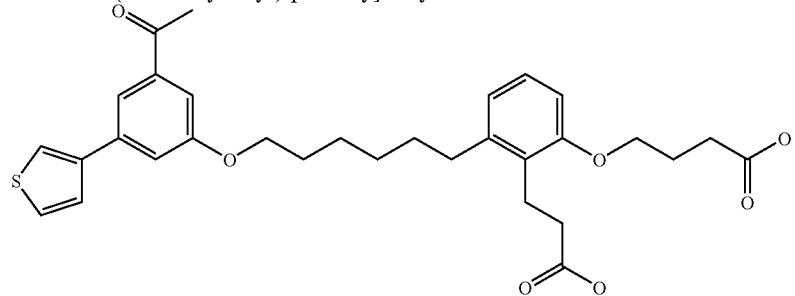

Step 1: 4-[3-[6-(3-Acetyl-5-thiophen-3-yl-phenoxy)-hexyl]-2-(2-ethoxycarbonyl-4ethyl)-phenoxy]-butyric acid ethyl ester

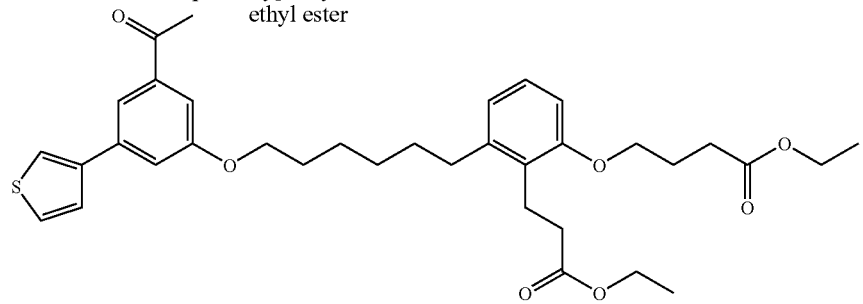

A similar procedure as described in Example 43, step 4 was used, starting from 4-[3-[6-(3-acetyl-5-bromo-phenoxy)-hexyl]-2-(2-ethoxycarbonyl-ethyl)-phenoxy]-butyric acid ethyl ester (303 mg, 0.5 mmol), 3-thiopheneboronic acid (128 mg, 1.0 mmol), [1,1'-bis(diphenylphosphino)ferrocene] dichloropalladium(II) (73 mg, 0.1 mmol), and cesium carbonate (326 mg, 1.0 mmol) to obtain 4-[3-[6-(3-acetyl-5-thiophen-3-yl-phenoxy)-hexyl]-2-(2-ethoxycarbonyl-ethyl)-phenoxy]-butyric acid ethyl ester (285 mg, 94%) as a light brown oil: ES(+)-HRMS m/e calcd for $C_{35}H_{44}O_7S$ (M+Na)$^+$ 631.2700. found 631.2704.

Step 2: 4-[3-[6-(3-Acetyl-5-thiophen-3-yl-phenoxy)-hexyl]-2-(2-carboxy-ethyl)-phenoxy]-butyric acid

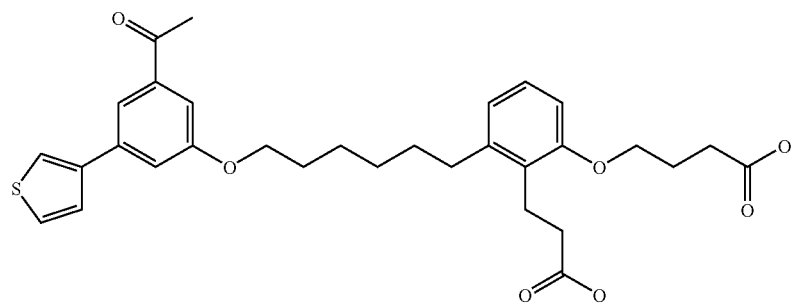

A similar procedure as described in Example 43, step 5 was used, starting from 4-[3-[6-(3-acetyl-5-thiophen-3-yl-phenoxy)-hexyl]-2-(2-ethoxycarbonyl-ethyl)-phenoxy]-butyric acid ethyl ester (272 mg, 0.44 mmol) and 1.0 N aqueous sodium hydroxide (10 mL) to afford 4-[3-[6-(3-acetyl-5-thiophen-3-yl-phenoxy)-hexyl]-2-(2-carboxy-ethyl)-phenoxy]-butyric acid (163 mg, 66%) as a light brown solid: ES(+)-HRMS m/e calcd for $C_{31}H_{36}O_7S$ (M+Na)$^+$ 575.2074. found 575.2074.

Example 69

4-[3-{6-[3-Acetyl-5-(2,2-difluoro-benzo[1,3]dioxol-5-yl)-phenoxy]-hexyl}-2-(2-carboxy-ethyl)-phenoxy]-butyric acid

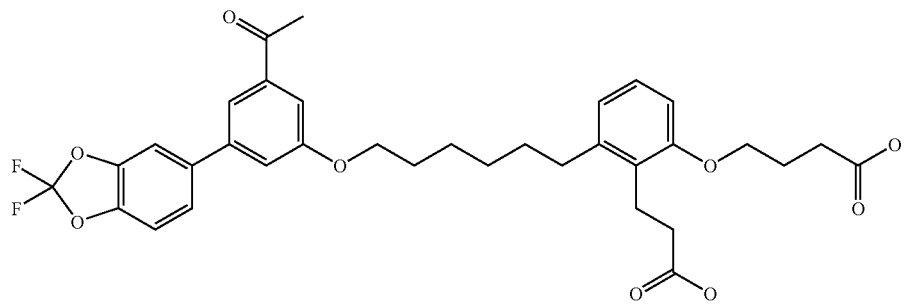

Step 1: Trifluoro-methanesulfonic acid 3-acetyl-5-trifluoromethanesulfonyloxy-phenyl ester

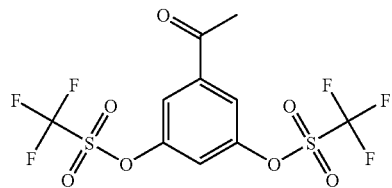

3,5-Dihydroxyacetophenone (5.0 g) was suspended in 100 mL of dichloromethane and then pyridine (10.6 mL) was added. The resulting clear solution was cooled to 0° C. and 11.6 mL of triflic anhydride were added dropwise. After addition was completed, the cooling bath was removed and the reaction mixture was stirred at room temperature for 1 h and then quenched with 1 N hydrochloric acid. The organic solution was separated and washed with saturated sodium bicarbonate solution and brine and dried over anhydrous sodium sulfate. The solvent was removed under reduced pressure and the title compound was obtained by trituration with diethyl ether as white solid (9.9 g, 72% yield). HRMS calcd for $C_{10}H_6O_7S_2F_6$ M$^+$ 415.9459, observed 415.9459

Step 2: Trifluoro-methanesulfonic acid 3-acetyl-5-hydroxy-phenyl ester

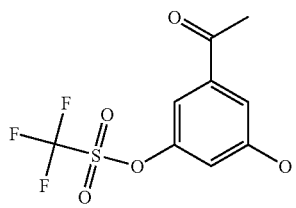

Trifluoro-methanesulfonic acid 3-acetyl-5-trifluoromethanesulfonyloxy-phenyl ester (9.9 g) was dissolved in 1,2-dimethoxyethane (80 mL), followed by addition of cesium carbonate (11.6 g). The resulting suspension was stirred at 80° C. for 3 h and then quenched with saturated solution of ammonium chloride. The solution was then extracted with diethyl ether and combined etherate extracts were washed with brine, dried over anhydrous sodium sulfate, and filtered through a silica pad. The filtrate was concentrated under reduced pressure and purified on a silica gel column using ethyl acetate and hexanes to afford 3.5 g of the title compound (52% yield). HRMS calcd for $C_{19}H_7O_5S_1F_3$ [M+H]$^+$ 285.0039, observed 285.0039.

Step 3: 4-[3-[6-(3-Acetyl-5-trifluoromethane-sulfonyloxy-phenoxy)-hexyl]-2-(2-ethoxy-carbonyl-ethyl)-phenoxy]-butyric acid ethyl ester To a solution of trifluoro-methanesulfonic acid 3-acetyl-5-hydroxy-phenyl ester (1.0 g) in a mixture of acetone and DMF (2:1, 80 mL) were added potassium carbonate (2.4 g) and 4-[3-(6-bromo-hexyl)-2-(2-ethoxycarbonyl-ethyl)-phenoxy]-butyric acid ethyl ester (1.8 g). The resulting mixture was stirred at 75° C. for 3 h. Then the insoluble material was filtered out and the filtrate was diluted with ethyl acetate and washed with water and brine. The organic extract was dried over anhydrous sodium sulfate, concentrated and purified on a silica gel column using ethyl acetate and hexanes to yield 1.7 g of the title compound (72% yield). HRMS calcd for $C_{32}H_{41}O_{10}S_1F_3$ [M+H]$^+$ 675.2446, observed 675.2440.

Step 4: 4-[3-{6-[3-Acetyl-5-(2,2-difluoro-benzo[1,3]dioxol-5-yl)-phenoxy]hexyl}-2-(2-ethoxycarbonyl-ethyl)-phenoxy]-butyric acid ethyl ester

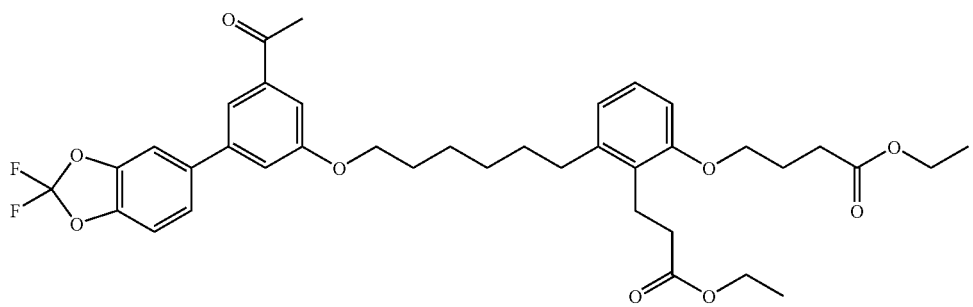

To a solution of 4-[3-[6-(3-acetyl-5-trifluoromethane-sulfonyloxy-phenoxy)-hexyl]-2-(2-ethoxycarbonyl-ethyl)-phenoxy]-butyric acid ethyl ester (500 mg) in 1,2-dimethoxyethane (5 mL) were added 2,2-difluoro-benzo[1,3]dioxole-5-boronic acid (273 mg), 2 M aq. sodium carbonate solution (1.0 mL) and Pd(PPh$_3$)$_4$ (8 mg) and the resulting mixture was stirred at 90° C. for 3 h. Then the reaction mixture was diluted with ethyl acetate, filtered through Celite and washed with water and brine. The organic extract was dried over anhydrous sodium sulfate, concentrated and purified on a silica gel column using ethyl acetate and hexanes to yield 300 mg of the title compound (59% yield). HRMS calcd for $C_{38}H_{44}O_9F_2$ [M+Na]$^+$ 705.2845, observed 705.2843.

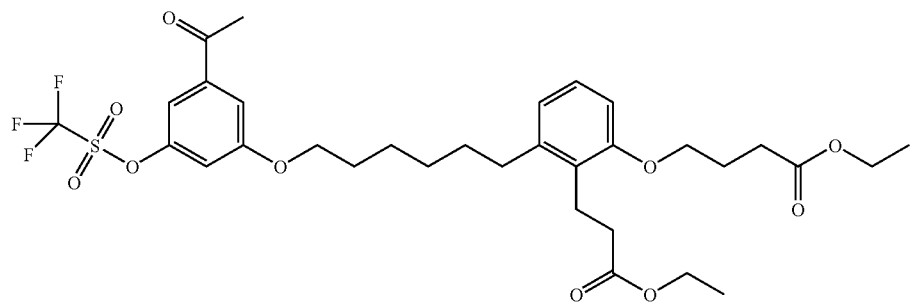

Step 5: 4-[3-{6-[3-Acetyl-5-(2,2-difluoro-benzo[1,3]dioxol-5-yl)-phenoxy]-hexyl}-2-(2-carboxy-ethyl)-phenoxy]-butyric acid

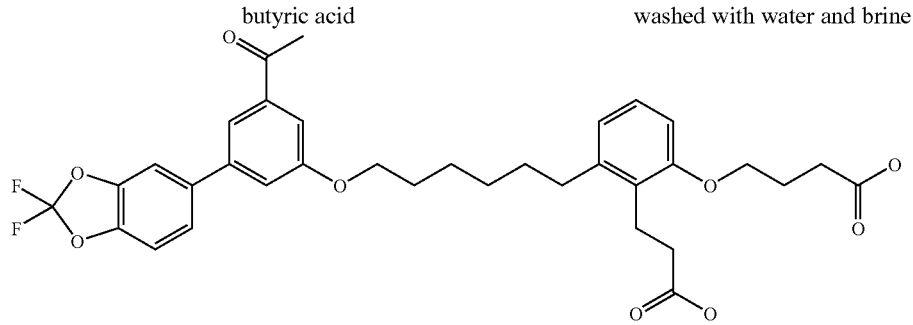

To a solution of 4-[3-{6-[3-acetyl-5-(2,2-difluoro-benzo[1,3]dioxol-5-yl)-phenoxy]-hexyl}-2-(2-ethoxycarbonyl-ethyl)-phenoxy]-butyric acid ethyl ester (300 mg) in ethanol (5 mL) was added a solution of NaOH (176 mg) in water (2 mL) and the resulting mixture was stirred at room temperature for 5 h. Then the reaction mixture was diluted with water, acidified with 3 N HCl and extracted into ethyl acetate. The organic extract was washed with brine, dried over anhydrous sodium sulfate, concentrated under reduced pressure and purified on a reverse-phase HPLC to yield 137 mg of the title compound (50% yield). HRMS calcd for $C_{34}H_{36}O_9F_2$ [M+Na]$^+$ 649.2219, observed 649.2222.

Example 70

4-[3-[6-(3-Benzo[1,3]dioxol-5-yl-5-isobutyryl-phenoxy)-hexyl]-2-(2-carboxy-ethyl)-phenoxy]-butyric acid

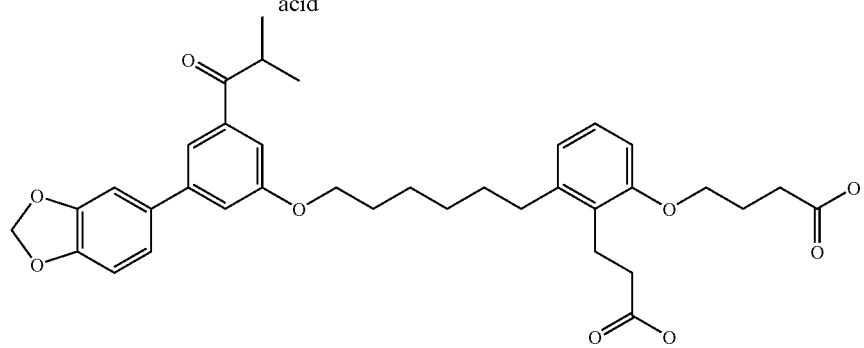

Step 1:
3-Bromo-5-(4-methoxy-benzyloxy)-benzonitrile

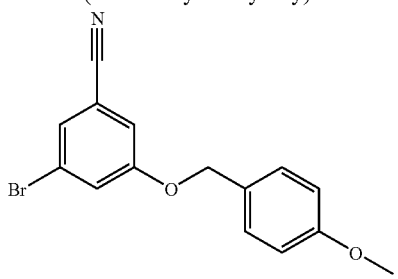

p-Methoxybenzyl alcohol (2.6 mL) was dissolved in anhydrous DMF (50 mL) and NaH (808 mg, 60% dispersion in oil) was added in several portions. After gas evolution ceased, 3,5-dibromobenzonitrile (5.0 g) was added and the reaction mixture was stirred at 70° C. After 2 h additional amount of NaH (147 mg) was added and heating was continued for 6 h. The reaction mixture was diluted with ethyl acetate and washed with water and brine. The organic extract was dried over anhydrous sodium sulfate, concentrated and purified on a silica gel column using ethyl acetate and hexanes to yield 3.1 g of the title compound (51% yield). HRMS calcd for $C_{15}H_{12}O_2BrN$ M$^+$ 371.0051, observed 371.0048.

Step 2: 3-Benzo[1,3]dioxol-5-yl-5-(4-methoxy-benzyloxy)-benzonitrile

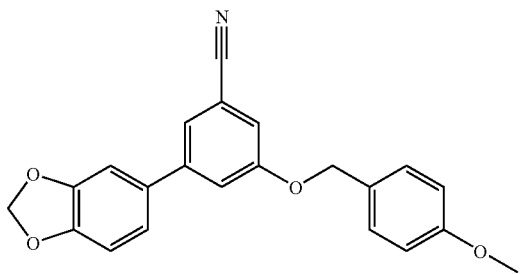

To a solution of 3-bromo-5-(4-methoxy-benzyloxy)-benzonitrile (1.1 g) in 1,2-dimethoxyethane (10 mL) were added 3,4-methylenedioxyphenylboronic acid (860 mg), 2 M aq. sodium carbonate solution (3.5 mL) and Pd(PPh$_3$)$_4$ (40 mg) and the resulting mixture was stirred at 90° C. for 4 h. Then the reaction mixture was diluted with ethyl acetate, filtered through Celite and washed with water and brine. The organic extract was dried over anhydrous sodium sulfate, filtered through a silica pad, concentrated and triturated with diethyl ether to yield 1.0 g of the title compound (89% yield). HRMS calcd for $C_{22}H_{17}O_4N$ M$^+$ 359.1158, observed 359.1158.

Step 3: 1-[3-Benzo[1,3]dioxol-5-yl-5-(4-methoxy-benzyloxy)-phenyl]-2-methyl-propan-1-one

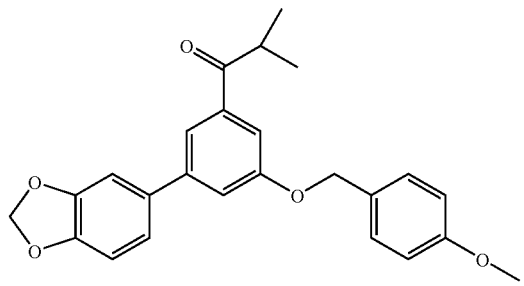

To a solution of 3-benzo[1,3]dioxol-5-yl-5-(4-methoxy-benzyloxy)-benzonitrile (500 mg) in anhydrous THF (10 mL) were added a solution of isopropylmagnesium chloride (2.1 mL of 2 M solution in diethyl ether) and catalytic amount of cuprous bromide (4 mg). The resulting reaction mixture was refluxed for 2 h. After it was cooled down, 10% sulfuric acid (5 mL) was added and stirring was continued for 30 min at room temperature. Then the reaction mixture was diluted with diethyl ether, washed with water and brine. The organic extract was dried over anhydrous sodium sulfate, concentrated and purified on a silica gel column using ethyl acetate and hexanes to yield 358 mg of the title compound (64% yield). HRMS calcd for $C_{25}H_{24}O_5$ [M+H]$^+$ 405.1697, observed 405.1698.

Step 4: 1-(3-Benzo[1,3]dioxol-5-yl-5-hydroxy-phenyl)-2-methyl-propan-1-one

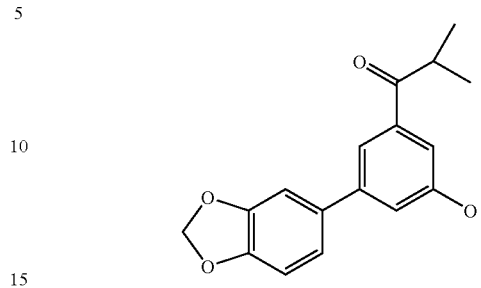

1-[3-Benzo[1,3]dioxol-5-yl-5-(4-methoxy-benzyloxy)-phenyl]-2-methyl-propan-1-one (355 mg) was dissolved in glacial acetic acid (3 mL) and heated at 100° C. overnight. The solvent was removed under reduced pressure and the residue was purified on a silica gel column using ethyl acetate and hexanes to yield 205 mg of orange solid, which was dissolved in small amount of ethyl acetate and triturated with hexanes to yield 112 mg of the title compound (45% yield). HRMS calcd for $C_{17}H_{16}O_4$ [M+H]$^+$ 281.1122, observed 281.1121.

Step 5: 4-[3-[6-(3-Benzo[1,3]dioxol-5-yl-5-isobutyryl-phenoxy)-hexyl]-2-(2-ethoxycarbonyl-ethyl)-phenoxy]-butyric acid ethyl ester

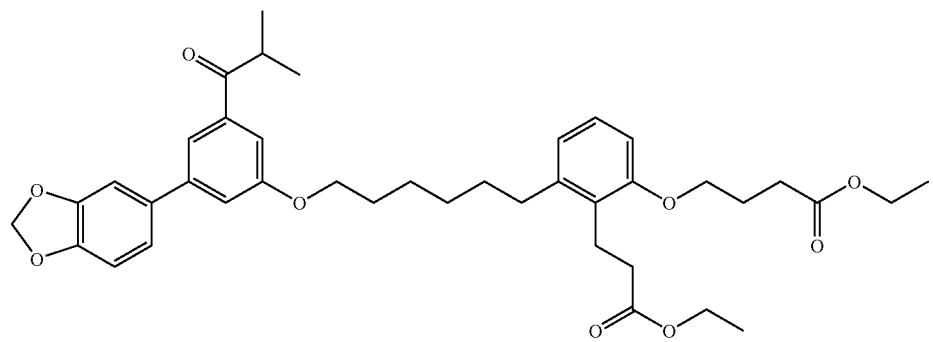

To a solution of 1-(3-benzo[1,3]dioxol-5-yl-5-hydroxy-phenyl)-2-methyl-propan-1-one (109 mg) in a mixture of acetone and DMF (2:1, 3 mL) were added cesium carbonate (624 mg) and 4-[3-(6-bromo-hexyl)-2-(2-ethoxycarbonyl-ethyl)-phenoxy]-butyric acid ethyl ester (190 mg). The resulting mixture was stirred at 75° C. overnight. Then the insoluble material was filtered out and the filtrate was diluted with ethyl acetate and washed with water and brine. The organic extract was dried over anhydrous sodium sulfate, concentrated and purified on a silica gel column using ethyl acetate and hexanes to yield 194 mg of the title compound (75% yield). HRMS calcd for $C_{40}H_{50}O_9$ [M+Na]$^+$ 697.3347, observed 697.3344.

Step 6: 4-[3-[6-(3-Benzo[1,3]dioxol-5-yl-5-isobutyryl-phenoxy)-hexyl]-2-(2-carboxy-ethyl)-phenoxy]-butyric acid

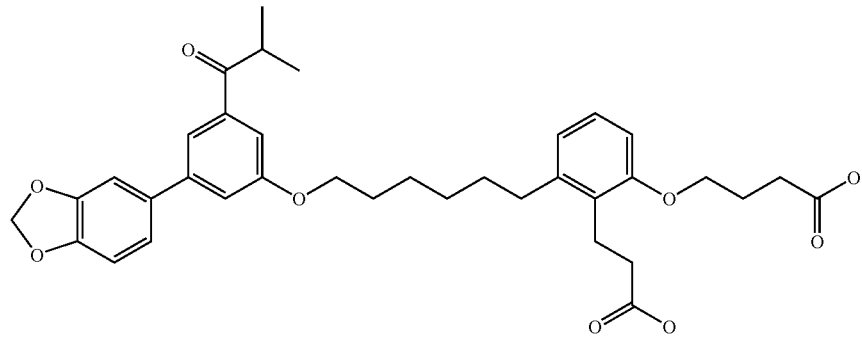

To a solution of 4-[3-[6-(3-benzo[1,3]dioxol-5-yl-5-isobutyryl-phenoxy)-hexyl]-2-(2-ethoxycarbonyl-ethyl)-phenoxy]-butyric acid ethyl ester (191 mg) in ethanol (2 mL) was added 10 M NaOH (566 µL) and the resulting mixture was stirred at room temperature for 5 h. Then the reaction mixture was diluted with water, acidified with 3 N HCl and extracted into ethyl acetate. The organic extract was washed with brine, dried over anhydrous sodium sulfate, concentrated under reduced pressure and purified on a reverse-phase HPLC to yield 50 mg of the title compound (29% yield). HRMS calcd for $C_{36}H_{42}O_9$ $[M+Na]^+$ 641.2721, observed 641.2720.

Example 71

4-[3-[6-(3-Benzo[1,3]dioxol-5-yl-5-propionyl-phenoxy)-hexyl]-2-(2-carboxy-ethyl)-phenoxy]-butyric acid To a solution of 3-benzo[1,3]dioxol-5-yl-5-(4-methoxybenzyloxy)-benzonitrile (250 mg) in anhydrous THF (3 mL) were added a solution of ethylmagnesium chloride (517 µL of 2 M solution in diethyl ether) and catalytic amount of cuprous bromide (2 mg). The resulting reaction mixture was refluxed for 1 h and then additional amount of ethylmagnesium chloride (517 µL of 2 M solution in diethyl ether) was added and heating was continued for 30 min. After it was cooled down, 10% sulfuric acid (1.5 mL) was added and stirring was continued for 30 min at room temperature. Then the reaction mixture was diluted with diethyl ether, washed with water and brine. The organic extract was dried over anhydrous sodium sulfate, concentrated and purified on a silica gel column using ethyl acetate and hexanes to yield 136 mg of the title compound (50% yield). HRMS calcd for $C_{24}H_{22}O_5$ $[M+H]^+$ 391.1540, observed 391.1541.

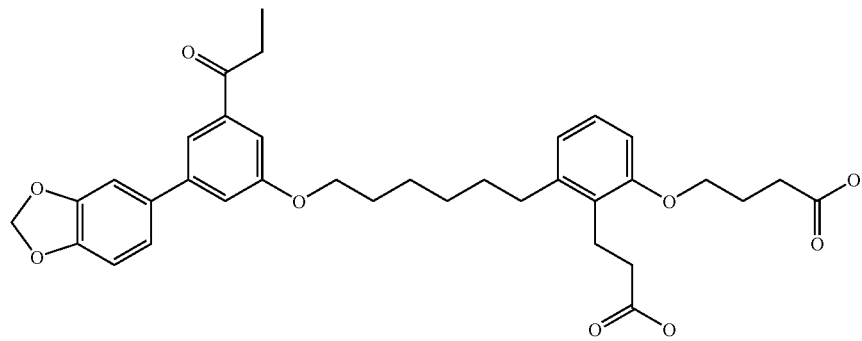

Step 1: 1-[3-Benzo[1,3]dioxol-5-yl-5-(4-methoxybenzyloxy)-phenyl]-propan-1-one

Step 2: 1-(3-Benzo[1,3]dioxol-5-yl-5-hydroxy-phenyl)-propan-1-one

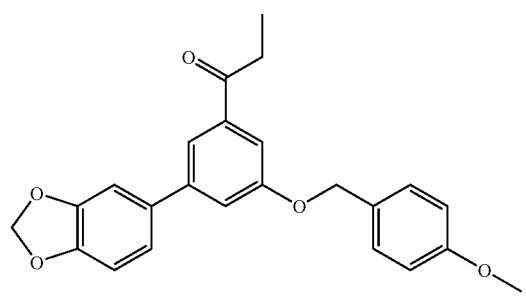

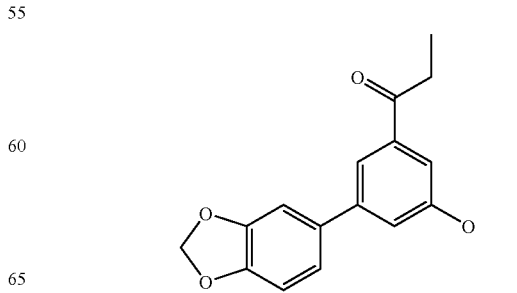

1-[3-Benzo[1,3]dioxol-5-yl-5-(4-methoxy-benzyloxy)-phenyl]-propan-1-one (135 mg) was dissolved in glacial acetic acid (2 mL) and heated at 100° C. for 2 days. The solvent was removed under reduced pressure and the residue was purified on a silica gel column using ethyl acetate and hexanes to yield 28.5 mg of the title compound (30% yield). HRMS calcd for $C_{16}H_{14}O_4$ [M+H]$^+$ 271.0965, observed 271.0964.

Step 3: 4-[3-[6-(3-Benzo[1,3]dioxol-5-yl-5-propionyl-phenoxy)-hexyl]-2-(2-ethoxycarbonyl-ethyl)-phenoxy]-butyric acid ethyl ester

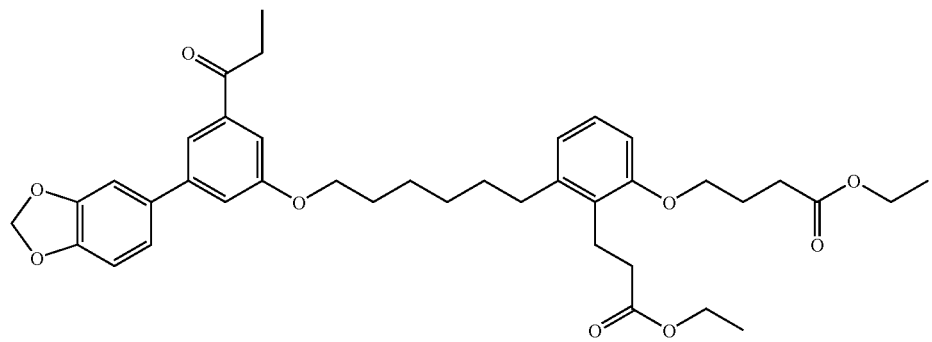

The title compound was prepared by the same method described in Example 70, Step 5. Starting with 28.5 mg of 1-(3-benzo[1,3]dioxol-5-yl-5-hydroxy-phenyl)-propan-1-one, 44 mg (66% yield) of the title compound were obtained. HRMS calcd for $C_{39}H_{48}O_9$ [M+Na]$^+$ 683.3190, observed 683.3191.

Step 4: 4-[3-[6-(3-Benzo[1,3]dioxol-5-yl-5-propionyl-phenoxy)-hexyl]-2-(2-carboxy-ethyl)-phenoxy]-butyric acid

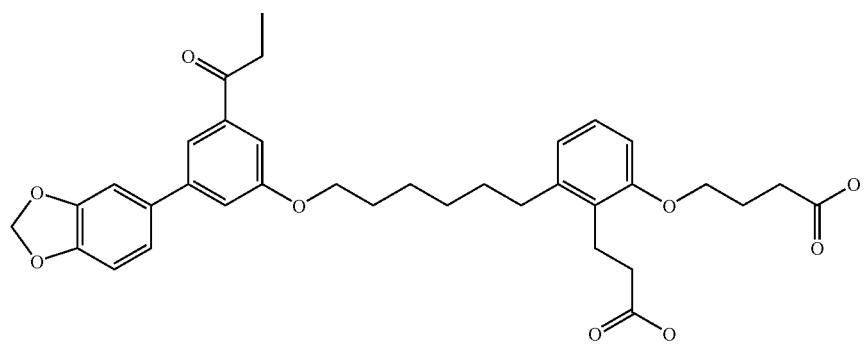

The title compound was prepared by the same method described in Example 70, Step 6. Starting with 41 mg of 4-[3-[6-(3-benzo[1,3]dioxol-5-yl-5-propionyl-phenoxy)-hexyl]-2-(2-ethoxycarbonyl-ethyl)-phenoxy]-butyric acid ethyl ester, 34 mg (94% yield) of the title compound were obtained. HRMS calcd for $C_{35}H_{40}O_9$ [M+Na]$^+$ 627.2564, observed 627.2566.

Example 72

4-[3-[6-(3-Benzo[1,3]dioxol-5-yl-5-cyclopropan-
ecarbonyl-phenoxy)-hexyl]-2-(2-carboxy-ethyl)-
phenoxy]-butyric acid

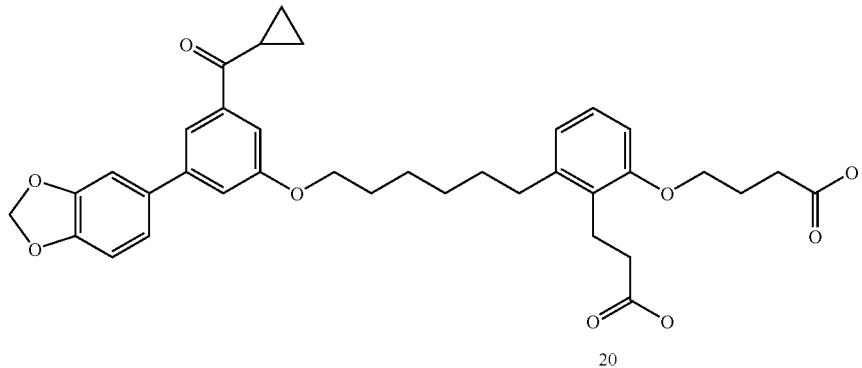

Step 1: [3-Benzo[1,3]dioxol-5-yl-5-(4-methoxy-benzyloxy)-phenyl]-cyclopropyl-methanone Step 2: (3-Benzo[1,3]dioxol-5-yl-5-hydroxy-phenyl)-cyclopropyl-methanone

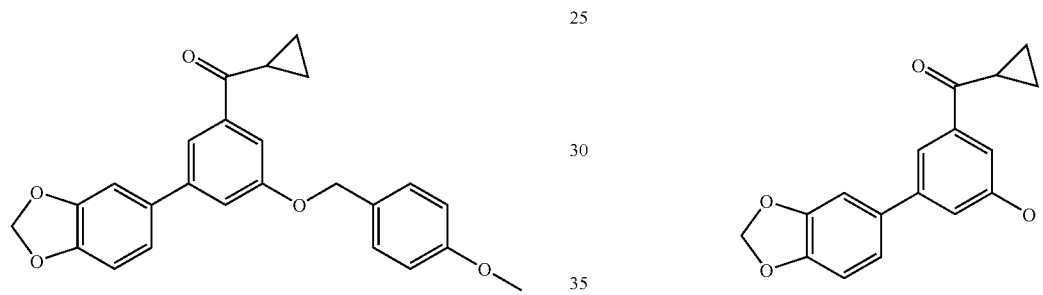

To a solution of 3-benzo[1,3]dioxol-5-yl-5-(4-methoxy-benzyloxy)-benzonitrile (250 mg) in anhydrous THF (3 mL) were added a solution of cyclopropylmagnesium chloride (4.1 mL of 0.5 M solution in THF) and catalytic amount of cuprous bromide (2 mg). The resulting reaction mixture was refluxed for 1.5 h. After it was cooled down, 10% sulfuric acid (1.5 mL) was added and stirring was continued for 30 min at room temperature. Then the reaction mixture was diluted with diethyl ether, washed with water and brine. The organic extract was dried over anhydrous sodium sulfate, concentrated and purified on a silica gel column using ethyl acetate and hexanes to yield 253 mg of the title compound (91% yield). HRMS calcd for $C_{25}H_{22}O_5$ [M+H]$^+$ 403.1540, observed 403.1537.

[3-Benzo[1,3]dioxol-5-yl-5-(4-methoxy-benzyloxy)-phenyl]-cyclopropyl-methanone (250 mg) was dissolved in glacial acetic acid (3 mL) and heated at 100° C. overnight. The solvent was removed under reduced pressure and the residue was purified on a silica gel column using ethyl acetate and hexanes to yield 138 mg of the title compound (79% yield). HRMS calcd for $C_{17}H_{14}O_4$ [M+H]$^+$ 283.0965, observed 283.0964.

Step 3: 4-[3-[6-(3-Benzo[1,3]dioxol-5-yl-5-cyclo-
propanecarbonyl-phenoxy)-hexyl]-2-(2-ethoxycarbo-
nyl-ethyl)-phenoxy]-butyric acid ethyl ester

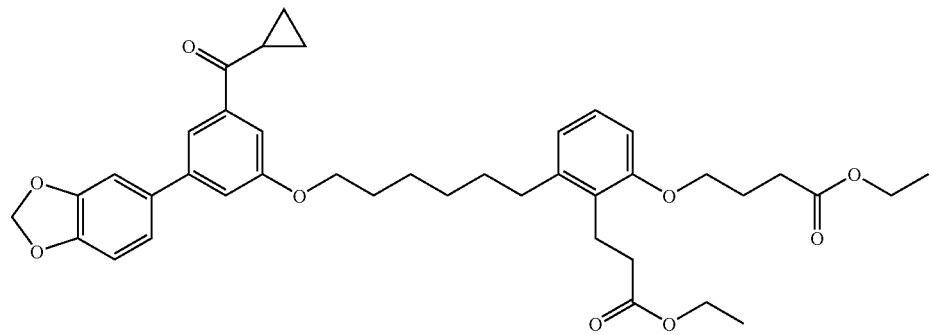

The title compound was prepared by the same method described in Example 70, Step 5. Starting with 35 mg of (3-benzo[1,3]dioxol-5-yl-5-hydroxy-phenyl)-cyclopropyl-methanone, 74 mg (92% yield) of the title compound were obtained. HRMS calcd for $C_{40}H_{48}O_9$ [M+Na]$^+$ 695.3190, observed 695.3191.

Step 4: 4-[3-[6-(3-Benzo[1,3]dioxol-5-yl-5-cyclopropanecarbonyl-phenoxy)-hexyl]-2-(2-carboxy-ethyl)-phenoxy]-butyric acid

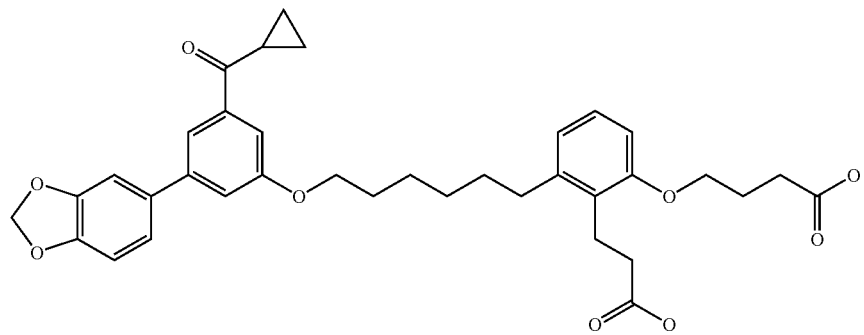

The title compound was prepared by the same method described in Example 70, Step 6. Starting with 70 mg of 4-[3-[6-(3-benzo[1,3]dioxol-5-yl-5-cyclopropanecarbonyl-phenoxy)-hexyl]-2-(2-ethoxycarbonyl-ethyl)-phenoxy]-butyric acid ethyl ester, 48 mg (71% yield) of the title compound were obtained. HRMS calcd for $C_{36}H_{40}O_9$ [M+H]$^+$ 617.2745, observed 617.2745.

Example 73

4-[3-[6-(3-Benzo[1,3]dioxol-5-yl-5-cyclopentanecarbonyl-phenoxy)-hexyl]-2-(2-carboxy-ethyl)-phenoxy]-butyric acid

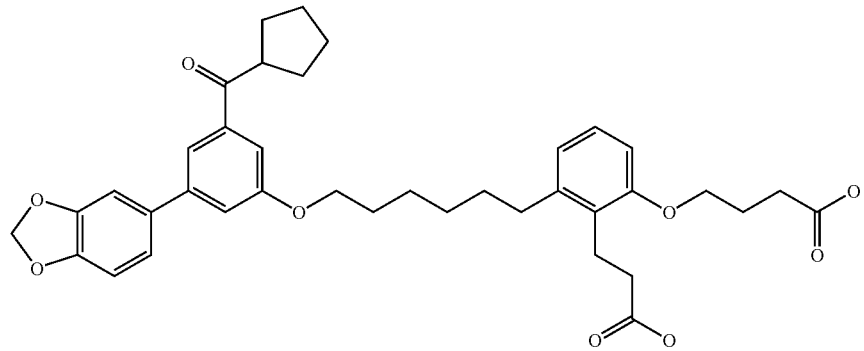

Step 1:
Cyclopentyl-(3,5-dimethoxy-phenyl)-methanone

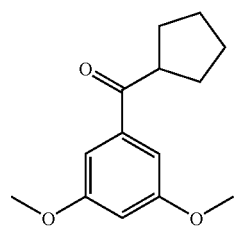

To a solution of 3,5-dimethoxybenzonitrile (5.0 g) in anhydrous THF (60 mL) were added a solution of cyclopentyl-magnesium chloride (20 mL of 2 M solution in diethyl ether) and cuprous bromide (88 mg). The resulting reaction mixture was refluxed for 1 h. Then water (10 mL) and 10% sulfuric acid (20 mL) were added and the resulting mixture was stirred at room temperature overnight. Then the reaction mixture was diluted with diethyl ether and washed with water and brine. The organic extract was dried over anhydrous sodium sulfate, concentrated and purified on a silica gel column using ethyl acetate and hexanes to yield 5.9 of the title compound (82% yield). HRMS calcd for $C_{14}H_{18}O_3$ [M+H]$^+$ 253.1329, observed 253.1328.

Step 2:
Cyclopentyl-(3,5-dihydroxy-phenyl)-methanone

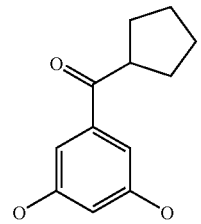

To a solution of cyclopentyl-(3,5-dimethoxy-phenyl)-methanone (234 mg) in anhydrous dichloromethane (5 mL) cooled in dry ice/acetone bath was added dropwise a solution of boron tribromide (4 mL of 1 M solution in dichloromethane). After the addition was completed, the cooling bath was removed and the reaction mixture was stirred at room temperature overnight. Unreacted boron tribromide was quenched with methanol. Then the reaction mixture was diluted with ethyl acetate and washed with water and brine. The organic extract was dried over anhydrous sodium sulfate, concentrated and purified on a silica gel column using ethyl acetate and hexanes to yield 200 mg of the title compound (97% yield). Note: the title compound decomposes on air. HRMS calcd for $C_{12}H_{14}O_3$ [M+H]$^+$ 207.1016, observed 207.1016.

Step 3: Trifluoro-methanesulfonic acid 3-cyclopentanecarbonyl-5-trifluoro methanesulfonyloxy-phenyl ester

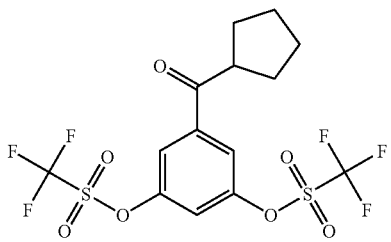

Cyclopentyl-(3,5-dihydroxy-phenyl)-methanone (1.9 g) was suspended in 40 mL of dichloromethane and then pyridine (3.0 mL) was added. The resulting clear solution was cooled to 0° C. and 3.2 mL of triflic anhydride were added dropwise. After addition was completed, the cooling bath was removed and the reaction mixture was stirred at room temperature for 1 h and then quenched with 1 N hydrochloric acid. The organic solution was separated and washed with saturated sodium bicarbonate solution and brine and dried over anhydrous sodium sulfate. The solvent was removed under reduced pressure and the residue was purified on a silica gel column using ethyl acetate and hexanes to yield 1.5 g of the title compound (34% yield). HRMS calcd for $C_{14}H_{12}O_7S_2F_6$ [M−H]⁻ 468.9856, observed 468.9854.

Step 4: Trifluoro-methanesulfonic acid 3-cyclopentanecarbonyl-5-hydroxy-phenyl ester

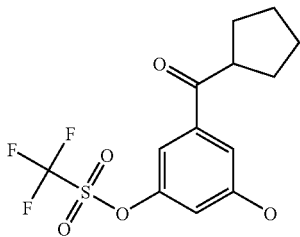

Trifluoro-methanesulfonic acid 3-cyclopentanecarbonyl-5-trifluoromethanesulfonyloxy-phenyl ester (1.5 g) was dissolved in 1,2-dimethoxyethane (30 mL), followed by addition of cesium carbonate (1.5 g). The resulting suspension was stirred at 80° C. for 3 h and then quenched with saturated solution of ammonium chloride. The solution was then extracted with diethyl ether and combined etherate extracts were washed with brine and dried over anhydrous sodium sulfate. The filtrate was concentrated under reduced pressure and purified on a silica gel column using ethyl acetate and hexanes to yield 300 mg of the title compound (28% yield). HRMS calcd for $C_{13}H_{13}O_5S_1F_3$ [M+H]⁺ 339.0509, observed 339.0509.

Step 5: (3-Benzo[1,3]dioxol-5-yl-5-hydroxy-phenyl)-cyclopentyl-methanone

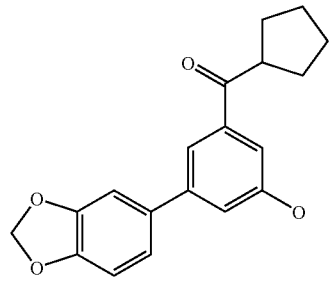

To a solution of trifluoro-methanesulfonic acid 3-cyclopentanecarbonyl-5-hydroxy-phenyl ester (300 mg) in 1,2-dimethoxyethane (4 mL) were added 3,4-methylenedioxyphenylboronic acid (295 mg), 2 M aq. sodium carbonate solution (0.9 mL) and Pd(PPh₃)₄ (10 mg) and the resulting mixture was stirred at 90° C. for 3 h. Then the reaction mixture was diluted with ethyl acetate, filtered through Celite and washed with water and brine. The organic extract was dried over anhydrous sodium sulfate, concentrated and purified on a silica gel column using ethyl acetate and hexanes to yield 100 mg of the title compound (36% yield). HRMS calcd for $C_{19}H_{18}O_4$ [M+H]⁺ 311.1278, observed 311.1277.

Step 6: 4-[3-[6-(3-Benzo[1,3]dioxol-5-yl-5-cyclopentanecarbonyl-phenoxy)-hexyl]-2-(2-ethoxycarbonyl-ethyl)-phenoxy]-butyric acid ethyl ester

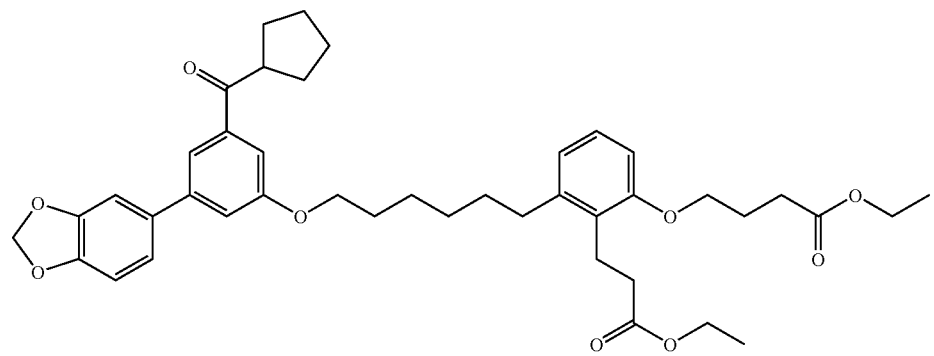

The title compound was prepared by the same method described in Example 70, Step 5. Starting with 94 mg of (3-benzo[1,3]dioxol-5-yl-5-hydroxy-phenyl)-cyclopentyl-methanone, 98 mg (47% yield) of the title compound were obtained. HRMS calcd for $C_{42}H_{52}O_9$ [M+Na]$^+$ 723.3503, observed 723.3509.

Step 7: 4-[3-[6-(3-Benzo[1,3]dioxol-5-yl-5-cyclo-pentanecarbonyl-phenoxy)-hexyl]-2-(2-carboxy-ethyl)-phenoxy]-butyric acid

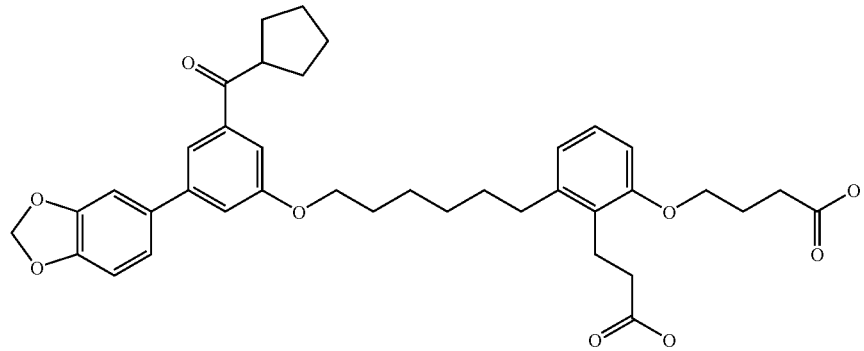

The title compound was prepared by the same method descirbed in Example 70, Step 6. Starting with 97 mg of 4-[3-[6-(3-benzo[1,3]dioxol-5-yl-5-cyclopentanecarbonyl-phenoxy)-hexyl]-2-(2-ethoxycarbonyl-ethyl)-phenoxy]-butyric acid ethyl ester, 3.9 mg (4% yield) of the title compound were obtained. HRMS calcd for $C_{38}H_{44}O_9$ [M+H]$^+$ 645.3058, observed 645.3056.

Example 74

Assay of Compounds for Inhibition of LTB$_4$ Activity $Ca^{2+}$ Flux Assay for LTB4 Antagonist Assay
Cell Culture Conditions:
Human leukemia HL-60 cells endogenously expressing BLT1 and BLT2 receptors were cultured in RPMI-1640 medium supplemented with 20% fetal bovine serum, 2 mM glutamine, 100 U/ml penicillin and 100 ug/ml streptomycin. Seventy two hours prior to experiment cells are counted using ViaCount reagent, centrifuged and resuspended at $2.0 \times 10^5$ cells/ml density with the complete growth media containing 1 µM Retinoic Acid (Sigma).
Dye Loading and Assay:
On a day of the experiment loading buffer (Calcium-3 Assay Kit, Molecular Devices) was prepared by dissolving the contents of one vial (Express Kit) into 500 ml Hank's Balanced Salt Solution containing 20 mM HEPES and 5 mM probenecid. Equal volume of the loading buffer was mixed with the replacement buffer (Hank's Balanced Salt Solution containing 20 mM HEPES, 0.05% BSA and 5 mM probenecid). Retinoic Acid induced HL-60 cells were counted using ViaCount reagent, centrifuged and resuspended at $2.0 \times 10^6$ cells/ml density with the loading buffer/replacement buffer, dispensed into 384 well black/clear microplates (Falcon) (25 µl/well) and placed in a 37° C./5% $CO_2$ incubator for 1 hour.
During the incubation, test compounds were prepared at 6× the desired concentration in HBSS/20 mM HEPES/0.05% BSA as well as LTB4 (Biomol) was prepared at 2.2× concentration in HBSS/20 mM HEPES/0.5% BSA buffer.

After the incubation, both the cell and compound plates were brought to the FLIPR and 5 µl of the diluted compounds were transferred to the cell plates by the FLIPR. Plates were then incubated for 30 min at room temperature. After the ½ hour incubation, plates were returned to the FLIPR and 25 µl of 2.2×LTB4 was added to the cell plates. During the assay, fluorescence readings were taken simultaneously from all 384 wells of the cell plate every 1.5 seconds. Five readings were taken to establish a stable baseline, then 25 µl (LTB4) of sample was rapidly and simultaneously added to each well of the cell plate. The fluorescence was continuously monitored before, during and after sample addition for a total elapsed time of 100 seconds. Responses (increase in peak fluorescence) in each well following agonist addition was determined. The initial fluorescence reading from each well, prior to ligand stimulation, was used a zero baseline value for the data from that well. The responses are expressed as % inhibition of the neutral control (neural control: wells that received buffer plus DMSO but no test compound).

| Assay results | | |
|---|---|---|
| Example # | Compound name | LTB4 antagonism (HL-60 FLIPR) (nM) |
| 1 | 4-[3-[6-(3-Benzo[1,3]dioxol-5-yl-5-hydroxymethyl-phenoxy)-hexyl]-2-(2-carboxy-ethyl)-phenoxy]-butyric acid | 3.1 |
| 2 | 4-{2-(2-Carboxy-ethyl)-3-[6-(5-hydroxymethyl-biphenyl-3-yloxy)-hexyl]-phenoxy}-butyric acid | 24.68 |
| 3 | 4-{2-(2-Carboxy-ethyl)-3-[6-(3-hydroxymethyl-5-thiophen-3-yl-phenoxy)-hexyl]-phenoxy}-butyric acid | 62.46 |
| 4 | 4-{2-(2-Carboxy-ethyl)-3-[6-(4'-fluoro-5-hydroxymethyl-biphenyl-3-yloxy)- | 29.63 |

Assay results

| Example # | Compound name | LTB4 antagonism (HL-60 FLIPR) (nM) |
|---|---|---|
| 5 | hexyl]-phenoxy}-butyric acid<br>4-{2-(2-Carboxy-ethyl)-3-[6-(4'-chloro-5-hydroxymethyl-biphenyl-3-yloxy)-hexyl]-phenoxy}-butyric acid | 43.08 |
| 6 | 4-(2-(2-Carboxy-ethyl)-3-{6-[3-(2,3-dihydro-benzo[1,4]dioxin-6-yl)-5-hydroxymethyl-phenoxy]-hexyl}-phenoxy)-butyric acid | 7.39 |
| 7 | 4-{2-(2-Carboxy-ethyl)-3-[6-(5-hydroxymethyl-4'-methanesulfonyl-biphenyl-3-yloxy)-hexyl]-phenoxy}-butyric acid | 83.21 |
| 8 | 4-[3-[6-(3-Benzo[1,3]dioxol-5-yl-5-methoxymethyl-phenoxy)-hexyl]-2-(2-carboxy-ethyl)-phenoxy]-butyric acid | 0.14 |
| 9 | 4-{2-(2-Carboxy-ethyl)-3-[6-(5-methoxymethyl-biphenyl-3-yloxy)-hexyl]-phenoxy}-butyric acid | 1.93 |
| 10 | 4-{2-(2-Carboxy-ethyl)-3-[6-(4'-fluoro-5-methoxymethyl-biphenyl-3-yloxy)-hexyl]-phenoxy}-butyric acid | 2.52 |
| 11 | 4-{2-(2-Carboxy-ethyl)-3-[6-(4'-chloro-5-methoxymethyl-biphenyl-3-yloxy)-hexyl]-phenoxy}-butyric acid | 1.37 |
| 12 | 4-(2-(2-Carboxy-ethyl)-3-{6-[3-(2,3-dihydro-benzo[1,4]dioxin-6-yl)-5-methoxymethyl-phenoxy]-hexyl}-phenoxy)-butyric acid | 1.38 |
| 13 | 4-(2-(2-Carboxy-ethyl)-3-{6-[3-methoxymethyl-5-(4-methyl-thiophen-3-yl)-phenoxy]-hexyl}-phenoxy)-butyric acid | 140.16 |
| 14 | 4-{2-(2-Carboxy-ethyl)-3-[6-(3'-fluoro-5-methoxymethyl-biphenyl-3-yloxy)- | 1.47 |
| 15 | hexyl]-phenoxy}-butyric acid<br>4-{2-(2-Carboxy-ethyl)-3-[6-(2'-fluoro-5-methoxymethyl-biphenyl-3-yloxy)-hexyl]-phenoxy}-butyric acid | 5.98 |
| 16 | 4-{2-(2-Carboxy-ethyl)-3-[6-(3',5'-difluoro-5-methoxymethyl-biphenyl-3-yloxy)-hexyl]-phenoxy}-butyric acid | 14.85 |
| 17 | 4-{2-(2-Carboxy-ethyl)-3-[6-(5-methoxymethyl-4'-trifluoromethyl-biphenyl-3-yloxy)-hexyl]-phenoxy}-butyric acid | 1.62 |
| 18 | 4-{2-(2-Carboxy-ethyl)-3-[6-(3'-chloro-5-methoxymethyl-biphenyl-3-yloxy)-hexyl]-phenoxy}-butyric acid | 13.38 |
| 19 | 4-{2-(2-Carboxy-ethyl)-3-[6-(3'-methoxy-5-methoxymethyl-biphenyl-3-yloxy)-hexyl]-phenoxy}-butyric acid | 9.44 |
| 20 | 4-{2-(2-Carboxy-ethyl)-3-[6-(5-methoxymethyl-4'-trifluoromethoxy-biphenyl-3-yloxy)-hexyl]-phenoxy}-butyric acid | 15.14 |
| 21 | 4-{2-(2-Carboxy-ethyl)-3-[6-(3',4'-difluoro-5-methoxymethyl-biphenyl-3-yloxy)-hexyl]-phenoxy}-butyric acid | 2.66 |
| 22 | 4-{2-(2-Carboxy-ethyl)-3-[6-(3-methoxymethyl-5-pyrimidin-5-yl-phenoxy)-hexyl]-phenoxy}-butyric acid | 339.3 |
| 23 | 4-(2-(2-Carboxy-ethyl)-3-{6-[3-(1H-indol-5-yl)-5-methoxymethyl-phenoxy]-hexyl}-phenoxy)-butyric acid | 30.19 |
| 24 | 4-{2-(2-Carboxy-ethyl)-3-[6-(4'-methanesulfonyl-5-methoxymethyl-biphenyl-3-yloxy)-hexyl]-phenoxy}-butyric acid | 6.83 |
| 25 | 4-[3-[6-(3-Benzo[1,3]dioxol-5- | 1.06 |

-continued

Assay results

| Example # | Compound name | LTB4 antagonism (HL-60 FLIPR) (nM) |
|---|---|---|
|  | yl-5-ethoxymethyl-phenoxy)-hexyl]-2-(2-carboxy-ethyl)-phenoxy]-butyric acid |  |
| 26 | 4-{2-(2-Carboxy-ethyl)-3-[6-(5-ethoxymethyl-4'-fluoro-biphenyl-3-yloxy)-hexyl]-phenoxy}-butyric acid | 11.88 |
| 27 | 4-{2-(2-Carboxy-ethyl)-3-[6-(5-ethoxymethyl-4'-trifluoromethyl-biphenyl-3-yloxy)-hexyl]-phenoxy}-butyric acid | 6.24 |
| 28 | 4-{2-(2-Carboxy-ethyl)-3-[6-(4'-chloro-5-ethoxymethyl-biphenyl-3-yloxy)-hexyl]-phenoxy}-butyric acid | 6.51 |
| 29 | 4-{2-(2-Carboxy-ethyl)-3-[6-(5-ethoxymethyl-4'-methanesulfonyl-biphenyl-3-yloxy)-hexyl]-phenoxy}-butyric acid | 15.96 |
| 30 | 4-[3-[6-(3-Benzo[1,3]dioxol-5-yl-5-dimethylaminomethyl-phenoxy)-hexyl]-2-(2-carboxy-ethyl)-phenoxy]-butyric acid | 0.1 |
| 31 | 4-{2-(2-Carboxy-ethyl)-3-[6-(3-dimethylaminomethyl-5-thiophen-3-yl-phenoxy)-hexyl]-phenoxy}-butyric acid | 0.11 |
| 32 | 4-{2-(2-Carboxy-ethyl)-3-[6-(5-dimethylaminomethyl-biphenyl-3-yloxy)-hexyl]-phenoxy}-butyric acid | 0.1 |
| 33 | 4-{2-(2-Carboxy-ethyl)-3-[6-(5-dimethylaminomethyl-4'-fluoro-biphenyl-3-yloxy)-hexyl]-phenoxy}-butyric acid | 0.11 |
| 34 | 4-{2-(2-Carboxy-ethyl)-3-[6-(4'-chloro-5-dimethylaminomethyl-biphenyl-3-yloxy)-hexyl]-phenoxy}-butyric acid | 0.24 |
| 35 | 4-{2-(2-Carboxy-ethyl)-3-[6-(5-dimethylaminomethyl-3'-fluoro-4'-methyl-biphenyl-3-yloxy)-hexyl]-phenoxy}-butyric acid | 0.16 |
| 36 | 4-{2-(2-Carboxy-ethyl)-3-[6-(5-dimethylaminomethyl-3'-fluoro-biphenyl-3-yloxy)-hexyl]-phenoxy}-butyric acid | 0.14 |
| 37 | 4-{2-(2-Carboxy-ethyl)-3-[6-(5-dimethylaminomethyl-4'-trifluoromethyl-biphenyl-3-yloxy)-hexyl]-phenoxy}-butyric acid | 0.37 |
| 38 | 4-{2-(2-Carboxy-ethyl)-3-[6-(5-dimethylaminomethyl-4'-methanesulfonyl-biphenyl-3-yloxy)-hexyl]-phenoxy}-butyric acid | 2.22 |
| 39 | 4-{2-(2-Carboxy-ethyl)-3-[6-(5-dimethylaminomethyl-3'-methanesulfonyl-biphenyl-3-yloxy)-hexyl]-phenoxy}-butyric acid | 70.81 |
| 40 | 4-{2-(2-Carboxy-ethyl)-3-[6-(3-dimethylaminomethyl-5-pyridin-4-yl-phenoxy)-hexyl]-phenoxy}-butyric acid | 0.42 |
| 41 | 4-{2-(2-Carboxy-ethyl)-3-[6-(3-cyanomethyl-5-thiophen-3-yl-phenoxy)-hexyl]-phenoxy}-butyric acid | 15.19 |
| 42 | 4-{2-(2-Carboxy-ethyl)-3-[6-(5-cyanomethyl-biphenyl-3-yloxy)-hexyl]-phenoxy}-butyric acid | 22.98 |
| 43 | 4-[3-[6-(3-Benzo[1,3]dioxol-5-yl-5-ethoxy-phenoxy)-hexyl]-2-(2-carboxy-ethyl)-phenoxy]-butyric acid | 0.22 |
| 44 | 4-{2-(2-Carboxy-ethyl)-3-[6-(5-ethoxy-biphenyl-3-yloxy)-hexyl]-phenoxy}-butyric acid | 1.26 |
| 45 | 4-{2-(2-Carboxy-ethyl)-3-[6-(3-ethoxy-5-thiophen-3-yl-phenoxy)-hexyl]-phenoxy}-butyric acid | 0.4 |

| Example # | Compound name | LTB4 antagonism (HL-60 FLIPR) (nM) |
|---|---|---|
| 46 | 4-(2-(2-Carboxy-ethyl)-3-{6-[3-(2,3-dihydro-benzo[1,4]dioxin-6-yl)-5-ethoxy-phenoxy]-hexyl}-phenoxy)-butyric acid | 1.11 |
| 47 | 4-{2-(2-Carboxy-ethyl)-3-[6-(5-ethoxy-3'-fluoro-biphenyl-3-yloxy)-hexyl]-phenoxy}-butyric acid | 2.32 |
| 48 | 4-{2-(2-Carboxy-ethyl)-3-[6-(5-ethoxy-4'-fluoro-biphenyl-3-yloxy)-hexyl]-phenoxy}-butyric acid | 5.2 |
| 49 | 4-{2-(2-Carboxy-ethyl)-3-[6-(4'-chloro-5-ethoxy-biphenyl-3-yloxy)-hexyl]-phenoxy}-butyric acid | 6.05 |
| 50 | 4-{2-(2-Carboxy-ethyl)-3-[6-(5-ethoxy-3',4'-difluoro-biphenyl-3-yloxy)-hexyl]-phenoxy}-butyric acid | 8.27 |
| 51 | 4-{2-(2-Carboxy-ethyl)-3-[6-(5-ethoxy-4'-methanesulfonyl-biphenyl-3-yloxy)-hexyl]-phenoxy}-butyric acid | 2.1 |
| 52 | 4-(2-(2-Carboxy-ethyl)-3-{6-[3-(2-chloro-pyridin-4-yl)-5-ethoxy-phenoxy]-hexyl}-phenoxy)-butyric acid | 6.94 |
| 53 | 4-{2-(2-Carboxy-ethyl)-3-[6-(3-ethoxy-5-pyrimidin-5-yl-phenoxy)-hexyl]-phenoxy}-butyric acid | 79.31 |
| 54 | 4-(2-(2-Carboxy-ethyl)-3-{6-[3-ethoxy-5-(1H-indol-5-yl)-phenoxy]-hexyl}-phenoxy)-butyric acid | 34.16 |
| 55 | 4-(2-(2-Carboxy-ethyl)-3-{6-[3-ethoxy-5-(1H-indol-6-yl)-phenoxy]-hexyl}-phenoxy)-butyric acid | 6.69 |
| 56 | 4-[3-[6-(3-Benzothiazol-5-yl-5-ethoxy-phenoxy)-hexyl]-2-(2-carboxy-ethyl)-phenoxy]-butyric acid | 0.32 |
| 57 | 4-(2-(2-Carboxy-ethyl)-3-{6-[3-(2,2-difluoro-benzo[1,3]dioxol-5-yl)-5-ethoxy-phenoxy]-hexyl}-phenoxy)-butyric acid | 1.2 |
| 58 | 4-[3-[6-(5-Benzyloxy-biphenyl-3-yloxy)-hexyl]-2-(2-carboxy-ethyl)-phenoxy]-butyric acid | 74.58 |
| 59 | 4-[3-[6-(5-Benzyloxy-3'-fluoro-biphenyl-3-yloxy)-hexyl]-2-(2-carboxy-ethyl)-phenoxy]-butyric acid | 131.84 |
| 60 | 4-[3-[6-(3-Benzo[1,3]dioxol-5-yl-5-benzyloxy-phenoxy)-hexyl]-2-(2-carboxy-ethyl)-phenoxy]-butyric acid | 4.59 |
| 61 | 4-[3-[6-(3-Benzyloxy-5-thiophen-3-yl-phenoxy)-hexyl]-2-(2-carboxy-ethyl)-phenoxy]-butyric acid | 77.67 |
| 62 | 4-{2-(2-Carboxy-ethyl)-3-[6-(3-cyclopentylmethoxy-5-thiophen-3-yl-phenoxy)-hexyl]-phenoxy}-butyric acid | 7.98 |
| 63 | 4-{2-(2-Carboxy-ethyl)-3-[6-(5-cyclopentylmethoxy-3'-fluoro-biphenyl-3-yloxy)-hexyl]-phenoxy}-butyric acid | 32.52 |
| 64 | 4-[3-[6-(3-Acetyl-5-benzo[1,3]dioxol-5-yl-phenoxy)-hexyl]-2-(2-carboxy-ethyl)-phenoxy]-butyric acid | 2.95 |
| 65 | 4-[3-{6-[3-Acetyl-5-(2,3-dihydro-benzo[1,4]dioxin-6-yl)-phenoxy]-hexyl}-2-(2-carboxy-ethyl)-phenoxy]-butyric acid | 2.07 |
| 66 | 4-[3-[6-(5-Acetyl-biphenyl-3-yloxy)-hexyl]-2-(2-carboxy-ethyl)-phenoxy]-butyric acid | 3.33 |
| 67 | 4-[3-[6-(5-Acetyl-3'-fluoro-biphenyl-3-yloxy)-hexyl]-2-(2-carboxy-ethyl)-phenoxy]-butyric acid | 5.1 |
| 68 | 4-[3-[6-(3-Acetyl-5-thiophen-3-yl-phenoxy)-hexyl]-2- | 2 |

Assay results

| Example # | Compound name | LTB4 antagonism (HL-60 FLIPR) (nM) |
|---|---|---|
| | (2-carboxy-ethyl)-phenoxy]-butyric acid | |
| 69 | 4-[3-{6-[3-Acetyl-5-(2,2-difluoro-benzo[1,3]dioxol-5-yl)-phenoxy]-hexyl}-2-(2-carboxy-ethyl)-phenoxy]-butyric acid | 0.9 |
| 70 | 4-[3-[6-(3-Benzo[1,3]dioxol-5-yl-5-isobutyryl-phenoxy)-hexyl]-2-(2-carboxy-ethyl)-phenoxy]-butyric acid | 0.31 |
| 71 | 4-[3-[6-(3-Benzo[1,3]dioxol-5-yl-5-propionyl-phenoxy)-hexyl]-2-(2-carboxy-ethyl)-phenoxy]-butyric acid | 0.4 |
| 72 | 4-[3-[6-(3-Benzo[1,3]dioxol-5-yl-5-cyclopropanecarbonyl-phenoxy)-hexyl]-2-(2-carboxy-ethyl)-phenoxy]-butyric acid | 0.16 |
| 73 | 4-[3-[6-(3-Benzo[1,3]dioxol-5-yl-5-cyclopentanecarbonyl-phenoxy)-hexyl]-2-(2-carboxy-ethyl)-phenoxy]-butyric acid | 0.77 |

It is to be understood that the invention is not limited to the particular embodiments of the invention described above, as variations of the particular embodiments may be made and still fall within the scope of the appended claims.

What is claimed is:

1. A compound of formula (I):

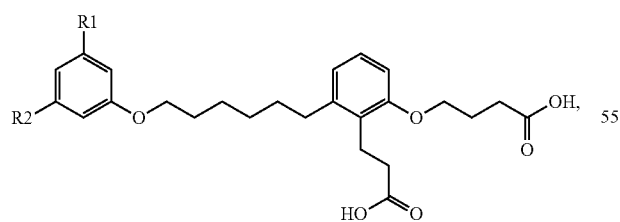

(I)

wherein:
R1 is lower alkyl, alkoxy, alkoyl, dimethylaminomethyl, cyanomethyl, benzyloxy, cyclopentylmethoxy, cyclopropanecarbonyl or cyclopentanecarbonyl; and
R2 is benzo[1,3]dioxol, benzo[1,4]dioxin, benzothiazole, difluoro-benzo[1,3]dioxole, cycloalkyl, aryl, unsubstituted or mono-, di- or tri-substituted with halogen, hydroxy, alkoxy, lower alkyl, —$CF_3$, —$OCF_3$ or methanesulfonyl, heteroaryl, unsubstituted or mono-, di- or tri-substituted with lower alkyl, halogen or hydroxy, N-aryl or indole, unsubstituted or substituted with lower alkyl, or a pharmaceutically acceptable salt thereof.

2. The compound according to claim 1, wherein:
R1 is lower alkyl, alkoxy or alkoyl; and
R2 is benzo[1,3]dioxol, benzo[1,4]dioxin, benzothiazole, difluoro-benzo[1,3]dioxole, cycloalkyl, aryl, unsubstituted or mono-, di- or tri-substituted with halogen, hydroxy, alkoxy, lower alkyl, —$CF_3$, —$OCF_3$ or methanesulfonyl, heteroaryl, unsubstituted or mono-, di- or tri-substituted with lower alkyl, halogen or hydroxy, N-aryl or indole, unsubstituted or substituted with lower alkyl.

3. The compound according to claim 1, wherein:
R1 is dimethylaminomethyl, cyanomethyl, benzyloxy, cyclopentylmethoxy, cyclopropanecarbonyl or cyclopentanecarbonyl; and
R2 is benzo[1,3]dioxol, benzo[1,4]dioxin, benzothiazole, difluoro-benzo[1,3]dioxole, cycloalkyl, aryl, unsubstituted or mono-, di- or tri-substituted with halogen, hydroxy, alkoxy, lower alkyl, —$CF_3$, —$OCF_3$ or methanesulfonyl, heteroaryl, unsubstituted or mono-, di- or tri-substituted with lower alkyl, halogen or hydroxy, N-aryl or indole, unsubstituted or substituted with lower alkyl.

4. The compound according to claim 1, wherein R1 is hydroxymethyl, methoxymethyl, ethoxy, ethoxymethyl, benzyloxy, acetyl or propionyl.

5. The compound according to claim 1, wherein R1 is dimethylaminomethyl, cyanomethyl, benzyloxy, cyclopentylmethoxy, cyclopropanecarbonyl or cyclopentanecarbonyl.

6. The compound according to claim 1, wherein said aryl at R2 is phenyl, unsubstituted or mono-, di- or tri-substituted with halogen, hydroxy, alkoxy, lower alkyl, —$CF_3$, —$OCF_3$ or methanesulfonyl.

7. The compound according to claim 1, wherein said heteroaryl at R2 is thiophene, pyrimidine or pyridine, unsubstituted or mono-, di- or tri-substituted with lower alkyl, halogen or hydroxy.

8. The compound according to claim 1, wherein said compound is:
4-[3-[6-(3-Benzo[1,3]dioxol-5-yl-5-hydroxymethyl-phenoxy)-hexyl]-2-(2-carboxy-ethyl)-phenoxy]-butyric acid,
4-{2-(2-Carboxy-ethyl)-3-[6-(5-hydroxymethyl-biphenyl-3-yloxy)-hexyl]-phenoxy}-butyric acid,
4-{2-(2-Carboxy-ethyl)-3-[6-(3-hydroxymethyl-5-thiophen-3-yl-phenoxy)-hexyl]-phenoxy}-butyric acid,
4-{2-(2-Carboxy-ethyl)-3-[6-(4'-fluoro-5-hydroxymethyl-biphenyl-3-yloxy)-hexyl]-phenoxy}-butyric acid,
4-{2-(2-Carboxy-ethyl)-3-[6-(4'-chloro-5-hydroxymethyl-biphenyl-3-yloxy)-hexyl]-phenoxy}-butyric acid,
4-(2-(2-Carboxy-ethyl)-3-{6-[3-(2,3-dihydro-benzo[1,4]dioxin-6-yl)-5-hydroxymethyl-phenoxy]-hexyl}-phenoxy)-butyric acid,
4-{2-(2-Carboxy-ethyl)-3-[6-(5-hydroxymethyl-4'-methanesulfonyl-biphenyl-3-yloxy)-hexyl]-phenoxy}-butyric acid,
4-[3-[6-(3-Benzo[1,3]dioxol-5-yl-5-methoxymethyl-phenoxy)-hexyl]-2-(2-carboxy-ethyl)-phenoxy]-butyric acid,
4-{2-(2-Carboxy-ethyl)-3-[6-(5-methoxymethyl-biphenyl-3-yloxy)-hexyl]-phenoxy}-butyric acid, 4-{2-(2-Carboxy-ethyl)-3-[6-(4'-fluoro-5-methoxymethyl-biphenyl-3-yloxy)-hexyl]-phenoxy}-butyric acid, 4-{2-(2-Carboxy-ethyl)-3-[6-(4'-chloro-5-methoxymethyl-biphenyl-3-yloxy)-hexyl]-phenoxy}-butyric acid, 4-(2-(2-Carboxy-ethyl)-3-{6-[3-(2,3-dihydro-benzo[1,4]dioxin-6-yl)-5-methoxymethyl-phenoxy]-hexyl}-phenoxy)-butyric acid, 4-(2-(2-Carboxy-ethyl)-3-{6-[3-methoxymethyl-5-(4-methyl-thiophen-3-yl)-phenoxy]-hexyl}-phenoxy)-butyric acid, 4-{2-(2-Carboxy-ethyl)-3-[6-(3'-fluoro-5-methoxymethyl-biphenyl-3-yloxy)-hexyl]-phenoxy}-butyric acid, 4-{2-(2-Carboxy-ethyl)-3-[6-(2'-fluoro-5-methoxymethyl-biphenyl-3-yloxy)-hexyl]-phenoxy}-butyric acid, 4-{2-(2-Carboxy-ethyl)-3-[6-(3',5'-difluoro-5-methoxymethyl-biphenyl-3-yloxy)-hexyl]-phenoxy}-butyric acid, 4-{2-(2-Carboxy-ethyl)-3-[6-(5-methoxymethyl-4'-trifluoromethyl-biphenyl-3-yloxy)-hexyl]-phenoxy}-butyric acid, 4-{2-(2-Carboxy-ethyl)-3-[6-(3'-chloro-5-methoxymethyl-biphenyl-3-yloxy)-hexyl]-phenoxy}-butyric acid, 4-{2-(2-Carboxy-ethyl)-3-[6-(3'-methoxy-5-methoxymethyl-biphenyl-3-yloxy)-hexyl]-phenoxy}-butyric acid or 4-{2-(2-Carboxy-ethyl)-3-[6-(5-methoxymethyl-4'-trifluoromethoxy-biphenyl-3-yloxy)-hexyl]-phenoxy}-butyric acid.

9. The compound according to claim 1, wherein said compound is:

4-{2-(2-Carboxy-ethyl)-3-[6-(3',4'-difluoro-5-methoxymethyl-biphenyl-3-yloxy)-hexyl]-phenoxy}-butyric acid, 4-{2-(2-Carboxy-ethyl)-3-[6-(3-methoxymethyl-5-pyrimidin-5-yl-phenoxy)-hexyl]-phenoxy}-butyric acid, 4-(2-(2-Carboxy-ethyl)-3-{6-[3-(1H-indol-5-yl)-5-methoxymethyl-phenoxy]-hexyl}-phenoxy)-butyric acid, 4-{2-(2-Carboxy-ethyl)-3-[6-(4'-methanesulfonyl-5-methoxymethyl-biphenyl-3-yloxy)-hexyl]-phenoxy}-butyric acid, 4-[3-[6-(3-Benzo[1,3]dioxol-5-yl-5-ethoxymethyl-phenoxy)-hexyl]-2-(2-carboxy-ethyl)-phenoxy]-butyric acid, 4-{2-(2-Carboxy-ethyl)-3-[6-(5-ethoxymethyl-4'-fluoro-biphenyl-3-yloxy)-hexyl]-phenoxy}-butyric acid, 4-{2-(2-Carboxy-ethyl)-3-[6-(5-ethoxymethyl-4'-trifluoromethyl-biphenyl-3-yloxy)-hexyl]-phenoxy}-butyric acid, 4-{2-(2-Carboxy-ethyl)-3-[6-(4'-chloro-5-ethoxymethyl-biphenyl-3-yloxy)-hexyl]-phenoxy}-butyric acid, 4-{2-(2-Carboxy-ethyl)-3-[6-(5-ethoxymethyl-4'-methanesulfonyl-biphenyl-3-yloxy)-hexyl]-phenoxy}-butyric acid, 4-[3-[6-(3-Benzo[1,3]dioxol-5-yl-5-dimethylaminomethyl-phenoxy)-hexyl]-2-(2-carboxy-ethyl)-phenoxy]-butyric acid, 4-{2-(2-Carboxy-ethyl)-3-[6-(3-dimethylaminomethyl-5-thiophen-3-yl-phenoxy)-hexyl]-phenoxy}-butyric acid, 4-{2-(2-Carboxy-ethyl)-3-[6-(5-dimethylaminomethyl-biphenyl-3-yloxy)-hexyl]-phenoxy}-butyric acid, 4-{2-(2-Carboxy-ethyl)-3-[6-(5-dimethylaminomethyl-4'-fluoro-biphenyl-3-yloxy)-hexyl]-phenoxy}-butyric acid, 4-{2-(2-Carboxy-ethyl)-3-[6-(4'-chloro-5-dimethylaminomethyl-biphenyl-3-yloxy)-hexyl]-phenoxy}-butyric acid, 4-{2-(2-Carboxy-ethyl)-3-[6-(5-dimethylaminomethyl-3'-fluoro-4'-methyl-biphenyl-3-yloxy)-hexyl]-phenoxy}-butyric acid, 4-{2-(2-Carboxy-ethyl)-3-[6-(5-dimethylaminomethyl-3'-fluoro-biphenyl-3-yloxy)-hexyl]-phenoxy}-butyric acid, 4-{2-(2-Carboxy-ethyl)-3-[6-(5-dimethylaminomethyl-4'-trifluoromethyl-biphenyl-3-yloxy)-hexyl]-phenoxy}-butyric acid, 4-{2-(2-Carboxy-ethyl)-3-[6-(5-dimethylaminomethyl-4'-methanesulfonyl-biphenyl-3-yloxy)-hexyl]-phenoxy}-butyric acid, 4-{2-(2-Carboxy-ethyl)-3-[6-(5-dimethylaminomethyl-3'-methanesulfonyl-biphenyl-3-yloxy)-hexyl]-phenoxy}-butyric acid or 4-{2-(2-Carboxy-ethyl)-3-[6-(3-dimethylaminomethyl-5-pyridin-4-yl-phenoxy)-hexyl]-phenoxy}-butyric acid.

10. The compound according to claim 1, wherein said compound is:

4-{2-(2-Carboxy-ethyl)-3-[6-(3-cyanomethyl-5-thiophen-3-yl-phenoxy)-hexyl]-phenoxy}-butyric acid, 4-{2-(2-Carboxy-ethyl)-3-[6-(5-cyanomethyl-biphenyl-3-yloxy)-hexyl]-phenoxy}-butyric acid, 4-[3-[6-(3-Benzo[1,3]dioxol-5-yl-5-ethoxy-phenoxy)-hexyl]-2-(2-carboxy-ethyl)-phenoxy]-butyric acid, 4-{2-(2-Carboxy-ethyl)-3-[6-(5-ethoxy-biphenyl-3-yloxy)-hexyl]-phenoxy}-butyric acid, 4-{2-(2-Carboxy-ethyl)-3-[6-(3-ethoxy-5-thiophen-3-yl-phenoxy)-hexyl]-phenoxy}-butyric acid, 4-(2-(2-Carboxy-ethyl)-3-{6-[3-(2,3-dihydro-benzo[1,4]dioxin-6-yl)-5-ethoxy-phenoxy]-hexyl}-phenoxy)-butyric acid, 4-{2-(2-Carboxy-ethyl)-3-[6-(5-ethoxy-3'-fluoro-biphenyl-3-yloxy)-hexyl]-phenoxy}-butyric acid, 4-{2-(2-Carboxy-ethyl)-3-[6-(5-ethoxy-4'-fluoro-biphenyl-3-yloxy)-hexyl]-phenoxy}-butyric acid, 4-{2-(2-Carboxy-ethyl)-3-[6-(4'-chloro-5-ethoxy-biphenyl-3-yloxy)-hexyl]-phenoxy}-butyric acid, 4-{2-(2-Carboxy-ethyl)-3-[6-(5-ethoxy-3',4'-difluoro-biphenyl-3-yloxy)-hexyl]-phenoxy}-butyric acid, 4-{2-(2-Carboxy-ethyl)-3-[6-(5-ethoxy-4'-methanesulfonyl-biphenyl-3-yloxy)-hexyl]-phenoxy}-butyric acid, 4-(2-(2-Carboxy-ethyl)-3-{6-[3-(2-chloro-pyridin-4-yl)-5-ethoxy-phenoxy]-hexyl}-phenoxy)-butyric acid, 4-{2-(2-Carboxy-ethyl)-3-[6-(3-ethoxy-5-pyrimidin-5-yl-phenoxy)-hexyl]-phenoxy}-butyric acid, 4-(2-(2-Carboxy-ethyl)-3-{6-[3-ethoxy-5-(1H-indol-5-yl)-phenoxy]-hexyl}-phenoxy)-butyric acid, 4-(2-(2-Carboxy-ethyl)-3-{6-[3-ethoxy-5-(1H-indol-6-yl)-phenoxy]-hexyl}-phenoxy)-butyric acid, 4-[3-[6-(3-Benzothiazol-5-yl-5-ethoxy-phenoxy)-hexyl]-2-(2-carboxy-ethyl)-phenoxy]-butyric acid, 4-(2-(2-Carboxy-ethyl)-3-{6-[3-(2,2-difluoro-benzo[1,3]dioxol-5-yl)-5-ethoxy-phenoxy]-hexyl}-phenoxy)-butyric acid, 4-[3-[6-(5-Benzyloxy-biphenyl-3-yloxy)-hexyl]-2-(2-carboxy-ethyl)-phenoxy]-butyric acid, 4-[3-[6-(5-Benzyloxy-3'-fluoro-biphenyl-3-yloxy)-hexyl]-2-(2-carboxy-ethyl)-phenoxy]-butyric acid, 4-[3-[6-(3-Benzo[1,3]dioxol-5-yl-5-benzyloxy-phenoxy)-hexyl]-2-(2-carboxy-ethyl)-phenoxy]-butyric acid, 4-[3-[6-(3-Benzyloxy-5-thiophen-3-yl-phenoxy)-hexyl]-2-(2-carboxy-ethyl)-phenoxy]-butyric acid, 4-{2-(2-Carboxy-ethyl)-3-[6-(3-cyclopentylmethoxy-5-thiophen-3-yl-phenoxy)-hexyl]-phenoxy}-butyric acid, 4-{2-(2-Carboxy-ethyl)-3-[6-(5-cyclopentylmethoxy-3'-fluoro-biphenyl-3-yloxy)-hexyl]-phenoxy}-butyric acid, 4-[3-[6-(3-Acetyl-5-benzo[1,3]dioxol-5-yl-phenoxy)-hexyl]-2-(2-carboxy-ethyl)-phenoxy]-butyric acid, 4-[3-{6-[3-Acetyl-5-(2,3-dihydro-benzo[1,4]dioxin-6-yl)-phenoxy]-hexyl}-2-(2-carboxy-ethyl)-phenoxy]-butyric acid, 4-[3-[6-(5-Acetyl-biphenyl-3-yloxy)-hexyl]-2-(2-carboxy-ethyl)-phenoxy]-butyric acid, 4-[3-[6-(5-Acetyl-3'-fluoro-biphenyl-3-yloxy)-hexyl]-2-(2-carboxy-ethyl)-phenoxy]-butyric acid, 4-[3-[6-(3-Acetyl-5-thiophen-3-yl-phenoxy)-hexyl]-2-(2-carboxy-ethyl)-phenoxy]-butyric acid, 4-[3-{6-[3-Acetyl-5-(2,2-difluoro-benzo[1,3]dioxol-5-yl)-phenoxy]-hexyl}-2-(2-carboxy-ethyl)-phenoxy]-butyric acid, 4-[3-[6-(3-Benzo[1,3]dioxol-5-yl-5-isobutyryl-phenoxy)-hexyl]-2-(2-carboxy-ethyl)-phenoxy]-butyric acid, 4-[3-[6-(3-Benzo[1,3]dioxol-5-yl-5-propionyl-phenoxy)-hexyl]-2-(2-carboxy-ethyl)-phenoxy]-butyric acid, 4-[3-[6-(3-Benzo[1,3]dioxol-5-yl-5-cyclopentanecarbonyl-phenoxy)-hexyl]-2-(2-carboxy-ethyl)-phenoxy]-butyric acid, 4-[3-[6-(3-Benzo[1,3]dioxol-5-yl-5-cyclopropanecarbonyl-phenoxy)-hexyl]-2-(2-carboxy-ethyl)-phenoxy]-butyric acid or 4-[3-[6-(3-Benzo[1,3]dioxol-5-yl-5-cyclopentanecarbonyl-phenoxy)-hexyl]-2-(2-carboxy-ethyl)-phenoxy]-butyric acid.

11. A pharmaceutical composition, comprising a therapeutically effective amount of a compound according to claim 1 or a pharmaceutically acceptable salt thereof and a pharmaceutically acceptable carrier.

* * * * *